United States Patent
Keravala

(10) Patent No.: US 11,352,644 B2
(45) Date of Patent: Jun. 7, 2022

(54) COMPOSITIONS AND METHODS FOR ENHANCED GENE EXPRESSION

(71) Applicant: Adverum Biotechnologies, Inc., Redwood City, CA (US)

(72) Inventor: Annahita Keravala, Palo Alto, CA (US)

(73) Assignee: Adverum Biotechnologies, Inc., Redwood City, CA (US)

( * ) Notice: Subject to any disclaimer, the term of this patent is extended or adjusted under 35 U.S.C. 154(b) by 0 days.

(21) Appl. No.: 16/998,540

(22) Filed: Aug. 20, 2020

(65) Prior Publication Data

US 2021/0040501 A1 Feb. 11, 2021

Related U.S. Application Data

(63) Continuation of application No. 16/494,203, filed as application No. PCT/US2018/022996 on Mar. 16, 2018.

(60) Provisional application No. 62/472,892, filed on Mar. 17, 2017.

(51) Int. Cl.
| | |
|---|---|
| C12N 15/63 | (2006.01) |
| A61K 48/00 | (2006.01) |
| C07H 21/04 | (2006.01) |
| C12N 15/86 | (2006.01) |
| C07K 14/71 | (2006.01) |
| A01K 67/00 | (2006.01) |

(52) U.S. Cl.
CPC .......... *C12N 15/86* (2013.01); *A61K 48/0066* (2013.01); *C07K 14/71* (2013.01); *C12N 2750/14143* (2013.01); *C12N 2800/22* (2013.01); *C12N 2830/15* (2013.01); *C12N 2830/42* (2013.01); *C12N 2830/50* (2013.01)

(58) Field of Classification Search
CPC .......... C12N 15/86; C12N 2750/14143; C12N 2800/22; C12N 2830/15; C12N 2830/42; C12N 2830/50; A61K 48/0066; C07K 14/71

See application file for complete search history.

(56) References Cited

U.S. PATENT DOCUMENTS

| | | | |
|---|---|---|---|
| 4,522,811 A | 6/1985 | Eppstein et al. | |
| 5,436,146 A | 7/1995 | Shenk et al. | |
| 5,712,380 A | 1/1998 | Kendall et al. | |
| 5,753,500 A | 5/1998 | Shenk et al. | |
| 5,861,484 A | 1/1999 | Kendall et al. | |
| 6,040,183 A | 3/2000 | Ferrari et al. | |
| 6,087,129 A * | 7/2000 | Newgard et al. | |
| 6,093,570 A | 7/2000 | Ferrari et al. | |
| 6,548,286 B1 | 4/2003 | Samulski et al. | |
| 7,071,159 B2 | 7/2006 | Kendall et al. | |
| 7,186,699 B2 * | 3/2007 | Harding et al. | |
| 7,371,542 B2 * | 5/2008 | Ivanova et al. | |
| 7,585,676 B2 | 9/2009 | Mitrophanous et al. | |
| 7,635,474 B2 | 12/2009 | Daly et al. | |
| 7,858,367 B2 | 12/2010 | Amalfitano et al. | |
| 8,187,836 B2 * | 5/2012 | Hsieh | |
| 8,900,858 B2 | 12/2014 | Trono et al. | |
| 9,193,956 B2 | 11/2015 | Schaffer et al. | |
| 9,233,131 B2 | 1/2016 | Schaffer et al. | |
| 9,428,767 B2 * | 8/2016 | Minshull et al. | |
| 9,441,244 B2 | 9/2016 | Schaffer et al. | |
| 9,458,517 B2 | 10/2016 | Schaffer et al. | |
| 9,587,282 B2 | 3/2017 | Schaffer et al. | |
| 9,856,539 B2 | 1/2018 | Schaffer et al. | |
| 9,943,573 B2 | 4/2018 | Constable et al. | |
| 10,004,788 B2 | 6/2018 | Constable et al. | |
| 10,041,077 B2 * | 8/2018 | Minshull et al. | |
| 10,046,016 B2 | 8/2018 | Schaffer et al. | |
| 10,202,657 B2 | 2/2019 | Schaffer et al. | |
| 10,214,566 B2 | 2/2019 | Schaffer et al. | |
| 10,214,785 B2 | 2/2019 | Schaffer et al. | |
| 2002/0168342 A1 | 11/2002 | Wang et al. | |
| 2004/0110295 A1 | 6/2004 | Punnonen et al. | |
| 2010/0120152 A1 | 5/2010 | Wooddell et al. | |
| 2012/0164106 A1 | 6/2012 | Schaffer et al. | |
| 2013/0323302 A1 | 12/2013 | Constable et al. | |
| 2014/0294771 A1 | 10/2014 | Schaffer et al. | |
| 2014/0364338 A1 | 12/2014 | Schaffer et al. | |
| 2015/0225702 A1 | 8/2015 | Schaffer et al. | |
| 2015/0232953 A1 | 8/2015 | Schaffer et al. | |
| 2016/0017295 A1 | 1/2016 | Schaffer et al. | |
| 2016/0184394 A1 | 6/2016 | Schaffer et al. | |
| 2016/0340393 A1 | 11/2016 | Schaffer et al. | |
| 2016/0340691 A1 | 11/2016 | Minshull et al. | |
| 2016/0375151 A1 | 12/2016 | Schaffer et al. | |
| 2016/0376323 A1 | 12/2016 | Schaffer et al. | |

(Continued)

FOREIGN PATENT DOCUMENTS

| | | |
|---|---|---|
| EP | 1591523 A1 | 11/2005 |
| JP | 2017506230 A | 3/2017 |

(Continued)

OTHER PUBLICATIONS

Stewart, M. Aflibercept (VEGF Trap-eye): the newest anti-VEGF drug. Br. J. Ophthalmol. 96:1157-1158, (Year: 2012).*
Alam et al. Lung surfactant protein B promoter function is dependent on the helical phasing, orientation and combinatorial actions of cis-DNA elements. Gene 282:103-111, (Year: 2002).*
Muller et al. Repression of lac promoter as a function of distance, phase and quality of an auxiliary lac operator. J. Mol. Biol. 257:21-29, (Year: 1996).*

(Continued)

*Primary Examiner* — Quang Nguyen
(74) *Attorney, Agent, or Firm* — Cooley LLP

(57) ABSTRACT

The present disclosure provides polynucleotide cassettes, expression vectors, and methods for the expression of a gene in mammalian cells.

17 Claims, 12 Drawing Sheets

Specification includes a Sequence Listing.

(56) References Cited

U.S. PATENT DOCUMENTS

| | | | |
|---|---|---|---|
| 2018/0127471 | A1 | 5/2018 | Keravala et al. |
| 2018/0289757 | A1 | 10/2018 | Schaffer et al. |
| 2018/0311319 | A1 | 11/2018 | Constable et al. |
| 2019/0100582 | A1 | 4/2019 | Blumenkranz et al. |
| 2019/0169237 | A1 | 6/2019 | Schaffer et al. |
| 2019/0218627 | A1 | 7/2019 | Schaffer et al. |
| 2020/0010851 | A1 | 1/2020 | Keravala |

FOREIGN PATENT DOCUMENTS

| | | | |
|---|---|---|---|
| WO | WO-2004070030 A1 | 8/2004 | |
| WO | WO 2005/005610 A2 | 1/2005 | |
| WO | WO-2009091912 A2 | 7/2009 | |
| WO | WO 2012/145601 A2 | 10/2012 | |
| WO | WO 2013/173129 A2 | 11/2013 | |
| WO | WO-2015120309 A1 | 8/2015 | |
| WO | WO-2015142941 A1 | 9/2015 | |
| WO | WO 2016/073693 A1 | 5/2016 | |
| WO | WO-2016141078 A1 | 9/2016 | |
| WO | WO-2017112868 A1 | 6/2017 | |
| WO | WO-2017190125 A1 | 11/2017 | |
| WO | WO 2017/218981 A2 | 12/2017 | |
| WO | WO 2018/075798 A1 | 4/2018 | |
| WO | WO 2018/160686 A1 | 9/2018 | |
| WO | WO 2018/170473 A1 | 9/2018 | |

OTHER PUBLICATIONS

Xie et al. Domains of the rat rDNA promoter must be aligned stereospecifically. Molecular and Cellular Biology 12:1266-1275, (Year: 1992).*
U.S. Appl. No. 16/488,689, filed Aug. 26, 2019, Keravala.
Agarwal, et al., "Scaffold Attachment Region-Mediated Enhancement of Retroviral Vector Expression in Primary T Cells". J Virol. (May 1998); 72(5): 3720-3728.
Buchman and Berg, "Comparison of intron-dependent and intron-independent gene expression". Mol Cell Biol. (Oct. 1988); 8(10): 4395-4405.
Chiuchiolo, et al., "Intrapleural administration of an AAVrh.10 vector coding for human α1-antitrypsin for the treatment of α1-antitrypsin deficiency". Hum Gene Ther Clin Dev. (Dec. 2013); 24(4): 161-1773.
Cid-Arregui, et al., "A Synthetic E7 Gene of Human Papillomavirus Type 16 That Yields Enhanced Expression of the Protein in Mammalian Cells and Is Useful for DNA Immunization Studies". J Virol. (Apr. 2003); 77(8): 4928-4937.
Dalkara, Deniz, et al., "In vivo-directed evolution of a new adeno-associated virus for therapeutic outer retinal gene delivery from the vitreous." Science Translational Medicine (2013); 5 (189): 189ra76-189ra76.
Durocher, et al., "High-level and high-throughput recombinant protein production by transient transfection of suspension-growing human 293-EBNA1 cells". Nucleic Acids Res. (Jan. 15, 2002); 30(2): e9, pp. 1-9.
Higashimoto, et al., "The woodchuck hepatitis virus post-transcriptional regulatory element reduces readthrough transcription from retroviral vectors". Gene Ther. (Sep. 2007); 14(17): 1298-1304. Epub Jun. 28, 2007.
Huang and Gorman, "The Simian Virus 40 Small-t Intron, Present in Many Common Expression Vectors, Leads to Aberrant Splicing", Molecular and Cellular Biology (Apr. 1990); 10(4): 1805-1810.
Kendall and Thomas, "Inhibition of vascular endothelial cell growth factor activity by an endogenously encoded soluble receptor". PNAS (Nov. 15, 1993); 90(22): 10705-10709.
Klimczak, et al., "A novel adeno-associated viral variant for efficient and selective intravitreal transduction of rat muller cells." PLoS One (Oct. 2009); 4(10): e7467.
Logan and Shenk, "Adenovirus tripartite leader sequence enhances translation of mRNAs late after infection". Proc Natl Acad Sci USA. (Jun. 1984); 81(12): 3655-3659.

PCT/US2018/022996, International Preliminary Report on Patentability dated Sep. 17, 2019, 5 pages.
PCT/US2018/022996, International Search Report and Written Opinion dated May 22, 2018, 9 pages.
Senapathy, et al., "Splice junctions, branch point sites, and exons: sequence statistics, identification, and applications to genome project". Methods Enzymol. (1990); 183: 252-278.
Stoller and Aboussouan, "A review of α1 -antitrypsin deficiency" Am J Respir Grit Care Med. (Feb. 1, 2012); 185(3): 246-259. Epub Sep. 29, 2011.
Wiesmann, et al., "Crystal Structure at 1.7 Å Resolution of VEGF in Complex with Domain 2 of the Flt-1 Receptor". Cell (Nov. 28, 1997); 91(5): 695-704.
Wu and Krainer, "AT-AC pre-mRNA splicing mechanisms and conservation of minor introns in voltage-gated ion channel genes". Mol Cell Biol (May 1999); 19(5): 3225-3236.
Xu, et al., "Optimization of transcriptional regulatory elements for constructing plasmid vectors". Gene (Jul. 11, 2001); 272(1-2): 149-156.
Xu, et al., "Strength evaluation of transcriptional regulatory elements for transgene expression by adenovirus vector." Journal of Controlled Release (Apr. 30, 2002); 81(1-2): 155-163.
U.S. Appl. No. 14/281,749, filed May 19, 2014, US 2015-0004101 A1, Jan. 1, 2015, U.S. Pat. No. 9,943,573, Apr. 17, 2018, Registered.
U.S. Appl. No. 14/660,657, filed Mar. 17, 2015, US 2015-0259395 A1, Sep. 17, 2015, U.S. Pat. No. 10,000,741, Jun. 19, 2018, Registered.
U.S. Appl. No. 15/388,380, filed Dec. 22, 2016, US 2017-0183647 A1, Jun. 29, 2017, U.S. Pat. No. 10,584,328, Mar. 10, 2020, Registered.
U.S. Appl. No. 15/851,650, filed Dec. 21, 2017, US 2018-0125948 A1, May 10, 2018, U.S. Pat. No. 10,004,788, Jun. 26, 2018, Registered.
U.S. Appl. No. 13/889,275, filed May 7, 2013, US 2013-0323302 A1, Dec. 5, 2013, Abandoned.
U.S. Appl. No. 14/281,765, filed May 19, 2014, US 2014-0341977 A1, Nov. 20, 2014, Abandoned.
U.S. Appl. No. 14/281,783, filed May 19, 2014, Abandoned.
U.S. Appl. No. 14/407,054, filed Jun. 10, 2013, US 2015-0111275 A1, Apr. 23, 2015, Abandoned.
U.S. Appl. No. 15/554,664, filed Mar. 2, 2016, US 2018-0066022 A1, Mar. 8, 2018, Allowed.
U.S. Appl. No. 15/939,674, filed Mar. 29, 2018, US 2018-0344197 A1, Dec. 6, 2018, Pending.
U.S. Appl. No. 15/788,446, filed Oct. 19, 2017, US 2018-0127471 A1, May 10, 2018, Pending.
U.S. Appl. No. 15/961,654, filed Apr. 24, 2018, US 2018-0311319 A1, Nov. 1, 2018, Pending.
U.S. Appl. No. 16/097,377, filed May 1, 2017, US 2019-0142975 A1, May 16, 2019, Pending.
U.S. Appl. No. 16/098,354, filed May 2, 2017, US 2019-0154667 A1, May 23, 2019, Pending.
U.S. Appl. No. 16/494,203, filed Aug. 13, 2019, US2020-0010851 A1, Jan. 9, 2020, Pending.
U.S. Appl. No. 16/750,736, filed Jan. 23, 2020, US 2020-0149033 A1, May 14, 2020, Pending.
U.S. Appl. No. 15/984,085, filed May 18, 2018, US 2018-0320145 A1, Nov. 8, 2018, Pending.
U.S. Appl. No. 16/488,689, filed Feb. 28, 2018, Pending.
Trindade, et al., "Precise: Software for Prediction of cis-Acting Regulatory Elements," Journal of Heredity (Sep./Oct. 2005); 96(5): 618-622. Advance Access publication Aug. 31, 2005.
Hagedorn, C. et al., "Scaffold/Matrix Attached Region-Based Nonviral Episomal Vectors", Human Gene Therapy, 2011, vol. 22, pp. 1-9.
Piechaczek, C. et al., "A Vector Based on the SV40 Origin of Replication and Chromosomal S/MARs Replicates Episomally in CHO Cells", Nucleic Acids Research, 1999, vol. 27, No. 2, pp. 426-428.

* cited by examiner

FIG. 1

Polynucleotide cassette constructs

| Cassette No. | First Enhancer | Promoter | Intron | 5'UTR | | Gene | Second Enhancer | RNA Export | polyA |
|---|---|---|---|---|---|---|---|---|---|
| 1 | EF1α | EF1a | | TPL | eMLP | Coding Sequence | Full EES | HPRE | HGH |
| 2 | | EF1a | EF1α | UTR2 | | Coding Sequence | 410-564 EES | WPRE | HGH |
| 3 | EF1α | EF1a | EF1α | UTR2 | | Coding Sequence | 511-810 EES | | BGH |
| 4 | EF1α | EF1a | EF1α | UTR1 | | Coding Sequence | 511-810 EES | | βGlobin |
| 5 | CMV | GAPDH | | UTR1 | | Coding Sequence | 511-810 EES | HPRE | HGH |
| 6 | CMV | GAPDH | | TPL | eMLP | Coding Sequence | 410-564 EES | WPRE | βGlobin |
| 7 | CMV | Actin | Actin | UTR1 | | Coding Sequence | 410-564 EES | HPRE | BGH |
| 8 | CMV | Actin | Actin | TPL | eMLP | Coding Sequence | 410-564 EES | | βGlobin |
| 9 | CMV | EF1a | EF1α | UTR1 | | Coding Sequence | 410-564 EES | | HGH |
| 10 | CMV | EF1a | EF1α | UTR2 | | Coding Sequence | 511-810 EES | WPRE | BGH |
| 11 | CMV | CMV | | TPL | eMLP | Coding Sequence | Full EES | | HGH |
| 12 | CMV | CMV | | TPL | eMLP | Coding Sequence | 410-564 EES | HPRE | BGH |
| 13 | CMV | Actin | | | eMLP | Coding Sequence | 511-810 EES | HPRE | βGlobin |
| 14 | CMV | CMV | CMVc | UTR1 | | Coding Sequence | Full EES | WPRE | βGlobin |
| 15 | CMV | CMV | | UTR2 | | Coding Sequence | Full EES | HPRE | βGlobin |
| 16 | CMV | CMV | | UTR1 | | Coding Sequence | Full EES | WPRE | BGH |
| 17 | CMV | GAPDH | CMVc | | | Coding Sequence | 511-810 EES | WPRE | HGH |
| 18 | CMV | Actin | | | eMLP | Coding Sequence | Full EES | | BGH |
| Base plasmid | CMV | EF1α | EF1α | | | Coding Sequence | | | Rb Globin |

Expression of sFLT1 from transduced pig retinal explants

COMPOSITIONS AND METHODS FOR ENHANCED GENE EXPRESSION

CROSS REFERENCE TO RELATED APPLICATIONS

This application is a Continuation of U.S. application Ser. No. 16/494,203, filed Sep. 13, 2019, which is a 371 National Phase Application of International Application No. PCT/US2018/022996, filed Mar. 16, 2018, which claims the benefit of United States Provisional Application Ser. No. 62/472,892, filed Mar. 17, 2017, the full disclosures of which is herein incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AVBI_009_02US_ST25.txt. The text file is 86 KB, was created on Aug. 19, 2020, and is being submitted electronically via EFS-Web.

FIELD OF THE INVENTION

This invention pertains to gene therapy of disorders.

BACKGROUND OF THE INVENTION

A promising approach to treating and preventing genetic diseases and other disorders is the delivery of therapeutic agents with a gene delivery vector. Viral vectors are highly efficient gene transfer vehicles and may be useful as gene delivery vectors. Adeno-associated virus (AAV) based vectors, in particular, are desirable due to the non-integrating nature of their viral life cycle.

A number of challenges remain, however, with regard to designing polynucleotide cassettes and expression vectors for use in gene therapy. One significant challenge is obtaining sufficient expression of the transgene in target cells following gene transfer. In some cases, effective treatment of a disease or genetic disorder using a gene delivery vector (e.g., recombinant virus) may depend on both robust expression and efficient secretion of the therapeutic polypeptide. Therefore, expression cassettes that are capable of driving high levels of secreted protein from the targeted (e.g., transduced) cell can be an important part of a therapeutically effective vector and a successful gene therapy method. Thus, there is a need for improved methods and optimized nucleic acid expression cassettes and vectors for expressing genes in mammalian cells.

The present invention meets this need.

SUMMARY OF THE INVENTION

The invention relates generally to the fields of molecular biology and virology, and in particular, to gene expression cassettes and vectors comprising them for the delivery of nucleic acid segments encoding selected therapeutic constructs (for example, peptides and polypeptides) to selected cells and tissues of vertebrate animals. These genetic constructs are useful in the development of gene delivery vectors, including for example, herpes simplex virus (HSV), adenovirus (AV), and AAV vectors, for the treatment of mammalian, and in particular, human diseases, disorders, and dysfunctions.

More specifically, the invention is directed to gene expression cassettes for enhanced expression of a secreted protein by a eukaryotic or mammalian cell, and to methods of making and using such cassettes for use in both research and therapeutic applications, including but not limited to a method of treating a disease or disorder caused by or associated with the deficiency, absence, or loss of function of one or more proteins in a subject in need thereof.

The present cassettes generally include a nucleic acid sequence, or transgene, encoding a polypeptide effective in the treatment of a medical condition in a human or non-human animal subject. In some embodiments, the polypeptide is a secretory polypeptide. The cassette can be incorporated into a viral vector, such as an adeno-associated virus (AAV) vector, which can then be administered to eukaryotic or mammalian cells in vitro (e.g., in cell culture) or to a mammalian subject suffering from or at risk for developing a medical condition.

The disclosed compositions may be utilized in a variety of investigative, diagnostic and therapeutic regimens, including the prevention and treatment of human diseases. For example, the present compositions may find use in the treatment of an ocular disease, angiogenesis-dependent disease, disease that responds to treatment with a vascular endothelial growth factor (VEGF) inhibitor, or in enzyme replacement therapy, wherein the disease is caused by or associated with a deficiency in or loss of function of an enzyme.

Methods and compositions are provided for preparing polynucleotide expression cassettes and gene delivery vector compositions, e.g., viral vectors, comprising these expression cassettes for use in the preparation of medicaments useful in central and targeted gene therapy of diseases, disorders, and dysfunctions in an animal, and in humans in particular.

Embodiments of the present invention comprise a non-naturally occurring polynucleotide cassette for enhanced expression of a transgene in a mammalian cell, comprising in 5' to 3' order: (a) a first enhancer region; (b) a promoter region; (c) a coding sequence encoding a polypeptide gene product; (d) a second enhancer region; and (e) a polyadenylation site. In some embodiments, the polynucleotide cassette further comprises a ribonucleic acid (RNA) export signal located downstream of the second enhancer and upstream of the polyadenylation site. In one embodiment the polynucleotide cassette does not contain an RNA export signal. In a more specific form, the cassette does not contain an RNA export signal downstream of the second enhancer and upstream of the polyadenylation site.

In yet other embodiments, the polynucleotide cassette further comprises an intron located downstream of the promoter and upstream of the coding sequence.

In still other embodiments, the polynucleotide cassette further comprises a 5' untranslated region (5'UTR) that is located upstream of the coding sequence and downstream of the promoter.

In preferred embodiments, the polypeptide gene product is a secretory protein.

Polynucleotide cassettes of the present invention comprise a first enhancer region located upstream of a promoter region. In preferred embodiments, the first enhancer region comprises a cytomegalovirus (CMV) sequence. In other embodiments, the first enhancer region comprises an elongation factor 1 alpha (EF1α) sequence. In certain embodiments the first enhancer region comprises a sequence with at least 85% identity SEQ ID NO: 1. In certain embodiments, the identity is at least 90%, at least 95% or at least 99%.

Polynucleotide cassettes of the present invention comprise a promoter region comprising a promoter sequence, or a functional fragment thereof. In some embodiments, the promoter region is specific for eukaryotic cells, or more specifically mammalian cells. In some embodiments, the promoter region comprises a promoter sequence selected from the group consisting of an actin promoter, a cytomegalovirus (CMV) promoter, an elongation factor 1 alpha (EF1a) promoter, and a glyceraldehyde 3-phosphate dehydrogenase (GAPDH) promoter. In preferred embodiments, the promoter region comprises a CMV promoter sequence or an EF1a promoter sequence. In certain embodiments the promoter region comprises a sequence with at least 85% identity to one of the following SEQ ID NO: 3, 4, or 96. In certain embodiments, the identity is at least 90%, at least 95% or at least 99%.

In some embodiments, polynucleotide cassettes of the present invention further comprise an intron region downstream of the promoter region. In some embodiments, the intron sequence is located downstream of the promoter and upstream of the 5'UTR. In some embodiments, the intron region comprises an elongation factor 1 alpha (EF1a), actin, or CMVc sequence. In certain embodiments the intron comprises a sequence with at least 85% identity to one of the following SEQ ID NO: 5, 18, or 97. In certain embodiments, the identity is at least 90%, at least 95% or at least 99%.

Polynucleotide cassettes of the present invention comprise an untranslated region 5' of the coding sequence, referred to herein as a 5'UTR. In some embodiments, the 5'UTR sequence is heterologous to the promoter sequence. The 5'UTR is located downstream of the promoter and upstream of the coding sequence. In some such embodiments, the 5'UTR comprises a sequence selected from the group consisting of UTR1, UTR2, an enhancer element from the adenovirus major late promoter (eMLP), and the tripartite leader sequence from adenovirus (TPL sequence). In some embodiments, the 5'UTR comprises a UTR1 sequence. In one embodiment, the 5'UTR comprises a UTR2 sequence. In preferred embodiments, the 5'UTR comprises, in 5' to 3' order, a TPL sequence and an eMLP sequence. In some embodiments, the 5'UTR does not comprise a polynucleotide ATG. In certain embodiments the 5' UTR comprises a sequence with at least 85% identity to one of the following SEQ ID NO: 6, 11, 12, or 19. In certain embodiments, the identity is at least 90%, at least 95% or at least 99%.

Embodiments of the present invention comprise polynucleotide cassettes for the enhanced expression of transgenes. Accordingly, polynucleotide cassettes of the present invention comprise a coding sequence, also referred to as a transgene. In one specific embodiment, the polynucleotide cassette comprises one coding sequence, or transgene, and does not comprise two or more transgenes. The transgene may encode a therapeutic agent such as for example a peptide or a polypeptide. In preferred embodiments, the transgene encodes a secretory polypeptide (also referred to herein as a secreted protein or secretory protein). Examples of secretory polypeptides that can be encoded by the coding sequence include, but are not limited to, soluble fms-like tyrosine kinase-1 (also known as sFLT-1), a VEGF-binding fragment of sFLT-1, aflibercept, and alpha-1 antitrypsin or $\alpha_1$-antitrypsin (A1AT). In some embodiments, the secretory polypeptide is an anti-angiogenic or anti-vascular endothelial growth factor (anti-VEGF) polypeptide.

The subject expression cassettes provide for enhanced expression of the transgene product (e.g., polypeptide) in a mammalian cell relative to the expression of the transgene product in the mammalian cell from a reference cassette. In preferred embodiments a subject expression cassette provides for enhanced expression of a secretory protein in a eukaryotic cell in vivo or in vitro (e.g., in a cell culture or tissue explant) relative to the expression of the secretory protein in the eukaryotic cell in vivo or in vitro from a reference cassette. In some aspects the eukaryotic cell is a mammalian cell. In still further aspects the mammalian cell is a human cell.

In some embodiments, the expression of a secretory polypeptide from the polynucleotide cassette in mammalian cells is at least about 2×, 3×, 5×, 9×, 10×, 20×, or 50× higher than the expression of the secretory polypeptide from a reference cassette in the mammalian cells in vitro or in vivo.

In some embodiments, the expression level of a non-secreted polypeptide obtained from the polynucleotide cassette in mammalian cells is approximately the same as, less than about 1.5× greater than, or less than about 2× greater than the expression level of the non-secreted polypeptide obtained from a reference cassette in the mammalian cells in vitro or in vivo. One non-limiting example of a non-secreted polypeptide is green fluorescent protein (GFP).

According to some embodiments, the reference cassette (also referred to herein as the CMV reference control cassette), referred to herein above and below, comprises, in 5' to 3' order, a CMV enhancer sequence (SEQ ID NO:2), a CMV promoter (SEQ ID NO:21), a chimeric intron (SEQ ID NO:22), a 5'UTR (SEQ ID NO:23), a coding sequence encoding the peptide or polypeptide gene product, a 3'UTR (SEQ ID NO:25), and an SV40 polyA sequence (SEQ ID NO:26).

According to specific embodiments, enhanced expression of the peptide or polypeptide is observed in vitro in mammalian cells selected from the group consisting of HeLa cells, HEK-293 cells, and ARPE-19 cells. In another embodiment, the mammalian cells are contained in a retinal tissue explant.

In some forms, the expression of the secretory protein from the polynucleotide cassette in mammalian cells in vitro or in vivo (e.g., in a subject) is at least 2×, at least 5×, at least 10×, or from about 5× to about 10× greater than the expression of the secretory protein from the CMV reference control cassette in the mammalian cells under the same conditions, wherein the CMV reference control cassette comprises, in 5' to 3' order, the CMV enhancer sequence set forth in SEQ ID NO:2, the CMV promoter sequence set forth in SEQ ID NO:21, the chimeric intron sequence set forth in SEQ ID NO:22, the 5'UTR sequence set forth in SEQ ID NO:23, a coding sequence encoding the secretory polypeptide, the 3'UTR sequence set forth in SEQ ID NO:25, and the SV40 polyA sequence set forth in SEQ ID NO:26. In some embodiments, the polynucleotide cassette increases the expression of the secretory protein in mammalian cells by at least 2-fold (2×), 5-fold (5×), 10-fold (10×), or from about 5- to about 10-fold as compared to the expression of the protein from the CMV reference control cassette in the mammalian cells. In one embodiment, the polynucleotide cassette enhances or increases the expression of a secreted protein in a transduced mammalian cell relative to the expression of the protein from the CMV reference control cassette in a transduced mammalian cell.

The polynucleotide cassette comprises a second enhancer region located downstream of the coding sequence and upstream of the polyadenylation signal sequence. When an RNA export signal sequence is present, the second enhancer sequence is located upstream of the RNA export signal (i.e., between the coding sequence and the RNA export signal), and the RNA export signal is located upstream of the polyadenylation signal. In preferred embodiments, the second enhancer region comprises an expression enhancer sequence (EES) selected from the group consisting of the full EES, 410-564 EES, and 511-810 EES.

In some embodiments, the polynucleotide cassette comprises an RNA export signal downstream of the second enhancer and upstream of the polyadenylation sequence (also referred to herein as a polyA sequence, polyA site, or polyadenylation region). The RNA export signal may comprise a sequence selected from the group consisting of human hepatitis B virus post-transcriptional element (HPRE) sequence and woodchuck hepatitis virus post-transcriptional element (WPRE) sequence. In certain embodiments the RNA export signal comprises a sequence with at least 85% identity to one of the following SEQ ID NO: 8, or 17. In certain embodiments, the identity is at least 90%, at least 95% or at least 99%.

A polynucleotide cassette according to the present invention comprises a polyadenylation site. The polyadenylation site may be located downstream of the second enhancer region or downstream of the RNA export region. In some embodiments, the polyadenylation region comprises a human growth hormone (HGH or hGH), bovine growth hormone (BGH or bGH), or beta-globin (βglobin) polyA sequence. In certain embodiments, the polyadenylation region comprises a sequence with at least 85% identity to one of the following SEQ ID NO: 9, 14, or 20. In certain embodiments, the identity is at least 90%, at least 95% or at least 99%.

Some embodiments of the present invention are directed to a polynucleotide cassette for enhanced or increased expression of a secretory protein by mammalian cells, as measured by the amount (e.g., concentration or quantity) of protein in the extracellular environment, relative to the expression of the protein by a reference cassette in the mammalian cells. The amount of protein in a sample can be measured by, for example, immunoassay.

In some embodiments, the polynucleotide cassette for enhanced expression of a transgene in a mammalian cell, comprises in 5' to 3' order: (a) a first enhancer region comprising a CMV sequence (SEQ ID NO:1); (b) a promoter region, comprising an EF1α sequence (SEQ ID NO:3); (c) an intron region comprising an EF1α sequence (SEQ ID NO:5); (d) a 5'UTR region comprising an UTR2 sequence (SEQ ID NO:6); (e) a coding sequence encoding a peptide or polypeptide; (f) a second enhancer region comprising a 511-810 EES sequence (SEQ ID NO:7); (g) an WPRE RNA export sequence (SEQ ID NO:8); and (h) a BGH polyadenylation site (SEQ ID NO:9). In certain of these embodiments, the polynucleotide cassette comprises one or more sequences selected from SEQ ID NO: 70-75 or a sequence with at least 85% identity thereto. In certain of these embodiments the 5' arm of the polynucleotide cassette comprises or consists of SEQ ID NO: 45 or a sequence with at least 85% identity thereto. In certain of these embodiments the 3' arm of the polynucleotide cassette comprises or consists of SEQ ID NO: 46 or a sequence with at least 85% identity thereto.

In other embodiments, the polynucleotide cassette for enhanced expression of a transgene in a mammalian cell, comprises in 5' to 3' order: (a) a first enhancer region comprising a CMV sequence (SEQ ID NO:1); (b) a promoter region, comprising a CMV sequence (SEQ ID NO:4); (c) a 5'UTR region comprising, in 5' to 3' order, TPL and eMLP sequences (SEQ ID NO:11 and SEQ ID NO:12, respectively); (d) a coding sequence encoding a peptide or polypeptide; (e) a second enhancer region comprising a full EES sequence (SEQ ID NO:13); and (f) a HGH polyadenylation site (SEQ ID NO:14). In certain of these embodiments, the polynucleotide cassette comprises one or more sequences selected from SEQ ID NO: 76-80 or a sequence with at least 85% identity thereto. In certain of these embodiments the 5' arm of the polynucleotide cassette comprises or consists of SEQ ID NO: 47 or a sequence with at least 85% identity thereto. In certain of these embodiments the 3' arm of the polynucleotide cassette comprises or consists of SEQ ID NO: 48 or a sequence with at least 85% identity thereto.

In other embodiments, the polynucleotide cassette for enhanced expression of a transgene in a mammalian cell, comprises in 5' to 3' order: (a) a first enhancer region comprising a CMV sequence (SEQ ID NO:1); (b) a promoter region, comprising a CMV sequence (SEQ ID NO:4); (c) a 5'UTR region comprising, in 5' to 3' order, TPL and eMLP sequences (SEQ ID NO:11 and SEQ ID NO:12, respectively); (e) a coding sequence encoding a peptide or polypeptide; (f) a second enhancer region comprising a 410-564 EES sequence (SEQ ID NO:16); (g) an HPRE RNA export sequence (SEQ ID NO:17); and (h) a BGH polyadenylation site (SEQ ID NO:9). In certain of these embodiments, the polynucleotide cassette comprises one or more sequences selected from SEQ ID NO: 81-86 or a sequence with at least 85% identity thereto. In certain of these embodiments the 5' arm of the polynucleotide cassette comprises or consists of SEQ ID NO: 49 or a sequence with at least 85% identity thereto. In certain of these embodiments the 3' arm of the polynucleotide cassette comprises or consists of SEQ ID NO: 50 or a sequence with at least 85% identity thereto.

In other embodiments, the polynucleotide cassette for enhanced expression of a transgene in a mammalian cell, comprises in 5' to 3' order: (a) a first enhancer region comprising a CMV sequence (SEQ ID NO:1); (b) a promoter region, comprising an actin sequence (SEQ ID NO:96); (c) a 5' UTR comprising an eMLP sequences (SEQ ID NO:12); (e) a coding sequence encoding a peptide or polypeptide; (f) a second enhancer region comprising a 511-810 EES sequence (SEQ ID NO:7); (g) an HPRE RNA export sequence (SEQ ID NO:17); and (h) a rabbit Beta Globin polyadenylation site (SEQ ID NO:20). In certain of these embodiments, the polynucleotide cassette comprises one or more sequences selected from SEQ ID NO: 87-91 or a sequence with at least 85% identity thereto. In certain of these embodiments the 5' arm of the polynucleotide cassette comprises or consists of SEQ ID NO: 51 or a sequence with at least 85% identity thereto. In certain of these embodiments the 3' arm of the polynucleotide cassette comprises or consists of SEQ ID NO: 52 or a sequence with at least 85% identity thereto.

In other embodiments, the polynucleotide cassette for enhanced expression of a transgene in a mammalian cell, comprises in 5' to 3' order: (a) a first enhancer region comprising a CMV sequence (SEQ ID NO:1); (b) a promoter region, comprising a CMV sequence (SEQ ID NO:4); (c) an intron region comprising an CMVc sequence (SEQ ID NO:18); (d) a 5'UTR region comprising a UTR1 sequence (SEQ ID NO:19); (e) a coding sequence encoding a peptide or a polypeptide; (f) a second enhancer region comprising a full EES sequence (SEQ ID NO:13); (g) an WPRE RNA export sequence (SEQ ID NO:8); and (h) a rabbit Beta Globin polyadenylation site (SEQ ID NO:20). In certain of these embodiments, the polynucleotide cassette comprises one or more sequences selected from SEQ ID NO: 92-95 or a sequence with at least 85% identity thereto. In certain of these embodiments the 5' arm of the polynucleotide cassette comprises or consists of SEQ ID NO: 53 or a sequence with at least 85% identity thereto. In certain of these embodiments the 3' arm of the polynucleotide cassette comprises or consists of SEQ ID NO: 54 or a sequence with at least 85% identity thereto.

In other embodiments, the polynucleotide cassette for enhanced expression of a transgene in a mammalian cell, comprises in 5' to 3' order: (a) a first enhancer region comprising a CMV sequence (SEQ ID NO:1); (b) a promoter region, comprising an actin sequence (SEQ ID NO:96); (c) an intron region comprising a chicken beta-actin sequence (SEQ ID NO:97); (d) a 5'UTR region comprising a UTR1 sequence (SEQ ID NO:19); (e) a coding sequence encoding a peptide or a polypeptide; (f) a second enhancer region comprising a 410-564 EES sequence (SEQ ID NO:16); (g) an HPRE RNA export sequence (SEQ ID NO:17); and (h) a BGH polyadenylation site (SEQ ID NO:9). In certain of these embodiments, the polynucleotide cassette comprises one or more sequences selected from SEQ ID NO: 92-95 or a sequence with at least 85% identity thereto. In certain of these embodiments the 5' arm of the polynucleotide cassette comprises or consists of SEQ ID NO: 39 or a sequence with at least 85% identity thereto. In certain of these embodiments the 3' arm of the polynucleotide cassette comprises or consists of SEQ ID NO: 40 or a sequence with at least 85% identity thereto.

In certain embodiments, the polynucleotide cassette comprises or consists essentially of in 5' to 3' order: (a) a 5' arm; (b) a coding sequence encoding a peptide or a polypeptide; and (c) a 3' arm. In certain of these embodiments, the 5' arm comprises a sequence selected from the group consisting of SEQ ID NO: 27, 29, 31, 33, 35, 37, 39, 41, 43, 45, 47, 49, 51, 53, 55, 57, 59, and 61 or a sequence with at least 85% identity thereto, and the 3' arm comprises a sequence selected from the group consisting of SEQ ID NO: 28, 30, 32, 34, 36, 38, 40, 42, 44, 46, 48, 50, 52, 54, 56, 58, 60, and 62 or a sequence with at least 85% identity thereto. In particular embodiments, the 5' arm and 3' arm are, respectively, SEQ ID NO: 27 and 28, or SEQ ID NO: 29 and 30, or SEQ ID NO: 31 and 32, or SEQ ID NO: 33 and 34, or SEQ ID NO: 35 and 36, or SEQ ID NO: 37 and 38, or SEQ ID NO: 39 and 40, or SEQ ID NO: 41 and 42, or SEQ ID NO: 43 and 44, or SEQ ID NO: 45 and 46, or SEQ ID NO: 47 and 48, or SEQ ID NO: 49 and 50, or SEQ ID NO: 51 and 52, or SEQ ID NO: 53 and 54 or SEQ ID NO: 55 and 56, or SEQ ID NO: 57 and 58, or SEQ ID NO: 59 and 60, or SEQ ID NO: 61 and 62.

In preferred forms of the invention, the peptide or polypeptide encoded by the coding sequence in the subject polynucleotide cassette is one that is secreted or exported from the cell following its expression in the cell.

In some aspects of the invention, gene delivery vectors are provided comprising a polynucleotide cassette of the present invention. In some embodiments, the gene delivery vector is a recombinant virus comprising (a) a capsid protein, and (b) a polynucleotide cassette of the present invention. In more specific embodiments, the recombinant virus is a recombinant adeno-associated virus (AAV), wherein the recombinant adeno-associated virus comprises an AAV capsid protein and a polynucleotide cassette of the present invention. In some embodiments, the AAV capsid protein is a wild type AAV capsid protein. In other embodiments, the AAV capsid protein is a variant AAV capsid protein, wherein the variant capsid protein contains a substitution, deletion, or an insertion of one or more amino acids relative to the parental capsid protein or the capsid protein from which it is derived. For example, in one embodiment from about 5 to about 11 amino acids are inserted in an insertion site in the GH loop or loop IV of the VP1 capsid protein relative to a corresponding parental AAV capsid protein. Suitable examples include AAV variant capsids having the 7m8 variant capsid protein or a capsid protein that is derived from the AAV variant 7m8 capsid protein. In one particular example, the variant AAV comprises the AAV2.7m8 capsid protein.

In some aspects of the invention, pharmaceutical compositions are provided comprising a polynucleotide cassette of the invention and a pharmaceutically acceptable excipient. In some embodiments, the pharmaceutical composition comprises a gene delivery vector of the invention and a pharmaceutical excipient.

One embodiment is an isolated host cell transfected or transduced with a polynucleotide cassette of the present invention.

In some aspects of the invention, methods are provided for expressing a transgene in mammalian cells in vitro or in vivo, the method comprising contacting one or more mammalian cells, in vivo or in vitro, with an amount of a polynucleotide cassette, gene delivery vector, or pharmaceutical composition of the invention, wherein the transgene is expressed at detectable levels in the one or more mammalian cells, or, more preferably, is expressed at a level that is about 2-fold, 5-fold, or 10-fold higher than that obtained from (i.e., as compared to the expression of the transgene from) a reference CMV cassette comprising, in 5' to 3' order, a CMV enhancer sequence (SEQ ID NO:2), a CMV promoter (SEQ ID NO:21), a chimeric intron (SEQ ID NO:22), a 5'UTR (SEQ ID NO:23), the transgene or coding sequence of interest, a 3'UTR (SEQ ID NO:25), and an SV40 polyA sequence (SEQ ID NO:26), in the cells or cell culture, measured under the same conditions (i.e., other variables remaining constant). Some embodiments provide a method for expressing a transgene in mammalian cells in vitro or in vivo, comprising contacting one or more mammalian cells in vitro or in vivo with an amount of recombinant virus of the present invention, wherein the recombinant virus comprises a polynucleotide cassette according to the present disclosure. In preferred embodiments the cassette or transgene encodes a secretory protein (also referred to herein as a secretory polypeptide) and the secretory protein is expressed in the one or more mammalian cells at a level that is at least 2×, 5×, 10×, from about 5× to about 10×, or greater than 20× higher than that obtained by contacting the cells with a recombinant virus comprising the CMV reference control cassette encoding the same protein. In some aspects, the mammalian cells are contacted with an amount of polynucleotide cassette, pharmaceutical composition, or vector effective for altering one or more characteristics of the cell or for reducing one or more signs or symptoms of a disease in an individual.

In some aspects of the invention, methods are provided for the treatment or prophylaxis of a disease or disorder in a mammal in need of treatment or prophylaxis for a disease or disorder. In some embodiments, the method comprises administering to the mammal an effective amount of a pharmaceutical composition of the invention, wherein the coding sequence encodes a therapeutic gene product. In one embodiment the disease is an ocular disease and/or is a disease associated with a loss of function of or deficiency in a cellular protein product. In one embodiment, the ocular disease is associated with or caused by ocular neovascularization. One embodiment is a method for treating an ocular disease in a mammal in need thereof, comprising administering to the eye of a mammal in need of treatment a therapeutically effective amount of a pharmaceutical composition of the invention. In a more specific embodiment, a therapeutically effective amount of a pharmaceutical composition of the invention is administered to an eye of the individual in need of treatment by way of intraocular injection or by way of intravitreal injection.

Ocular diseases for which the subject cassettes, compositions, and methods may find use include acute macular neuroretinopathy; Behcet's disease; choroidal neovascularization; diabetic uveitis; histoplasmosis; macular degeneration, such as acute macular degeneration, non-exudative age related macular degeneration, and exudative age related macular degeneration; edema, such as macular edema, cystoid macular edema and diabetic macular edema; multifocal choroiditis; ocular trauma which affects a posterior ocular site or location; ocular tumors; retinal disorders, such as retinal vein occlusion, central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIG. 1 shows a series of polynucleotide cassettes constructed for assessment of transgene expression. The regulatory elements and coding sequence (i.e., gene) present in each cassette are listed from left to right in 5' to 3' order. Cassettes are identified by Cassette No. For example, Cassette No. 11 may be referred to as Cassette No. 11, Cassette 11, or simply C11.

DETAILED DESCRIPTION OF THE INVENTION

Figure 2:
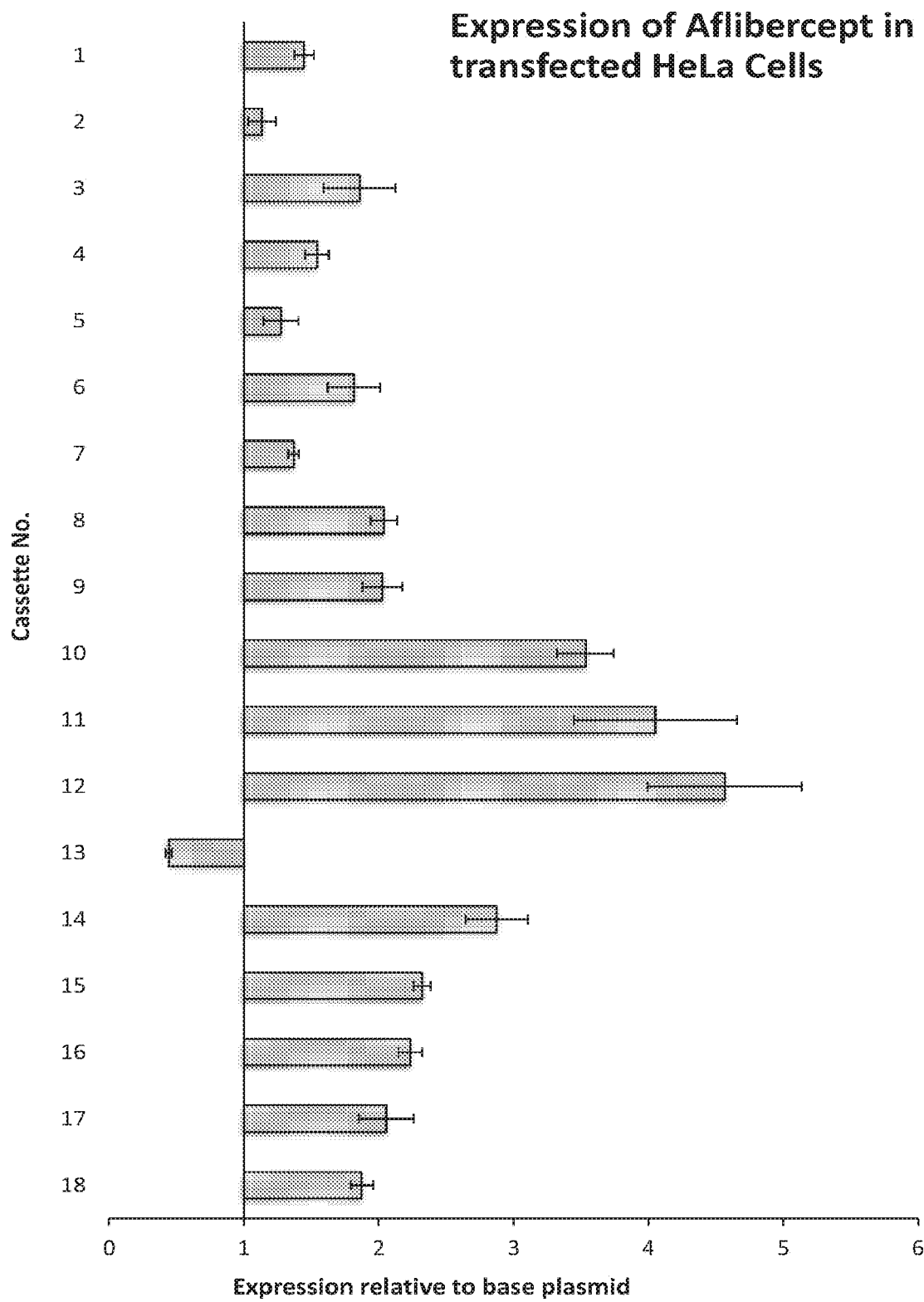
FIG. 2 shows a chart comparing the expression of aflibercept, a secreted protein, by the polynucleotide cassettes following transfection into HeLa cells. The expression level is plotted relative to that obtained from the "base plasmid," which is described in FIG. 1.

The present disclosure provides polynucleotide cassettes and expression vectors for the expression of a gene in cells. Also provided are pharmaceutical compositions and methods for the use of any of the compositions in promoting the expression of a gene in cells, for example, in an individual, e.g. for the treatment or prophylaxis of a disorder. These and other objects, advantages, and features of the invention will become apparent to those persons skilled in the art upon reading the details of the compositions and methods as more fully described below.

Definitions

A "non-naturally occurring" polynucleotide cassette is one that is not found in nature.

A "secretory protein" or "secretory polypeptide" also referred to herein as a "secreted protein" is any protein that is secreted by or exported from a living cell. One non-limiting example of a secretory protein for use with the presently described polynucleotide cassettes is sFLT-1.

The terms "disease," "disorder," and "medical condition" are synonymous and used interchangeably herein.

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors (i.e., viruses such as adeno-associated viruses), liposomes, and other gene delivery vehicles.

The term "AAV" is an abbreviation for adeno-associated virus, and may be used to refer to the virus itself or derivatives thereof. The term covers all subtypes and both naturally occurring and recombinant forms, except where required otherwise. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "AAV virus" or "AAV viral particle" or "rAAV vector particle" refers to a viral particle composed of at least one AAV capsid protein (typically by all of the capsid proteins of a wild-type AAV) and an encapsidated polynucleotide. If the particle comprises a heterologous polynucleotide (i.e. a polynucleotide other than a wild-type AAV genome such as a transgene to be delivered to a mammalian cell), it is typically referred to as a recombinant AAV vector, or rAAV. In general, the heterologous polynucleotide is flanked by AAV inverted terminal repeat sequences (ITRs).

The term "replication defective" as used herein relative to an AAV viral vector of the invention means the AAV vector cannot independently replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate further.

An "AAV variant" or "AAV mutant" as used herein refers to a viral particle composed of a variant AAV capsid protein, where the variant AAV capsid protein comprises at least one amino acid difference (e.g., amino acid substitution, amino acid insertion, amino acid deletion) relative to a corresponding parental AAV capsid protein, and where the variant capsid protein confers increased infectivity of a retinal cell compared to the infectivity of the retinal cell by an AAV virion comprising the corresponding parental AAV capsid protein, where the AAV capsid protein does not comprise an amino acid sequence present in a naturally occurring AAV capsid protein. A polynucleotide expression cassette of the present disclosure can be packaged in a variant AAV particle to promote delivery of the cassette to a specific cell type (e.g., retinal cells) in a target tissue.

As used herein, the term "gene" or "coding sequence" refers to a nucleotide sequence that encodes a gene product in vitro or in vivo. The term "transgene" refers to a coding sequence or a gene that is delivered into a cell by a vector. The coding sequence or gene can encode a peptide or polypeptide molecule.

As used herein, a "therapeutic gene" and "therapeutic protein" refers to a gene or protein that, when expressed, confers a beneficial effect on the cell or tissue in which it is present, or on a mammal in which the gene or protein is expressed. Examples of beneficial effects can be the reduction or amelioration of a sign or symptom of a condition or disease, the prevention or inhibition of a condition or disease, or conferral of a desired characteristic. Therapeutic genes and proteins include genes and proteins that correct a genetic deficiency in a cell or mammal.

A "therapeutically effective amount" or "effective amount" of a polynucleotide cassette, recombinant virus, or pharmaceutical composition of the present invention is an amount sufficient to result in the reduction of one or more signs or symptoms of a disease or medical condition in a subject, wherein the subject can be a human or non-human mammal.

As used herein, the term "gene product" refers to the desired expression product of a polynucleotide sequence such as a peptide or protein.

As used herein, the terms "polypeptide" and "protein" refer to polymers of amino acids of any length. The term "peptide" refers to a polymer of amino acids of about 50 or fewer amino acids. The terms also encompass an amino acid polymer that has been modified, as by for example, disulfide bond formation, glycosylation, lipidation, or phosphorylation. In some instances, a subject polypeptide may have a length of greater than 50 amino acids.

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a therapeutic polypeptide operably linked to a promoter, and a polyadenylation sequence consists only of the promoter, polynucleotide sequence encoding the therapeutic polypeptide, and polyadenlyation sequence. As another example, a polypeptide "consisting of" a recited sequence contains only the recited sequence.

An "expression vector" as used herein encompasses a vector, e.g. plasmid, minicircle, viral vector, liposome, and the like, comprising a subject polynucleotide cassette which encodes a gene product of interest, and is used for delivering the subject polynucleotide to an intended target cell.

A "promoter" as used herein encompasses a DNA sequence that directs the binding of RNA polymerase and thereby promotes RNA synthesis. Promoters and corresponding protein or polypeptide expression may be ubiquitous, meaning strongly active in a wide range of cells, tissues and species or cell-type specific, tissue-specific, or species specific. Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

An "enhancer" as used herein encompasses a cis-acting element that stimulates or inhibits transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "polyadenylation signal sequence" as used herein encompasses a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

As used herein, the term "operably linked" refers to a juxtaposition of genetic elements, e.g. promoter, enhancer, termination signal sequence, polyadenylation sequence, etc., wherein the elements are in a relationship permitting them to operate in the expected manner. For instance, a promoter is operably linked to a coding region if the promoter helps initiate transcription of the coding sequence. There may be intervening residues between the promoter and coding region so long as this functional relationship is maintained.

As used herein, the term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. As another example, a promoter removed from its native coding sequence and operably linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The term "endogenous" as used herein with reference to a nucleotide molecule or gene product refers to a nucleic acid sequence, e.g. gene or genetic element, or gene product, e.g. RNA, protein, that is naturally occurring in or associated with a host virus or cell.

The term "native" as used herein refers to a nucleotide sequence, e.g. gene, or gene product, e.g. RNA, protein, that is present in a wildtype virus or cell.

The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a polypeptide variant comprises at least one amino acid difference (e.g., amino acid substitution, amino acid insertion, amino acid deletion) relative to a reference polypeptide sequence, e.g. a native polypeptide sequence, and a polynucleotide variant comprises at least one nucleotide or nucleoside difference (e.g., nucleotide or nucleoside substitution, insertion, or deletion) relative to a reference polynucleotide sequence, e.g., a native polynucleotide sequence.

As used herein, the term "sequence identity" or "percent identity," refers to the degree of identity between two or more polynucleotides when aligned using a nucleotide sequence alignment program; or between two or more polypeptide sequences when aligned using an amino acid sequence alignment program. Similarly, the term "identical" or percent "identity" when used herein in the context of two or more nucleotide or amino acid sequences refers to two sequences that are the same or have a specified percentage of amino acid residues or nucleotides when compared and aligned for maximum correspondence, for example as measured using a sequence comparison algorithm, e.g. the Smith-Waterman algorithm, etc., or by visual inspection. For example, the percent identity between two amino acid sequences may be determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. As another example, the percent identity between two nucleotide sequences may be determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, Nucleic Acids Res, 25: 3389-3402). When utilizing BLAST and Gapped BLAST programs, the default parameters of the respective programs (e.g., XBLAST and NBLAST) can be used.

As used herein, the terms "biological activity" and "biologically active" refer to the activity attributed to a particular biological element in a cell. For example, the "biological activity" of an "immunoglobulin", "antibody" or fragment or variant thereof refers to the ability to bind an antigenic determinant and thereby facilitate immunological function. As another example, the biological activity of a polypeptide or functional fragment or variant thereof refers to the ability of the polypeptide or functional fragment or variant thereof to carry out its native functions of, e.g., binding, enzymatic activity, etc. As a third example, the biological activity of a gene regulatory element, e.g. promoter, enhancer, kozak sequence, and the like, refers to the ability of the regulatory element or functional fragment or variant thereof to regulate, i.e. promote, enhance, or activate the translation of, respectively, the expression of the gene to which it is operably linked.

The terms "administering" or "introducing", as used herein, refer to delivery of a vector for recombinant protein expression to a cell, to cells and/or organs of a subject, or to a subject. Such administering or introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); or by infection or transduction which typically refers to the introduction of a nucleic acid molecule into a cell by way of an infectious agent, i.e. a virus or viral vector.

Typically, a cell is referred to as "transduced", "infected", "transfected" or "transformed" depending on the means used for administration, introduction or insertion of heterologous DNA (i.e., the vector) into the cell. A cell is transduced with exogenous or heterologous DNA when the DNA is introduced into the cell by a virus or viral vector. A cell is transfected with exogenous or heterologous DNA when the DNA is introduced into the cell by a non-viral method. Non-viral methods include both chemical (e.g., lipofection) and non-chemical methods. The terms "transduced" and "infected" are used interchangeably herein to refer to cells that have received a heterologous DNA or heterologous polynucleotide from a virus or viral vector.

The term "host cell", as used herein refers to a cell that has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The terms "treatment" and "treating" refer to the reduction of one or more signs or symptoms of a disease or disorder.

"Ocular disease" means a disease, ailment, or condition that affects or involves the eye or one or the parts or regions of the eye. As such, ocular diseases include retinal diseases, or diseases that affect the light-sensitive layer of tissue in the back of the eye. The eye includes the eyeball and the tissues and fluids which constitute the eyeball, the periocular muscles (such as the oblique and rectus muscles) and the portion of the optic nerve which is within or adjacent to the eyeball.

A tissue "explant" is a piece of tissue that has been transferred from an animal to a nutrient medium.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" or "approximately" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing-herein is to be construed as an admission that the present invention is not entitled to antedate such publication by virtue of prior invention. Further, the dates of publication provided may be different from the actual publication dates which may need to be independently confirmed.

Unless otherwise indicated, all terms used herein have the same meaning as they would to one skilled in the art and the practice of the present invention will employ, conventional techniques of microbiology and recombinant DNA technology, which are within the knowledge of those of skill of the art.

Compositions

In some aspects of the disclosure, compositions are provided for the expression of a transgene in a eukaryotic cell(s). In some aspects, the eukaryotic cell is a mammalian cell. In some aspects, the mammalian cell is a retinal cell, such as a retinal ganglion cell, amacrine cell, horizontal cell, bipolar cell, photoreceptor cell, cone cell, rod cell, Müller glial cell, or retinal pigmented epithelium.

In some embodiments of the disclosure, the composition is a polynucleotide cassette. By a "polynucleotide cassette" is meant a polynucleotide sequence comprising two or more functional polynucleotide sequences, e.g. regulatory elements, translation initiation sequences, coding sequences, termination sequences, etc., typically in operable linkage to one another. Generally, a subject polynucleotide sequence is composed of DNA. Likewise, by a "polynucleotide cassette for the expression of a transgene in a mammalian cell," it is meant a combination of two or more functional polynucleotide sequences, e.g. promoter, enhancer, 5'UTR, translation initiation sequence, coding sequence, termination sequences, etc. that promotes the expression of the transgene in a cell.

For example, in some embodiments, the polynucleotide cassette comprises: in 5' to 3' order: (a) optionally, a first enhancer region; (b) a promoter region, wherein the promoter region is specific for eukaryotic cells; (c) a coding sequence encoding a polypeptide gene product; (d) a second enhancer region; and (e) a polyadenylation site. In still other embodiments, the polynucleotide cassette further comprises a 5'untranslated region (5'UTR) upstream of the coding sequence. In yet other embodiments, the polynucleotide cassette further comprises an intron region downstream of the promoter and upstream of the coding sequence. In other embodiments, the polynucleotide cassette further comprises an RNA export signal downstream of the second enhancer and upstream of the polyadenylation site. In regard to the polynucleotide cassettes disclosed herein, the coding sequence is understood to be operably linked to the expression control sequences in the cassette. For example, the coding sequence is operably linked to the promoter region, enhancer region(s), and the polyadenylation site.

In some embodiments, the polynucleotide cassettes of the present disclosure provide for enhanced expression of a transgene in mammalian cells. In certain embodiments, the arrangement of the two or more functional polynucleotide sequences within the polynucleotide cassettes of the present disclosure provide for enhanced expression of a transgene in mammalian cells. By "enhanced" it is meant that expression of the transgene is increased, augmented, or stronger, in cells carrying the polynucleotide cassettes of the present disclosure relative to cells carrying the transgene operably linked to comparable regulatory elements. Put another way, expression of the transgene is increased, augmented, or stronger, from the polynucleotide cassettes of the present disclosure relative to expression from a polynucleotide cassette not comprising the one or more optimized elements of the present disclosure, i.e. a reference control cassette, such as the CMV reference control cassette described herein. In certain embodiments, the enhanced expression is specific for or limited to one or more desired cell types. In one embodiment the transgene encodes a protein that is secreted by the cell into the aqueous environment surrounding the cell.

For example, expression of the transgene may be enhanced, or augmented, or stronger, in cells comprising a polynucleotide cassette comprising a promoter disclosed herein than in cells that carry the transgene operably linked to a different promoter. As another example, expression of the transgene may be enhanced, or increased, augmented, or stronger, in cells comprising a polynucleotide cassette comprising an enhancer sequence disclosed herein than in cells that carry the transgene operably linked to a different enhancer sequence. As another example, expression of the transgene may be enhanced, or increased, augmented, or stronger, in cells comprising a polynucleotide cassette encoding a 5'UTR disclosed herein than in cells that carry the transgene operably linked to a different 5'UTR coding sequence. As another example, expression of the transgene may be enhanced, or increased, augmented, or stronger, in cells comprising a polynucleotide cassette comprising an intron as disclosed herein than in cells that carry the transgene operably linked to a different intronic sequence. In yet another example, expression of the transgene may be enhanced, or increased, augmented, or stronger, in cells comprising a polynucleotide cassette comprising an intron as disclosed herein than in cells that carry the transgene operably linked to a reference control cassette such as the CMV reference control cassette disclosed herein.

In preferred embodiments, the polynucleotide expression cassette promotes expression (or a higher level of expression as compared to a reference cassette) of the transgene in one or more particular cell or tissue types in vitro an in vivo. Examples of cell types include but are not limited to HeLa cells, HEK-293 cells, ARPE-19 cells (a human retinal pigment epithelial cell line), retinal ganglion cells, amacrine cells, horizontal cells, bipolar cells, photoreceptor cells, cone cells, rod cells, Müller glial cells, and retinal pigmented epithelium. In another embodiment, enhanced expression is observed in cells in a retinal tissue explant.

In some embodiments, the expression of a secretory polypeptide from the polynucleotide cassette in mammalian cells is at least about 2×, 3×, 5×, 9×, 10×, 20×, or 50× higher than the expression of the secretory polypeptide from a reference cassette in the mammalian cells in vitro or in vivo. More generally, the expression of the secretory polypeptide is 2 to 10×, 5 to 10×, 9 to 10×, at least 2×, at least 5×, or at least 10× higher than the expression of the polypeptide from a reference cassette in mammalian cells. Stated in other terms, the polynucleotide cassette expresses the secretory protein in a mammalian cell culture at a level that is at least or that is more than 2-fold, 5-fold, 10-fold, 50-fold or from about 5 to about 10 fold higher than that obtained from the reference cassette in the mammalian cell culture (e.g., in a duplicate mammalian cell culture).

Without wishing to be bound by theory, enhanced expression of a transgene in cells or outside cells in the extracellular environment (e.g., culture supernatant or tissue matrix) is believed to be due to a faster build-up of gene product in the cells or a more stable gene product in the cells. Thus, enhanced expression of a transgene by the polynucleotide cassettes of the subject disclosure may be observed in a number of ways. For example, enhanced expression may be observed by detecting the expression of the transgene following contact of the polynucleotide cassette to the cells sooner, e.g. 7 days sooner, 2 weeks sooner, 3 weeks sooner, 4 weeks sooner, 8 weeks sooner, 12 weeks sooner, or more, than expression would be detected if the transgene were operably linked to comparable regulatory elements, such as those in the CMV reference control cassette described herein. Enhanced expression may also be observed as an increase in the amount of gene product per cell. For example, there may be a 2-fold increase or more, e.g. a 3-fold increase or more, a 4-fold increase or more, a 5-fold increase or more, or a 10-fold increase or more in the amount of gene product per mammalian cell. Enhanced expression may also be observed as an increase in the number of mammalian cells that express detectable levels of the transgene carried by the polynucleotide cassette. For example, there may be a 2-fold increase or more, e.g. a 3-fold increase or more, a 4-fold increase or more, a 5-fold increase or more, or a 10-fold increase or more in the number of mammalian cells that express detectable levels of the transgene. As another example, the polynucleotide of the present invention may promote detectable levels of the transgene in a greater percentage of cells as compared to a conventional polynucleotide cassette; for example, where a conventional cassette may promote detectable levels of transgene expression in, for example, less than 5% of the cells in a certain region, the polynucleotide of the present invention promotes detectable levels of expression in 5% or more of the cells in that region; e.g. 10% or more, 15% or more, 20% or more, 25% or more, 30% or more, 35% or more, 40% or more, or 45% or more, in some instances 50% or more, 55% or more; 60% or more, 65% or more, 70% or more, or 75% or more, for example 80% or more, 85% or more, 90% or more, or 95% or more of the cells that are contacted, will express detectable levels of gene product. Enhanced expression may also be observed as an alteration in the viability and/or function of the cells.

The polynucleotide cassettes of the present disclosure typically comprise a promoter region. In certain embodiments, the promoter region promotes expression of a coding sequence in mammalian cells. In some instances, the promoter is a ubiquitous promoter, i.e., it is a promoter that is active in a wide range of cells, tissues and species. Suitable examples include the actin, cytomegalovirus (CMV), elongation factor 1 alpha (EF1a), and glyceraldehyde 3-phosphate dehydrogenase (GAPDH) promoters.

In some embodiments, the polynucleotide comprises one or more enhancers. Enhancers are nucleic acid elements that enhance transcription. In some embodiments, the polynucleotide cassette comprises a first enhancer upstream of the coding sequence and a second enhancer downstream of the coding sequence. Exemplary suitable enhancers include but are not limited to EF1a, CMV, the full EES or a portion thereof such as the 410-564 EES or 511-810 EES. EES (expression enhancer sequence) corresponds to a human scaffold-attachment region, or SAR, of human beta-interferon (Agarwal, M et al. (1998) "Scaffold Attachment Region-Mediated Enhancement of Retroviral Vector Expression in Primary T Cells" J. Virol. 72(5):3720-3728).

In certain embodiments, the upstream enhancer includes but is not limited to EF1a or CMV. In certain embodiments, the downstream enhancer includes but is not limited to the full expression enhancer sequence (full EES), 410-564 EES, or 511-810 EES.

In some embodiments, the subject polynucleotide cassette comprises a sequence encoding a 5' untranslated region, i.e. a polynucleotide sequence encoding an untranslated region 5' to the coding sequence, also called the 5'UTR. In some embodiments, the 5'UTR does not contain the polynucleotide ATG. Exemplary suitable 5'UTR sequences include but are not limited to sequences selected from i) the tripartite leader sequence from adenovirus (TPL) (Logan, J et al. (June 1984) "Adenovirus tripartite leader sequence enhances translation of mRNAs late after infection" Proc. Natl. Acad. Sci. USA 81: 3655-3659); ii) the enhancer element sequence from the adenovirus major late promoter (eMLP) (Durocher, Y et al. (2002) "High-level and high-throughput recombinant protein production by transient transfection of suspension-growing human 293-EBNA1 cells" Nucl. Acids. Res. 30(2):e9); iii) UTR1; and iv) UTR2. In a preferred embodiment, the 5'UTR comprises, in 5' to 3' order, a TPL and an eMLP sequence.

In some embodiments, the subject polynucleotide cassette further comprises an intron comprising a splice donor/acceptor region. In some embodiments, the intron is located downstream of the promoter region and is located upstream of the translation initiation sequence of the gene. Introns are DNA polynucleotides that are transcribed into RNA and removed during mRNA processing through intron splicing. Polynucleotide cassettes containing introns generally have higher expression than those without introns. Introns can stimulate expression between 2- and 500-fold (Buchman and Berg, 1988. Mol Cell Bio, 8(10): 4395). Efficiently spliced introns contain a pre-splice donor, branchpoint, and Py rich region (Senapathy et al, 1990; Meth. Enzymol. 183, 252-78; Wu and Krainer, 1999; Mol Cell Biol 19(5):3225-36). 5' introns are generally more efficient compared to introns at the 3' end (Huang and Gorman, 1990; Mol Cell Bio, 10:1805). Although introns are known generally to increase the level of gene expression, the specific increase (if any) of a given cDNA is empirical and must be tested; for example the chimeric intron in the pSI vector increases CAT expression by 21-fold, but luciferase expression by only 3-fold. Exemplary intron sequences include but are not limited to sequences from actin, elongation factor 1 alpha (EF1a), enhancer element from the adenovirus major late promoter (eMLP) and CMVc.

The coding sequence to be expressed in the cells can be any polynucleotide sequence, e.g. gene or cDNA that encodes a gene product, e.g. a polypeptide. The coding sequence may be heterologous to the promoter sequence and/or 5'UTR sequence to which it is operably linked, i.e. not naturally operably associated with it. Alternatively, the coding sequence may be endogenous to the promoter sequence and/or 5'UTR sequence to which it is operably linked, i.e. is associated in nature with that promoter or 5'UTR. The gene product may act intrinsically in the mammalian cell, or it may act extrinsically, e.g. it may be secreted. For example, when the transgene is a therapeutic gene, the coding sequence may be any gene that encodes a desired gene product or functional fragment or variant thereof that can be used as a therapeutic for treating a disease or disorder. Accordingly, the coding sequence in the polynucleotide cassette may encode, for example, an opsin protein or a protein that inhibits VEGF, or the polynucleotide may encode a protein or an enzyme effective for reducing one or more signs or symptoms of a disease.

In various preferred embodiments, the transgene encodes a peptide or protein that is secreted from the cell. In some embodiments, the secreted protein is a therapeutic protein, or a protein that is effective for the treatment of a disease in a subject. In some embodiments, the therapeutic protein is an anti-angiogenic polypeptide, or a polypeptide that inhibits the growth of new blood vessels (angiogenesis). In some forms, the secreted protein is an anti-VEGF protein, or a protein that inhibits vascular endothelial growth factor (VEGF). Examples of anti-VEGF proteins include ranibizumab, bevacizumab, and aflibercept. Another example of an anti-VEGF polypeptides is soluble fms-like tyrosine kinase-1 (sFLT-1). In other instances, the secreted protein comprises or consists of a VEGF-binding protein or functional fragment thereof such as any of those disclosed in U.S. Pat. Nos. 5,712,380, 5,861,484 and 7,071,159, or a VEGF-binding fusion protein as, for example, disclosed in U.S. Pat. No. 7,635,474. In some forms, the secreted protein comprises or consists of a single chain antibody, such as for example a single chain anti-VEGF antibody. According to one embodiment, the transgene encodes sFLT-1, and in a more specific embodiment, human sFLT-1. Alternatively, the transgene may comprise a sequence encoding a functional, VEGF-binding fragment of sFLT-1 (Wiesmann et al., 1997; Cell, 91: 695-704). According to another embodiment, the transgene encodes A1AT, or alpha-1 antitrypsin (Chiuchiolo et al., 2013, 24(4):161-173; Stoller and Aboussouan (2012) Am J Respir. Crit. Care Med. 185(3):246-59), which may find use in a method for treating a disease associated with A1AT deficiency.

sFLT-1 is a soluble truncated form of the VEGF receptor FLT-1 and is also known as soluble vascular endothelial growth factor receptor-1 (sVEGFR-1). Recombinant sFLT-1 binds and inhibits VEGF (Kendall and Thomas, 1993; *Proc Natl Acad Sci.* 90(22): 10705-10709). In nature, it is generated by alternative mRNA splicing and lacks the membrane-proximal immunoglobulin-like domain, the transmembrane spanning region and the intracellular tyrosine-kinase domain. As described herein, "soluble" FLT-1, or sFLT-1 refers to FLT-1 that is not restricted to the cellular membrane. Unbound sFLT-1 may diffuse freely in extracellular space or solution.

In one embodiment of the invention, the transgene coding sequence is modified, or "codon optimized" to enhance expression by replacing infrequently represented codons with more frequently represented codons. The coding sequence is the portion of the mRNA sequence that encodes the amino acids for translation. During translation, each of 61 trinucleotide codons are translated to one of 20 amino acids, leading to a degeneracy, or redundancy, in the genetic code. However, different cell types, and different animal species, utilize tRNAs (each bearing an anticodon) coding for the same amino acids at different frequencies. When a gene sequence contains codons that are infrequently represented by the corresponding tRNA, the ribosome translation machinery may slow, impeding efficient translation. Expression can be improved via "codon optimization" for a particular species, where the coding sequence is altered to encode the same protein sequence, but utilizing codons that are highly represented, and/or utilized by highly expressed human proteins (Cid-Arregui et al., 2003; J. Virol. 77: 4928). In one aspect, the coding sequence is optimized for translation in primates. In one aspect of the present invention, the coding sequence of the transgene is modified to replace codons infrequently expressed in mammal or in primates with codons frequently expressed in primates. For example, in some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% identity, at least 99% identity, wherein at least one codon of the coding sequence has a higher tRNA frequency in humans than the corresponding codon in the sequence disclosed above or herein.

In some embodiments, the polynucleotide cassette of the present invention further comprises an RNA export signal. An RNA export signal is a cis-acting post-transcriptional regulatory element that enhances export of the RNA from the nucleus. Exemplary RNA export sequences include but are not limited to sequences from the hepatitis B virus post-transcriptional regulatory element (HPRE) and the woodchuck hepatitis virus post-transcriptional element (WPRE) (Higashimoto, T et al. "The woodchuck hepatitis virus post-transcriptional regulatory element reduces read-through transcription from retroviral vectors" *Gene Ther.*, September 2007, 14(17):1298-1304).

In some embodiments, the polynucleotide cassette of the present invention further comprises a polyadenylation region. As is understood in the art, RNA polymerase II transcripts are terminated by cleavage and addition of a polyadenylation region, which may also be referred to as a poly(A) signal, poly(A) region, or poly(A) tail. The poly A region contains multiple consecutive adenosine monophosphates, often with repeats of the motif AAUAAA. Several efficient polyadenylation sites have been identified, including those from SV40, bovine growth hormone, human growth hormone and rabbit beta globin (Xu et al, 2001; Gene 272(1-2):149-156; Xu et al., 2002; J Control Rel. 81(1-2):155-163). The most efficient polyA signal for expression of a transgene in mammalian cells may depend on the cell type and species of interest and the particular vector used. In some embodiments of the invention, the polynucleotide cassette comprises a polyA region selected from the group consisting of bovine growth hormone (BGH), human growth hormone (HGH), and beta-globin (βglobin).

As will be appreciated by the ordinarily skilled artisan, two or more of the aforementioned polynucleotide elements may be combined to create the polynucleotide cassettes of the present disclosure. Thus, for example, the subject polynucleotide cassette may comprise in operable linkage from 5' to 3' order, a CMV enhancer, a CMV or EF1a promoter, optionally a CMVc or EF1α intron, a UTR1, UTR2, or TPL and eMLP 5'UTR, a coding sequence for sFLT1, or a secreted polypeptide, a full EES, 410-564 EES, or 511-810 EES enhancer, optionally an HPRE or WPRE RNA export sequence, and a BGH, HGH, or a βglobin polyadenylation signal sequence.

Another polynucleotide cassette may comprise in operable linkage from 5'to 3' order, a CMV enhancer, a CMV promoter, a 5'UTR comprising TPL and eMLP sequences, a coding sequence encoding a therapeutic agent (e.g., a therapeutic polypeptide), a full length EES enhancer, and an HGH polyA signal sequence. In particular embodiments, the coding sequence encodes an anti-angiogenic polypeptide. In particular embodiments, the coding sequence is codon optimized. In certain of these embodiments, the polynucleotide cassette comprises one or more sequences selected from SEQ ID NO: 76-80.

In yet another embodiment, the polynucleotide cassette may comprise in operable linkage from 5'to 3' order, a CMV enhancer, a CMV promoter, a 5'UTR comprising TPL and eMLP sequences, a coding sequence encoding a therapeutic agent, 410-564 EES enhancer, an HPRE RNA export region, and a BGH polyadenylation signal. In particular embodiments, the coding sequence encodes an anti-angiogenic polypeptide. In particular embodiments, the coding sequence is codon optimized. In certain of these embodiments, the polynucleotide cassette comprises one or more sequences selected from SEQ ID NO: 81-86.

In still another embodiment, polynucleotide cassette may comprise in operable linkage from 5'to 3' order, a CMV enhancer, an EF1α promoter, an EF1α intron, a UTR2 5'UTR, a coding sequence encoding a therapeutic agent, a 511-810 EES enhancer, an WPRE RNA export region, and a bovine growth hormone (BGH) polyadenylation signal. In particular embodiments, the coding sequence encodes an anti-angiogenic polypeptide. In particular embodiments, the coding sequence is codon optimized. In certain of these embodiments, the polynucleotide cassette comprises one or more sequences selected from SEQ ID NO: 70-75.

In yet another embodiment, the polynucleotide cassette may comprise in operable linkage from 5'to 3' order, a CMV enhancer, a CMV promoter, a CMVc intron, a UTR1 5'UTR, a coding sequence encoding a therapeutic agent, full length EES enhancer, an WPRE RNA export region, and a beta-globin (βglobin) polyadenylation signal. In particular embodiments, the coding sequence encodes an anti-angiogenic polypeptide. In particular embodiments, the coding sequence is codon optimized. In certain of these embodiments, the polynucleotide cassette comprises one or more sequences selected from SEQ ID NO: 92-95.

In yet another embodiment, the polynucleotide cassette may comprise in operable linkage from 5'to 3' order, a CMV enhancer, an actin promoter, anan eMLP intron, a coding sequence encoding a therapeutic agent, a 511-810 EES sequence, an HPRE RNA export sequence, and a Beta Globin polyadenylation signal. In particular embodiments, the coding sequence encodes an anti-angiogenic polypeptide. In particular embodiments, the coding sequence is codon optimized. In certain of these embodiments, the polynucleotide cassette comprises one or more sequences selected from SEQ ID NO: 87-91.

In yet another embodiment, the polynucleotide cassette may comprise in operable linkage from 5'to 3' order, a CMV enhancer an actin promoter, a chicken beta-actin intron, a UTR1 5'UTR, a coding sequence encoding a therapeutic agent, a 410-564 EES sequence, an HPRE RNA export sequence, and a BGH polyadenylation site. In particular embodiments, the coding sequence encodes an anti-angiogenic polypeptide. In particular embodiments, the coding sequence is codon optimized. In certain of these embodiments, the polynucleotide cassette comprises one or more sequences selected from SEQ ID NO: 92-95.

As will be recognized by one of ordinary skill in the art, the polynucleotide cassettes may optionally contain other elements including, but not limited to restriction sites to facilitate cloning and regulatory elements for a particular gene expression vector. Examples of regulatory sequence include ITRs for AAV vectors, bacterial sequences for plasmid vectors, attP or attB sites for phage integrase vectors, and transposable elements for transposons.

As disclosed herein, in some aspects of the present invention, the subject polynucleotide cassettes are used to deliver a gene to cells of an animal, e.g. to determine the effect that the gene has on cell viability and/or function, to treat a cell disorder, etc. Accordingly, in some aspects of the invention, the composition that provides for the expression of a transgene in mammalian cells is a gene delivery vector, wherein the gene delivery vector comprises a polynucleotide cassette of the present disclosure.

Any convenient gene delivery vector that finds use delivering polynucleotide sequences to mammalian cells is encompassed by the gene delivery vectors of the present disclosure. For example, the vector may comprise single or double stranded nucleic acid, e.g. single stranded or double stranded DNA. For example, the gene delivery vector may be DNA, e.g., a naked DNA, e.g. a plasmid, or a minicircle, etc. The vector may comprise single-stranded or double-stranded RNA, including modified forms of RNA. In another example, the gene delivery vector may be an RNA, e.g., an mRNA or modified mRNA.

As another example, the gene delivery vector may be a viral vector derived from a virus, e.g. an adenovirus, an adeno-associated virus (AAV), a lentivirus, a herpes virus, an alpha virus or a retrovirus, e.g., Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) or lentivirus. While embodiments encompassing the use of adeno-associated virus are described in greater detail below, it is expected that the ordinarily skilled artisan will appreciate that similar knowledge and skill in the art can be brought to bear on non-AAV gene delivery vectors as well. See, for example, the discussion of retroviral vectors in, e.g., U.S. Pat. Nos. 7,585,676 and 8,900,858, and the discussion of adenoviral vectors in, e.g. U.S. Pat. No. 7,858,367, the full disclosures of which are incorporated herein by reference.

In some embodiments, the gene delivery vector is a recombinant adeno-associated virus (rAAV). In such embodiments, the subject polynucleotide cassette is flanked on the 5' and 3' ends by functional AAV inverted terminal repeat (ITR) sequences. By "functional AAV ITR sequences" is meant that the ITR sequences function as intended for the rescue, replication and packaging of the AAV virion. Hence, AAV ITRs for use in the gene delivery vectors of the invention need not have a wild-type nucleotide sequence, and may be altered by the insertion, deletion or substitution of nucleotides or the AAV ITRs may be derived from any of several AAV serotypes, e.g. AAV1, AAV2, AAV3, AAV4, AAV5, AAV6, AAV7, AAV8, AAV9, AAV10. Preferred AAV vectors have the wild type Rep and Cap genes deleted in whole or part, but retain functional flanking ITR sequences. In particular embodiments, the AAV viral vector is the AAV2 variant 7m8.

In some embodiments, the subject polynucleotide cassette is encapsidated within an AAV capsid, which may be derived from any adeno-associated virus serotype, including without limitation, AAV1, AAV2, AAV3, AAV4, AAV5, AAV6, AAV7, AAV8, AAV9, AAV10, etc, any of which may serve as the gene delivery vector. For example, the AAV capsid may be a wild type, or native, capsid. Wild type AAV capsids of particular interest include AAV2, AAV5, and AAV9. However, as with the ITRs, the capsid need not have a wild-type nucleotide sequence, but rather may be altered relative to the wild-type sequence by the insertion, deletion or substitution of nucleotides in the VP1, VP2 or VP3 sequence, so long as the capsid is able to transduce mammalian cells. Put another way, the AAV capsid may be a variant AAV capsid, which comprises one or more amino acid substitutions, deletions, or insertions relative to the parental capsid protein or AAV capsid protein from which it is derived. Variant AAVs of particular interest include those disclosed in U.S. Pat. No. 9,193,956, the full disclosure of which is incorporated by reference herein. In some embodiments, the variant AAV comprises the 7m8 variant capsid protein (which may be referred to herein as AAV2.7m8 or 7m8.AAV2), disclosed in U.S. Pat. No. 9,193,956. In other embodiments the AAV comprises or consists of the AAV2.5T capsid protein provided in U.S. Pat. No. 9,233,131 as SEQ ID NO:42. In certain embodiments, the AAV comprises the AAVShH10 or AAV6 capsid protein. FIGS. 8A-8C of U.S. Patent Application Publication No. 20120164106 show the amino acid sequence of the AAVShH10 capsid protein, which is also described in Klimczak, R. R. et al., PLOS One 4(10):e7467 (Oct. 14, 2009).

Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

Gene delivery vectors (e.g., rAAV virions) encapsulating the polynucleotide cassettes of the present disclosure may be produced using standard methodology. For example, in the case of rAAV virions, an AAV expression vector according to the invention may be introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

Any concentration of viral particles suitable to effectively transduce mammalian cells can be prepared for contacting mammalian cells in vitro or in vivo. For example, the viral particles may be formulated at a concentration of $10^8$ vector genomes per mL (vg/mL) or more, for example, $5 \times 10^8$ vector genomes per mL; $10^9$ vector genomes per mL; $5 \times 10^9$ vector genomes per mL, $10^{10}$ vector genomes per mL, $5 \times 10^{10}$ vector genomes per mL; $10^{11}$ vector genomes per mL; $5 \times 10^{11}$ vector genomes per mL; $10^{12}$ vector genomes per mL; $5 \times 10^{12}$ vector genomes per mL; $10^{13}$ vector genomes per mL; $1.5 \times 10^{13}$ vector genomes per mL; $3 \times 10^{13}$ vector genomes per mL; $5 \times 10^{13}$ vector genomes per mL; $7.5 \times 10^{13}$ vector genomes per mL; $9 \times 10^{13}$ vector genomes per mL; $1 \times 10^{14}$ vector genomes per mL, $5 \times 10^{14}$ vector genomes per mL or more, but typically not more than $1 \times 10^{15}$ vector genomes per mL. Similarly, any total number of viral particles suitable to provide appropriate transduction of cells to confer the desired effect or treat the disease can be administered to the mammal. In various preferred embodiments, at least $10^8$; $5 \times 10^8$; $10^9$; $5 \times 10^9$, $10^{10}$; $5 \times 10^{10}$; $10^{11}$; $5 \times 10^{11}$; $10^{12}$; $5 \times 10^{12}$; $10^{13}$; $1.5 \times 10^{13}$; $3 \times 10^{13}$; $5 \times 10^{13}$; $7.5 \times 10^{13}$; $9 \times 10^{13}$, $1 \times 10^{14}$ viral particles, or $5 \times 10^{14}$ viral particles or more, but typically not more than $1 \times 10^{15}$ viral particles are injected per eye. Any suitable number of administrations of the vector to the mammal or the primate eye can be made. In one embodiment, the methods comprise a single administration; in other embodiments, multiple administrations are made over time as deemed appropriate by an attending clinician.

The subject viral vector may be formulated into a pharmaceutical composition comprising any suitable unit dose of the vector, which can be administered to a subject to produce a change in the subject or to treat a disease in the subject. In some embodiments a unit dose comprises, without limitation, $1 \times 10^8$ vector genomes of the viral vector or more, for example at least about $1 \times 10^9$, $1 \times 10^{10}$, $1 \times 10^{11}$, $1 \times 10^{12}$, $1 \times 10^{13}$, $1 \times 10^{14}$, or at least about $3 \times 10^{14}$ vector genomes or more, in certain instances, at least about $1 \times 10^{14}$ vector genomes, but usually no more than $4 \times 10^{15}$ vector genomes. In some cases, the unit dose comprises at most about $5 \times 10^{15}$ vector genomes, e.g. $1 \times 10^{14}$ or $5 \times 10^{14}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes or less, and typically no less than $1 \times 10^8$ vector genomes. In some cases, the unit dose comprises $1 \times 10^{10}$ to $1 \times 10^{11}$ vector genomes. In some cases, the unit dose comprises $1 \times 10^{10}$ to $3 \times 10^{12}$ vector genomes. In some cases, the unit dose comprises $1 \times 10^9$ to $3 \times 10^{13}$ vector genomes. In some cases, the unit dose comprises $1 \times 10^8$ to $3 \times 10^{14}$ vector genomes. In some cases the unit dose comprises from about $1 \times 10^{10}$ to about $5 \times 10^{14}$ vector genomes.

In some cases, the unit dose of a pharmaceutical composition may be measured using multiplicity of infection (MOI). By MOI it is meant the ratio, or multiple, of vector or viral genomes to the cells to which the nucleic acid may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI.

In some aspects, the amount of pharmaceutical composition comprises about $1 \times 10^8$ to about $1 \times 10^{15}$ recombinant viruses, about $1 \times 10^9$ to about $1 \times 10^{14}$ recombinant viruses, about $1 \times 10^{10}$ to about $1 \times 10^{13}$ recombinant viruses, or about $1 \times 10^{11}$ to about $3 \times 10^{12}$ recombinant viruses.

In preparing the subject rAAV compositions, any host cells for producing rAAV virions may be employed, including, for example, mammalian cells (e.g. 293 cells), insect cells (e.g. SF9 cells), microorganisms and yeast. Host cells can also be packaging cells in which the AAV rep and cap genes are stably maintained in the host cell or producer cells in which the AAV vector genome is stably maintained and packaged. Exemplary packaging and producer cells are derived from SF-9, 293, A549 or HeLa cells. AAV vectors are purified and formulated using standard techniques known in the art.

The present invention includes pharmaceutical compositions comprising a polynucleotide cassette or gene delivery vector described herein and a pharmaceutically-acceptable carrier, diluent or excipient. For example, one embodiment is a pharmaceutical composition comprising a recombinant virus comprising a polynucleotide of the present disclosure and a pharmaceutically acceptable excipient. In a specific embodiment, the recombinant virus is a recombinant adeno-associated virus (AAV). The subject polynucleotide cassettes or gene delivery vector can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile.

For instances in which cone cells are to be contacted in vivo, the subject polynucleotide cassettes or gene delivery vectors comprising the subject polynucleotide cassette can be treated as appropriate for delivery to the eye.

Pharmaceutical compositions suitable for use in the present invention further include sterile aqueous solutions or dispersions and sterile powders for the extemporaneous preparation of sterile injectable solutions or dispersion. Thus, the pharmaceutical composition can be in the form of a sterile injectable solution. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the compositions are prepared with carriers that will protect the gene cassette or expression vector against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral, ocular or parenteral compositions in dose unit form for ease of administration and uniformity of dose. Dose unit form as used herein refers to physically discrete units suited as unitary doses for the subject to be treated; each unit containing a predetermined quantity of gene delivery vector or polynucleotide cassette calculated to produce the desired therapeutic effect in association with the required pharmaceutical carrier. The specification for the dose unit forms of the invention are dictated by the unique characteristics of the gene delivery vector, polynucleotide cassette, and the particular therapeutic effect to be achieved.

The pharmaceutical compositions can be included in a container, pack, or dispenser, e.g. syringe, e.g. a prefilled syringe, together with instructions for administration.

By "pharmaceutically acceptable excipient" is meant a material, substance, diluent, or carrier that is substantially non-toxic to the cells or subject to which it is administered. That is, the pharmaceutically acceptable excipient may be incorporated into a pharmaceutical composition and administered to a cell or patient without causing substantially undesirable biological effects or interacting in a deleterious manner with any of the other components of the composition in which it is contained.

The subject polynucleotide cassette or gene delivery vector, e.g., recombinant virus (virions), can be incorporated into pharmaceutical compositions for administration to mammalian patients, particularly primates and more particularly humans. The subject polynucleotide cassette or gene delivery vector, e.g. virions can be formulated in nontoxic, inert, pharmaceutically acceptable aqueous carriers, preferably at a pH ranging from 3 to 8, more preferably ranging from 6 to 8, or even more preferably from 7 to 8. Such sterile compositions will comprise the vector or virion containing the nucleic acid encoding the therapeutic molecule dissolved in an aqueous buffer having an acceptable pH upon reconstitution.

In some embodiments, the pharmaceutical composition provided herein comprise a therapeutically effective amount of a vector or virion in admixture with a pharmaceutically acceptable carrier and/or excipient, for example saline, phosphate buffered saline, phosphate and optionally one or more other agents such as amino acids, polymers, polyols, sugar, buffers, preservatives, proteins, and inorganic salts such as sodium chloride. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5(2):467-477. The pH of the buffer may be in the range of 6.5 to 7.75, preferably 7 to 7.5, and most preferably 7.2 to 7.4. The pharmaceutical composition may comprise an adenoviral, or adeno-associated adenoviral vector delivery system, which contains a polynucleotide cassette of the present disclosure.

Methods

The ability to deliver a gene expression cassette of the present invention to target cells of choice in vivo and obtain therapeutically effective amounts of the gene product in the cells and in the extracellular environment following the transduction event, may be beneficial for the treatment of many different diseases, including those that depend on the growth of new blood vessels, wherein the goal of the treatment can be to equip target cells with the ability to secrete an anti-angiogenic protein in a therapeutically effective amount. While not wishing to be bound by any theory, an expression cassette capable of enhancing the expression and, ultimately, the secretion of a therapeutic protein may help provide a clinically significant benefit for the patient even when only a subset of the target cells are successfully transduced by the gene delivery vector. High level secretion of the therapeutic protein by the transduced cells may help balance the infectivity or transduction efficiency achieved with any given dose or round of gene therapy.

Accordingly, the subject polynucleotide cassettes and gene delivery vectors, referred to collectively herein as the "subject compositions", find use in expressing a transgene in cells of an animal. For example, the subject compositions may be used in research, e.g. to determine the effect that the gene has on cell viability and/or function. As another example, the subject compositions may be used in medicine, e.g. to treat a disorder. The methods and compositions of the present disclosure may find use in the treatment of any condition that can be addressed, at least in part, by gene therapy of cells. Cells include but are not limited to blood, eye, liver, kidney, heart, muscle, stomach, intestine, pancreas, and skin.

Thus, the present invention provides methods for treating or preventing a disease or disorder, e.g., an ocular disease or disorder, in a subject in need, comprising administering to a subject in need thereof a viral vector or virion comprising a polynucleotide cassette of the present invention that encodes a therapeutic gene product. In preferred embodiments, the therapeutic gene product is a secretory polypeptide, or a protein that is secreted or exported from the cell following its synthesis in the cell and the polynucleotide cassette comprises in 5' to 3' order: (a) a first enhancer region comprising a CMV sequence (SEQ ID NO:1); (b) a promoter region, comprising a CMV sequence (SEQ ID NO:4); (c) a 5'UTR region comprising, in 5' to 3' order, TPL and eMLP sequences (SEQ ID NO:11 and SEQ ID NO:12, respectively); (d) a coding sequence encoding a peptide or polypeptide; (e) a second enhancer region comprising a full EES sequence (SEQ ID NO:13); and (f) a HGH polyadenylation site (SEQ ID NO:14).

In related embodiments, some methods provide for the expression of a gene in cells in vitro or in vivo, the method comprising contacting the cells with a composition of the present disclosure. In some embodiments, contacting occurs in vitro. In some embodiments, contacting occurs in vivo, i.e., the subject composition is administered to a subject. The composition can be administered parenterally, via intravenous injection or infusion, orally. In certain embodiments, it is administered to the eye by injection, e.g., administered to the retina, sub-retina or vitreous. In certain embodiments, it is administered by retinal injection, sub-retinal injection, or intravitreal injection. In certain embodiments, it is administered locally or directly to a tissue or organ of interest, e.g., via injection into the liver.

The subject can be a mammal, including for example a human subject in need of treatment for a particular disease or disorder.

For instances in which mammalian cells are to be contacted in vitro with a subject polynucleotide cassette or gene delivery vector comprising a subject polynucleotide cassette, the cells may be from any mammalian species, e.g. rodent (e.g. mice, rats, gerbils, squirrels), rabbit, feline, canine, goat, ovine, pig, equine, bovine, primate, human. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from a mammal by any convenient method, e.g. whole explant, biopsy, etc. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To promote expression of the transgene, the subject polynucleotide cassette or gene delivery vector comprising a subject polynucleotide cassette will be contacted with the cells for about 30 minutes to 24 hours or more, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, 24 hours, etc. The subject polynucleotide cassette or gene delivery vector comprising a subject polynucleotide cassette may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. Contacting the cells may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Typically, an effective amount of subject polynucleotide cassette or gene delivery vector comprising a subject polynucleotide cassette is provided to produce the expression of the transgene in cells. As discussed elsewhere herein, the effective amount may be readily determined empirically, e.g. by detecting the presence or levels of transgene gene product, by detecting an effect on the viability or function of the cells, etc. Typically, expression will be enhanced 2-fold or more relative to the expression from a reference or control polynucleotide cassette, for example 3-fold, 4-fold, or 5-fold or more, in some instances 10-fold, 20-fold or 50-fold or more, e.g. 100-fold. One example of a reference cassette for comparison purposes is the CMV reference control cassette, described herein. In specific embodiments, the transgene encodes a secretory protein and the polynucleotide cassette expresses the secretory protein in mammalian cells at a level that is at least 2-fold, 5-fold, 10-fold, 5 to 10 fold, 5 to 15 fold, or 10 to 15 fold higher than the level of expression of the secretory protein from the CMV reference control cassette in the mammalian cells. According to some embodiments, when the transgene is one that encodes a non-secreted protein the polynucleotide cassette of this invention expresses the non-secreted protein in mammalian cells at a level that is approximately the same as, within 10-20% of, less than about 1.5×, or less than about 2× the level of expression of the non-secreted protein from the CMV reference control cassette in mammalian cells. The expression level of the secretory protein for each cassette may be measured by an immunoassay or antigen-capture assay and may be represented as the quantity or concentration of protein per volume of supernatant in the extracellular environment (e.g., cell culture medium or supernatant).

Immunoassay methods for measuring the presence and quantity (and therefore the expression level) of a protein in a biological or cell sample are known in the art (e.g., Hage, D. S. (1999) "Immunoassays" Analytical Chemistry 71(12): 294-304; The Immunoassay Handbook, Fourth Edition: Theory and Applications of Ligand Binding, ELISA and Related Techniques by David Wild (Editor), Elsevier Science (2013)). Generally, the immunoassay is based on a reaction between the target protein and an antibody, or antibody fragment, specifically binding to the protein. Immunoassay may be performed in a liquid or solid phase system, but for ease of detection a solid phase may be preferred. Suitable immunoassays include but are not limited to sandwich and competition assays, Western blotting, ELISA (enzyme-linked immunosorbent assay), radioimmunoassay (RIA), fluoroimmunoassay (FIA), and the like. The biological sample can be cell culture medium or supernatant (a sample taken from the culture without lysing the cells), cell lysate, whole cells, blood, serum, plasma, or other body fluid or tissue. In some embodiments, as when the transgene is a selectable marker, the population of cells may be enriched for those comprising the subject polynucleotide cassette by separating the modified cells from the remaining population. Separation may be by any convenient separation technique appropriate for the selectable marker used. For example, if the transgene is a fluorescent marker, cells may be separated by fluorescence activated cell sorting, whereas if the transgene is a cell surface marker, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the cells. Cell compositions that are highly enriched for cells comprising the subject polynucleotides are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition.

For instances in which cells are to be contacted in vivo with a subject polynucleotide cassette or gene delivery vector comprising a subject polynucleotide cassette, the subject may be any mammal, e.g. rodent (e.g. mice, rats, gerbils), rabbit, feline, canine, goat, ovine, pig, equine, bovine, human, or non-human primate.

The methods and compositions of the present disclosure find use in the treatment of any condition that can be addressed, at least in part, by gene therapy of cells. Cells include but are not limited to blood, eye, liver, kidney, heart, muscle, stomach, intestine, pancreas, and skin. One embodiment is a method for treating a medical condition in a subject in need of treatment, the method comprising administering to the subject a gene delivery vector that contains a polynucleotide cassette as disclosed herein, wherein the cassette encodes a polypeptide effective for reducing one or more signs or symptoms of the medical condition. In some embodiments the medical condition is an ocular disease, the gene delivery vector is an adeno-associated virus, and the polypeptide is a polypeptide that is secreted by the cells transduced by the vector. In one embodiment, the secreted protein inhibits VEGF signaling. For example, the secreted protein can be a VEGF-binding protein. In some embodiments the ocular disease is choroidal neovascularization or macular degeneration. Specific forms of macular degeneration may include acute macular degeneration, non-exudative age related macular degeneration, and exudative age related macular degeneration. Administration can be by any suitable means, including, e.g., ocular delivery, intravitreal injection, intraocular injection, retinal injection, subretinal injection, parenteral administration, intravenous injection or infusion, and injection into the liver.

In some embodiments, the gene delivery vector is administered to the eye of the subject in need of treatment. In some embodiments the gene delivery vector is administered to the subject via intraocular injection, by intravitreal injection, or by any other convenient mode or route of administration. In some embodiments the subject is a human subject suffering from or at risk for developing macular degeneration or ocular neovascularization.

In some embodiments, the subject method results in a therapeutic benefit, e.g. preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

Expression of the transgene using the subject transgene is expected to be robust. Accordingly, in some instances, the expression of the transgene, e.g. as detected by measuring levels of gene product, by measuring therapeutic efficacy, etc., may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g. as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In certain embodiments, the method comprises the step of detecting expression of the transgene in the cells, wherein expression is enhanced relative to expression from a polynucleotide cassette not comprising the one or more improved elements of the present disclosure, i.e. a reference control. Typically, expression will be enhanced 2-fold or more relative to the expression from a reference, i.e. a control polynucleotide cassette, for example 3-fold, 4-fold, or 5-fold or more, in some instances 10-fold, 20-fold or 50-fold or more, e.g. 100-fold, as evidenced by, e.g. earlier detection, higher levels of gene product, a stronger functional impact on the cells, etc. In one aspect, the transgene encodes a secretory polypeptide such as sFLT1.

Typically, if the subject composition is a virus, e.g., an rAAV comprising a polynucleotide cassette of the present disclosure, an effective amount to achieve a change in a subject, or to produce a therapeutic effect, will be about $1 \times 10^8$ vector genomes or more, in some cases $1 \times 10^9$, $1 \times 10^{10}$, $1 \times 10^{11}$, $1 \times 10^{12}$, or $1 \times 10^{13}$ vector genomes or more, in certain instances, $1 \times 10^{14}$ vector genomes or more, and usually no more than $1 \times 10^{16}$ vector genomes. In some cases, the amount of vector genomes that is delivered is at most about $1 \times 10^{16}$ vector genomes, e.g. $1 \times 10^{15}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes, and typically no less than $1 \times 10^8$ vector genomes. In some cases, the amount of vector genomes that is delivered is $1 \times 10^{10}$ to $1 \times 10^{11}$ vector genomes. In some cases, the amount of vector genomes that is delivered is $1 \times 10^{10}$ to $3 \times 10^{12}$ vector genomes. In some cases, the amount of vector genomes that is delivered is $1 \times 10^9$ to $3 \times 10^{13}$ vector genomes. In some cases, the amount of vector genomes that is delivered is $1 \times 10^8$ to $3 \times 10^{14}$ vector genomes.

In some cases, the amount of pharmaceutical composition to be administered may be measured using multiplicity of infection (MOI). In some cases, MOI may refer to the ratio or multiple of vector particles or viral genomes to the cells to which the polynucleotide cassette may be delivered. In some cases, the MOI may be $1 \times 10^6$. In some cases, the MOI may be $1 \times 10^5$ to $1 \times 10^7$. In some cases, the MOI may be $1 \times 10^4$ to $1 \times 10^8$. In some cases, recombinant viruses of the disclosure are about $1 \times 10^1$, $1 \times 10^2$, $1 \times 10^3$, $1 \times 10^4$, $1 \times 10^5$, $1 \times 10^6$, or $1 \times 10^7$ MOI.

In some aspects, the pharmaceutical composition comprises about $1 \times 10^8$ to about $1 \times 10^{15}$ particles of recombinant viruses, about $1 \times 10^9$ to about $1 \times 10^{14}$ particles of recombinant viruses, about $1 \times 10^{10}$ to about $1 \times 10^{13}$ particles of recombinant viruses, or about $1 \times 10^{11}$ to about $3 \times 10^{12}$ particles of recombinant viruses.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dose amount. Effective amounts of dose and/or dose regimen can readily be determined empirically from preclinical assays, from safety and escalation and dose range trials, individual clinician-patient relationships, as well as in vitro and in vivo assays.

All of the above U.S. patents, U.S. patent application publications, U.S. patent applications, foreign patents, foreign patent applications and non-patent publications referred to in this specification are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., Cold Spring Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clontech.

Example 1

Construction of Polynucleotide Expression Cassettes

Important considerations in the development of any gene therapy method are the vehicle used to deliver the gene and the expression cassette used to drive production of the transgene once inside the cell. The cassette is preferably one that promotes robust expression of the transgene at a level that is sufficient to provide a quick and long-lasting therapeutic benefit for the patient. To that end a series of polynucleotide expression cassettes containing various combinations and permutations of regulatory elements and a protein coding sequence were generated using standard recombinant DNA cloning techniques (FIG. 1).

Example 2

Construction of Recombinant Plasmids

Recombinant plasmids comprising each of the candidate polynucleotide cassettes and a coding sequence encoding Aflibercept were constructed and cloned in *E. coli* using conventional DNA recombination and cloning techniques. Each cassette was positioned between the inverted terminal repeat (ITR) sequences of adeno-associated virus serotype 2 (AAV2), as shown in the vector map for cassette 11 (FIG. 11), for subsequent transfer of the cassettes to the AAV genome and preparation of recombinant AAV virions.

Figure 11:
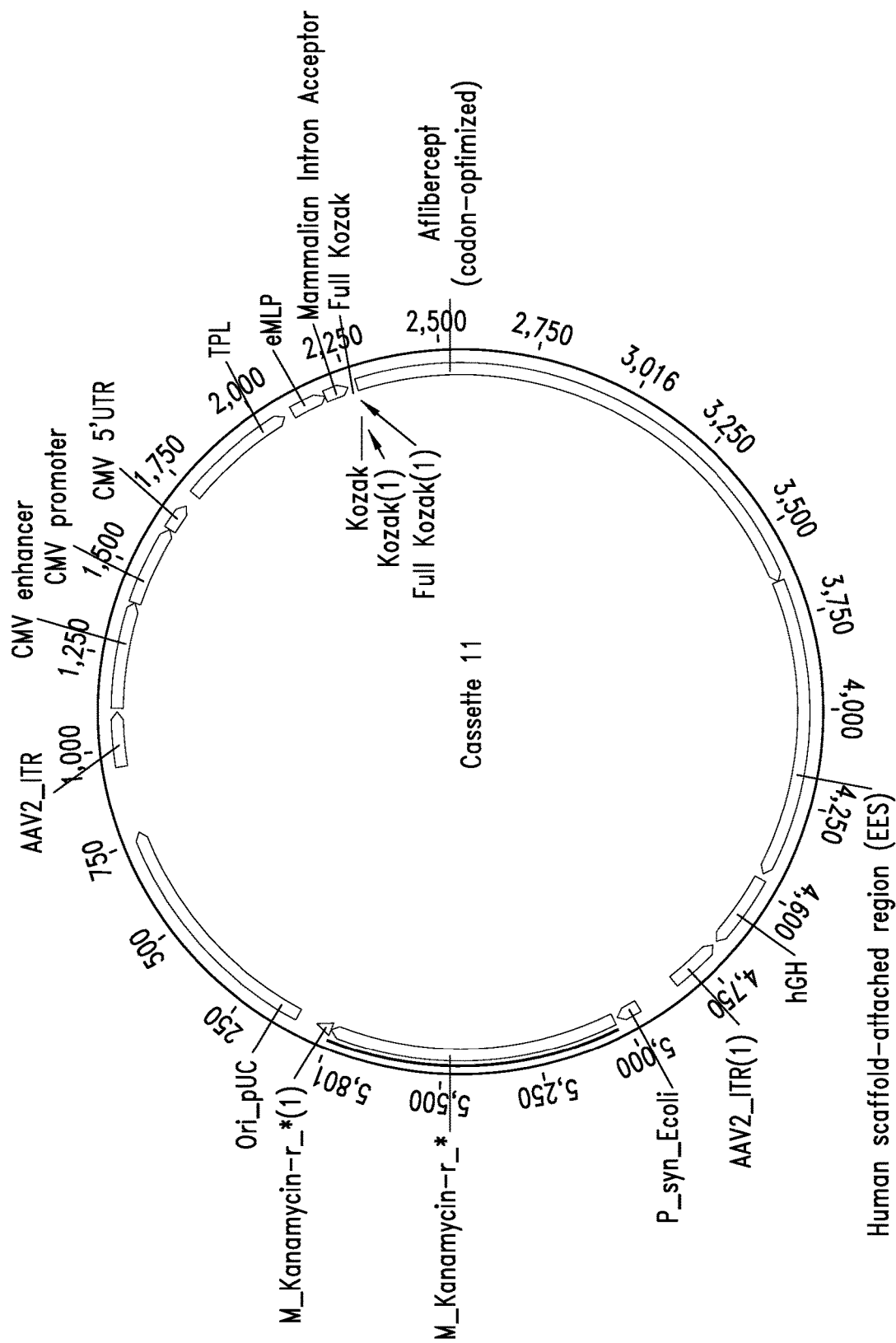
FIG. 11 shows one illustrative embodiment of a recombinant plasmid containing Cassette 11. Inverted terminal repeats (ITRs) from adeno-associated virus serotype 2 (AAV2) flank the cassette.

As shown in FIG. 11, cassette 11 included, in 5' to 3' order, a CMV enhancer, a CMV promoter, a 5'UTR comprising sequences from TPL and eMLP, a protein coding sequence, a full expression enhancer sequence (EES), and a human growth hormone polyadenylation signal sequence (HGH polyA). In similar fashion, cassette 12 included, in 5' to 3' order, a CMV enhancer, a CMV promoter, TPL and eMLP 5'UTR sequences, a protein coding sequence, the 410-564 portion of the expression enhancer sequence (410-564 EES), the cis-acting post-transcriptional regulatory element of hepatitis B virus (HPRE), and a bovine growth hormone polyadenylation signal sequence (BGH polyA). The polynucleotide sequences for cassettes 10, 11, 12, and 14, and for the CMV reference control cassette, as used in these studies, are shown in Tables 1, 2, 3, 4, and 5 respectively. The ITRs, regulatory elements, and coding region, are listed as they occur in the plasmid in 5' to 3 order, starting at the top of table and continuing to the bottom of the table. A CMV reference cassette (Table 5) was also constructed and tested in a side-by-side comparison with other selected cassettes of the present disclosure.

Example 3

Protein Expression in Transfected Mammalian Cells In Vitro

To assess the expression properties of each cassette in vitro, each recombinant construct was transfected into mammalian cells using FuGENE®6 Transfection Reagent (Promega). In a first series of experiments (FIG. 2), the cassettes encoded a protein that is secreted from the cell upon translation. Following transfection, the cells were incubated for 48 hours. Cell culture supernatant from each culture was then sampled and assayed by an immune assay to assess the levels of secreted protein by each transfected cell culture. FIG. 2 shows the expression levels for cassettes C1-C18 relative to that of a "base plasmid" cassette, described in FIG. 1. As shown in FIG. 2, highest average expression by HeLa cells was observed for those cells transfected with cassettes 11 and 12.

Example 4

Protein Expression in Transduced Mammalian Cells In Vitro

Based on the results shown in FIG. 2, five cassettes (C7, C11, C12, C13, and C14) were selected for further study. An experiment was performed to compare the expression of a secreted protein from each cassette when delivered to mammalian cells in vitro by recombinant adeno-associated virus. The C7, C11, C12, C13, and C14 cassettes used in the HeLa cell study shown in FIG. 2 were each packaged within the AAV7m8 capsid (Dalkara et al. Sci. Transl. Med., 2013, Vol. 5, Issue 189, 189ra76). Separate cultures of HEK293 cells were transduced with each recombinantAAV7m8 vector at an MOI of $3 \times 10^5$ and then incubated for 3 days. Following incubation, supernatant was collected from each culture and assayed using an immunoassay to measure the quantity of secreted protein in the supernatant by each culture over the course of the 3-day incubation. As in transfected HeLa cells (FIG. 2), highest expression in HEK293 cells was observed for those cells transduced with cassettes 11 and 12 (FIG. 3).

Example 5

Protein Expression in Transduced Pig Retinal Explant Cultures

Figure 3:
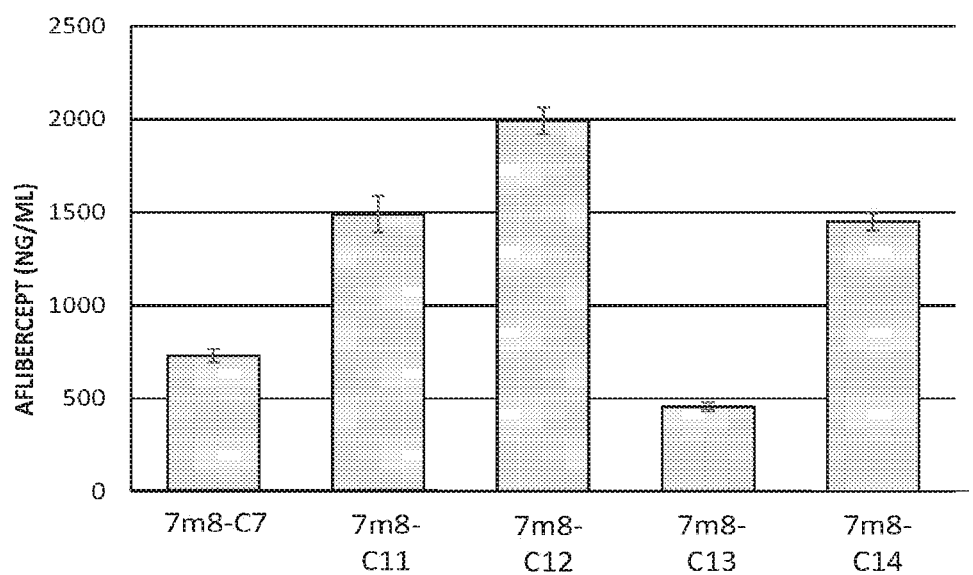
FIG. 3 shows the expression of aflibercept, a secreted protein, from select polynucleotide cassettes following transduction into HEK 293 cells.

The recombinant AAV2.7m8 vectors used in the study shown in FIG. 3 were further tested in a porcine retinal explant culture system. Porcine retinas have anatomic and physiologic features that are similar to humans and can therefore serve as a suitable surrogate in pre-clinical testing. Explant cultures of full-thickness retina preserve the complex intracellular processes and communications among the neural retinal cells and are useful models in target-tissue validation of AAV vector variants.

Transduction of Pig Retinal Explants

Figure 4A:
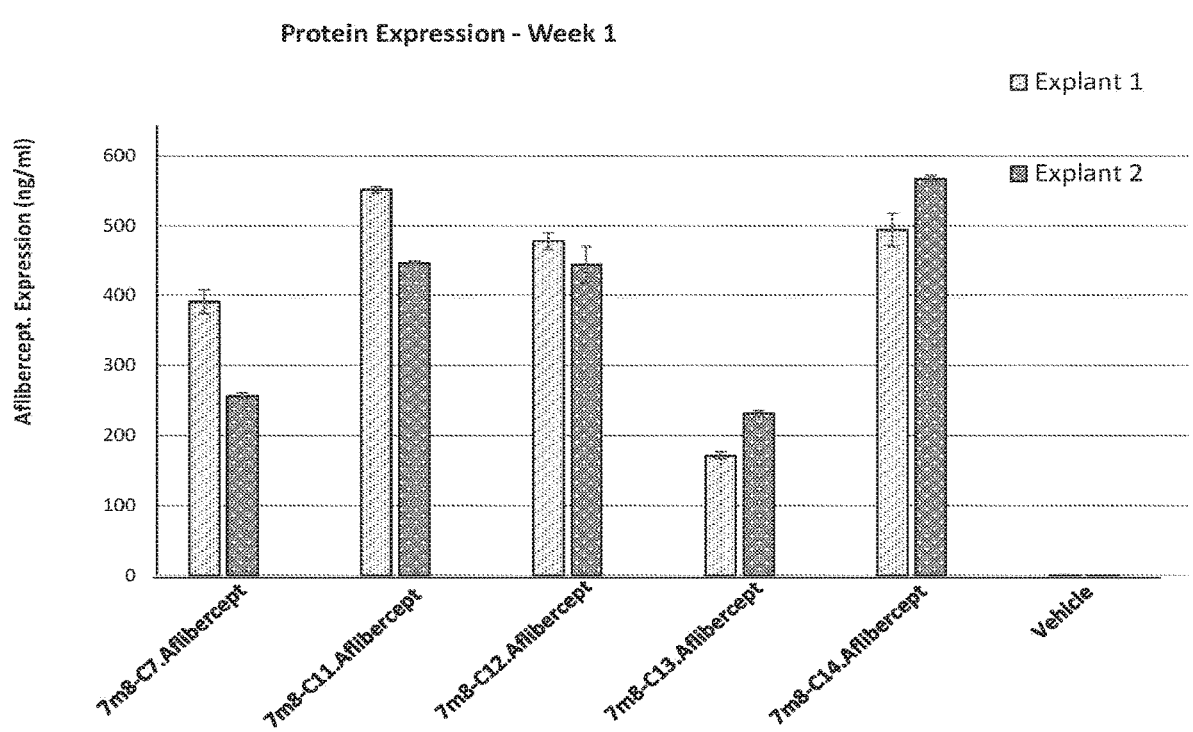
FIGS. 4A and 4B show the expression of aflibercept, a secreted protein, from selected polynucleotide cassettes in transduced pig retinal explants one week (FIG. 4A) and two weeks (FIG. 4B) after transduction. Each cassette was packaged in a 7m8 capsid, a variant of AAV2. Background signal associated with the assay was determined with a vehicle (buffer only) non-virus control.
Figure 4B:
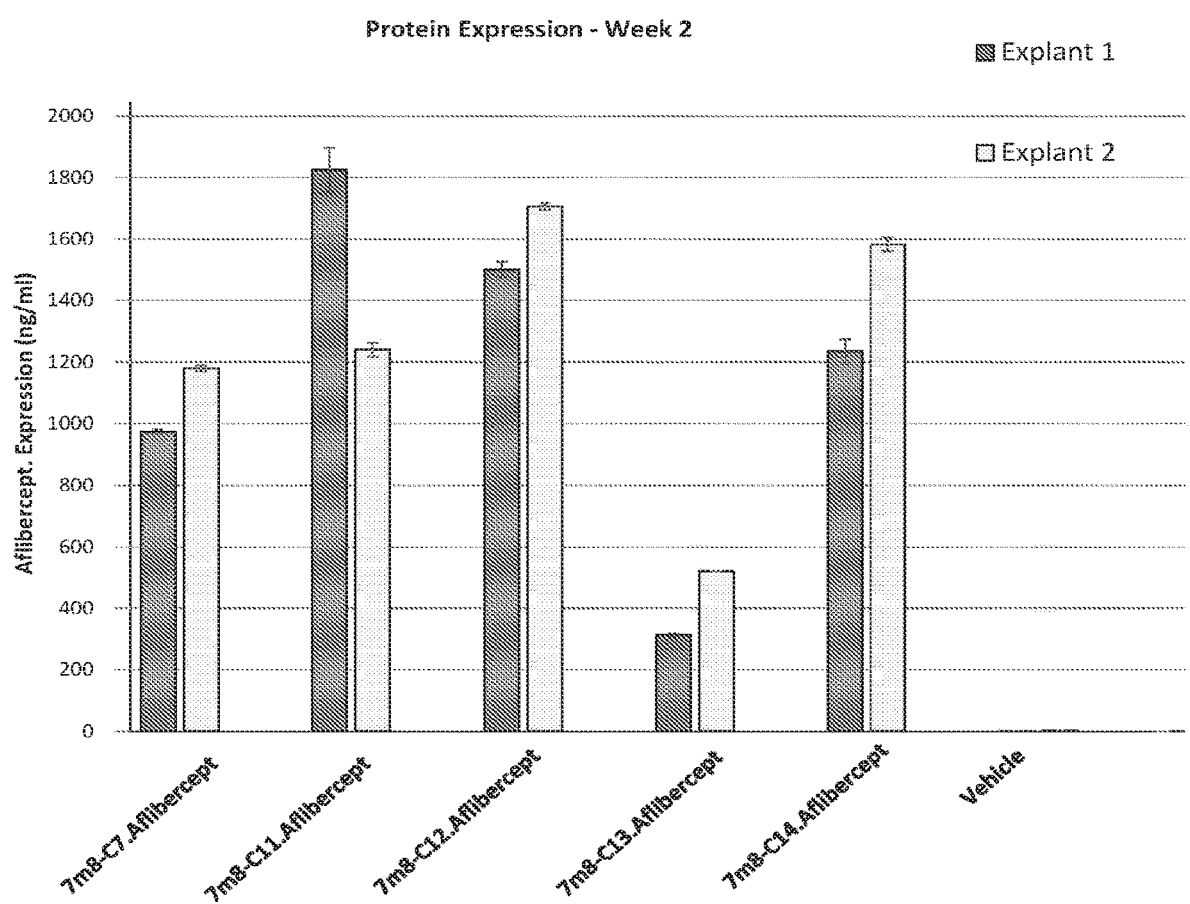

The 7m8.AAV2 vector is a variant AAV2 vector that is able to transduce photoreceptors better than wild type AAV2 (Dalkara et al. *Sci. Transl. Med.* "In Vivo-Directed Evolution of a New Adeno-Associated Virus for Therapeutic Outer Retinal Gene Delivery from the Vitreous", 2013, Vol. 5, Issue 189, 189ra76). Pig retinal explants, with full thickness retina, were transduced with the 7m8 vectors at an MOI of $2 \times 10^4$. Supernatant was collected one week and two weeks after transduction and the amount of secreted protein present in the supernatant was measured by an immunoassay. The experiment was run in duplicate (Explants 1 and 2) and the results showing the level of protein expressed and secreted from each transduced explant, as measured by the quantity of protein in the culture supernatant are shown in FIG. 4, alongside the background level of a non-transduced "vehicle" control explant. As shown in FIG. 4, the trend in protein expression levels for this panel of cassettes correlated with the trend observed for transduced HEK293 cells in vitro (FIG. 3), with cassettes 11, 12, and 14 providing the three highest expression levels and cassettes 7 and 13 the lowest.

Example 6

Expression of sFLT-1 in Transfected Mammalian Cells In Vitro

It was of interest to study the expression properties of the cassettes in regard to other proteins and other mammalian cell types. For this purpose, the coding sequences for two other proteins, sFLT-1 and green fluorescent protein (GFP), were separately cloned into polynucleotide cassettes C10, C11, and C12. For comparison, a sequence encoding sFLT1 was also separately cloned into the base plasmid cassette (FIG. 1) and a CMV control cassette ("CMV-sFLT1"). The CMV-sFLT1 control construct comprised, in 5' to 3' order, a CMV enhancer sequence (SEQ ID NO:2), a CMV promoter (SEQ ID NO:21), a chimeric intron (SEQ ID NO:22), a 5'UTR (SEQ ID NO:23), a coding sequence encoding sFLT-1 (SEQ ID NO:24), a 3'UTR (SEQ ID NO:25), and an SV40 polyA sequence (SEQ ID NO:26), as described in Table 5. With the exception of the CMV-sFLT1 control construct, the coding sequence for sFLT-1 (also referred to herein as sFLT1) was codon optimized (CO) for expression in primate cells.

Figure 5:
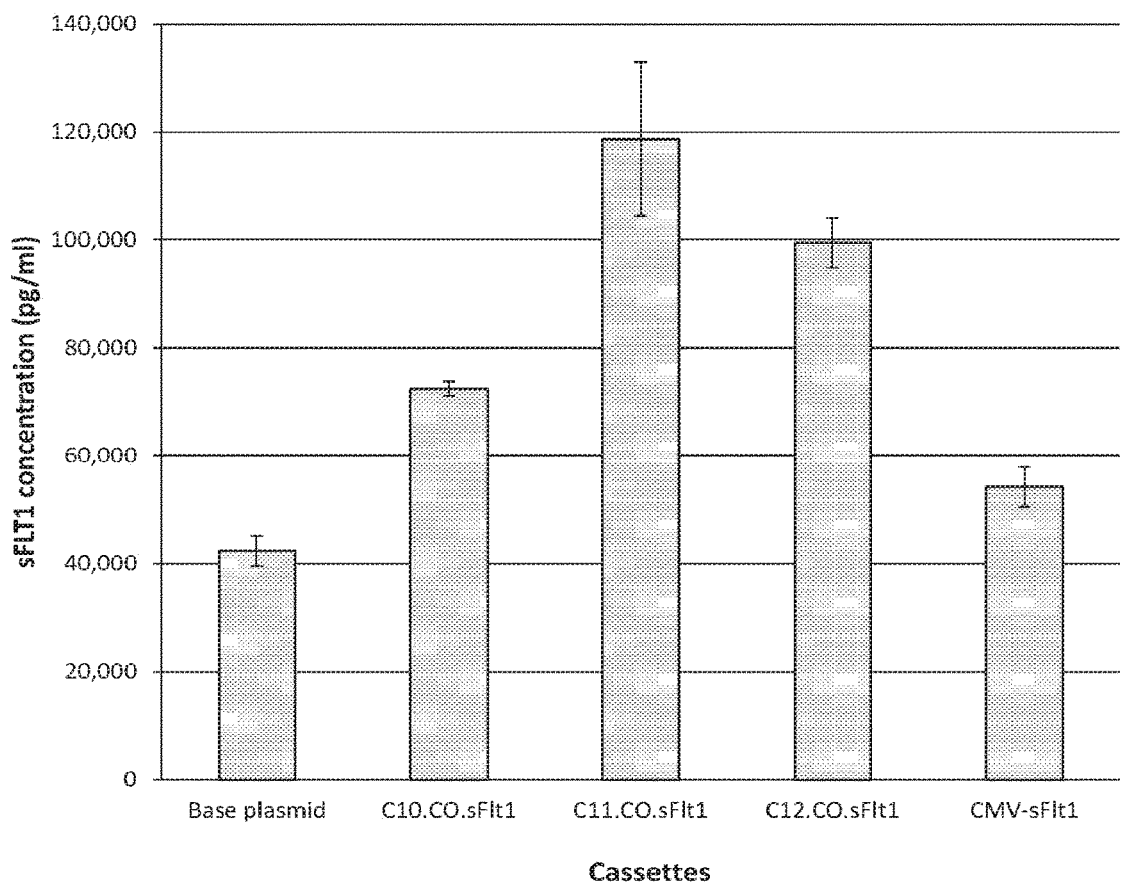
FIG. 5 depicts the comparison of sFLT-1 expression from various polynucleotide cassette constructs, including a reference cassette (CMV-sFLT1), in transfected ARPE-19 cells. The sequence encoding sFLT-1 in cassettes 10, 11, and 12 was codon optimized ("CO"). The Base plasmid, only had the codon-optimized sFLT1 under a ubiquitous promoter, but without any other regulatory elements.
Figure 6:
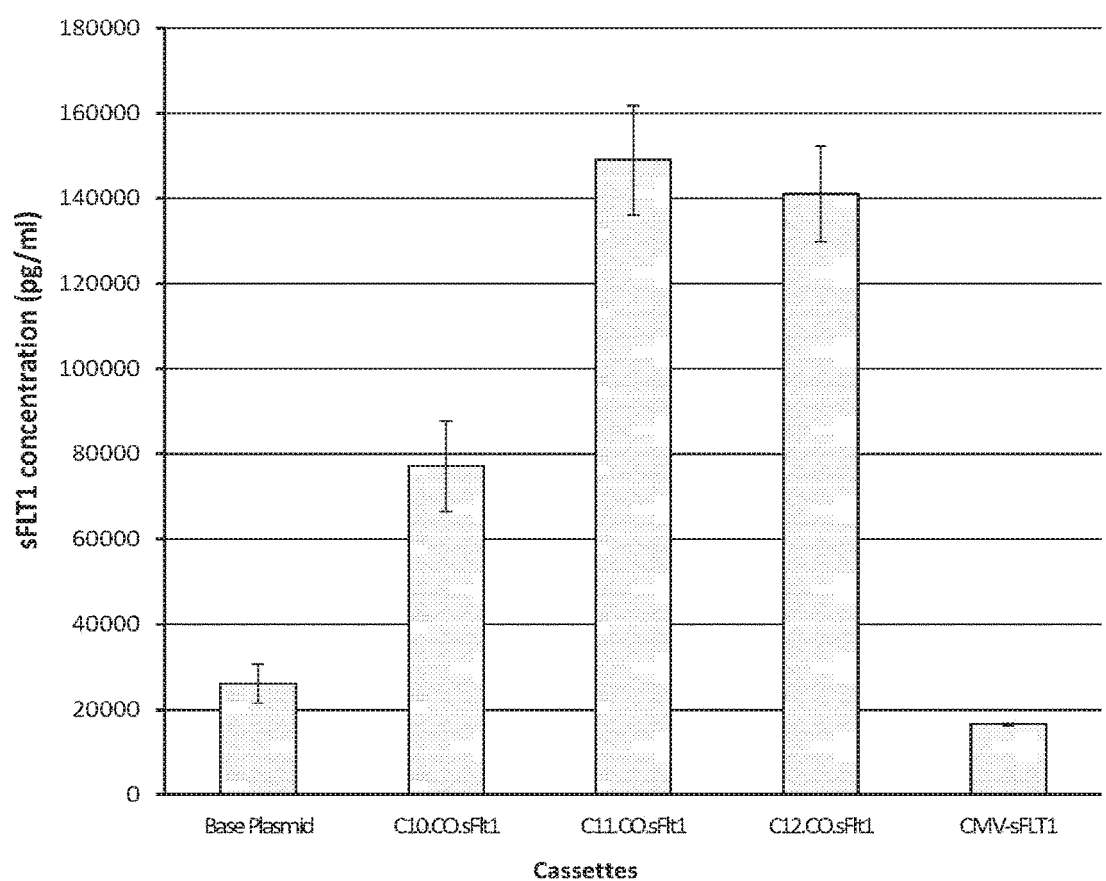
FIG. 6 depicts the comparison of sFLT-1 expression from various constructs in transfected HEK293 cells.
Figure 7:
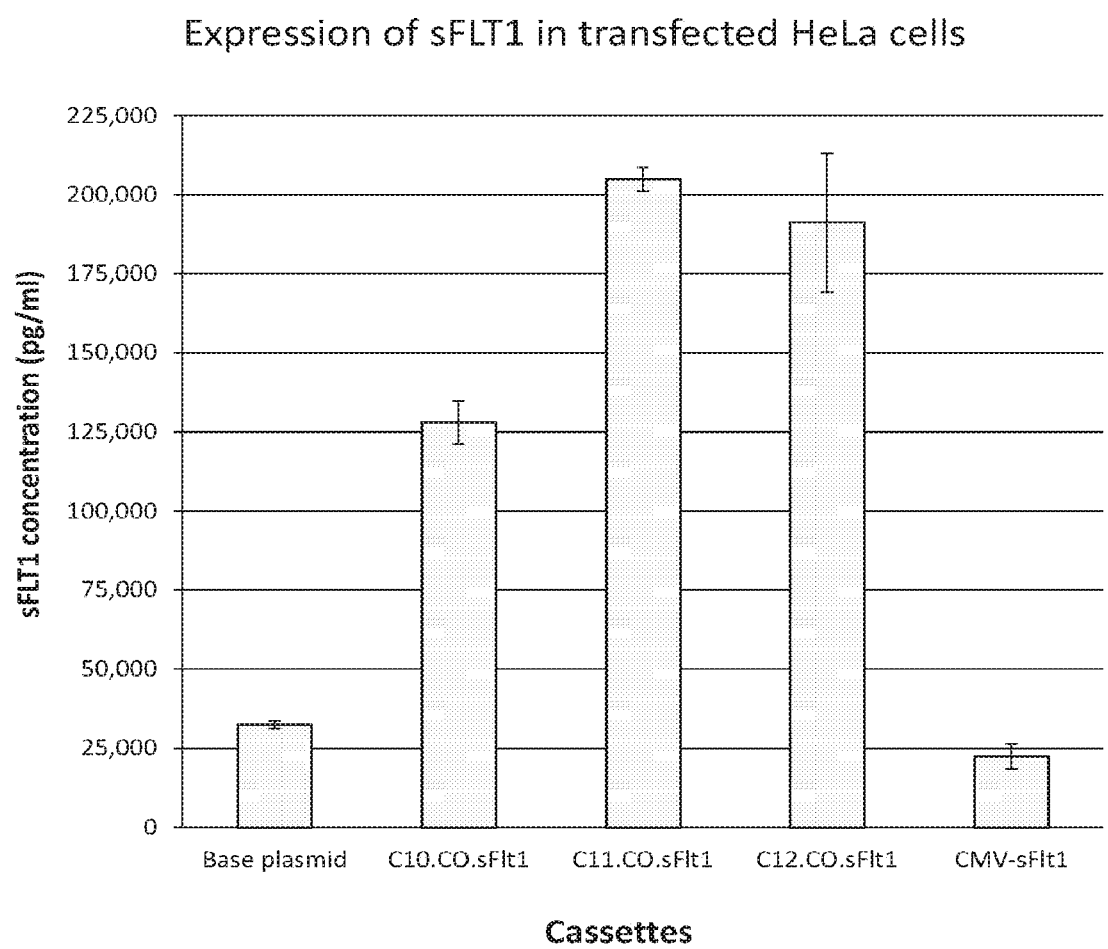
FIG. 7 depicts the comparison of sFLT-1 expression from various constructs, including a reference cassette (CMV-sFLT1), in transfected HeLa cells.
Figure 8:
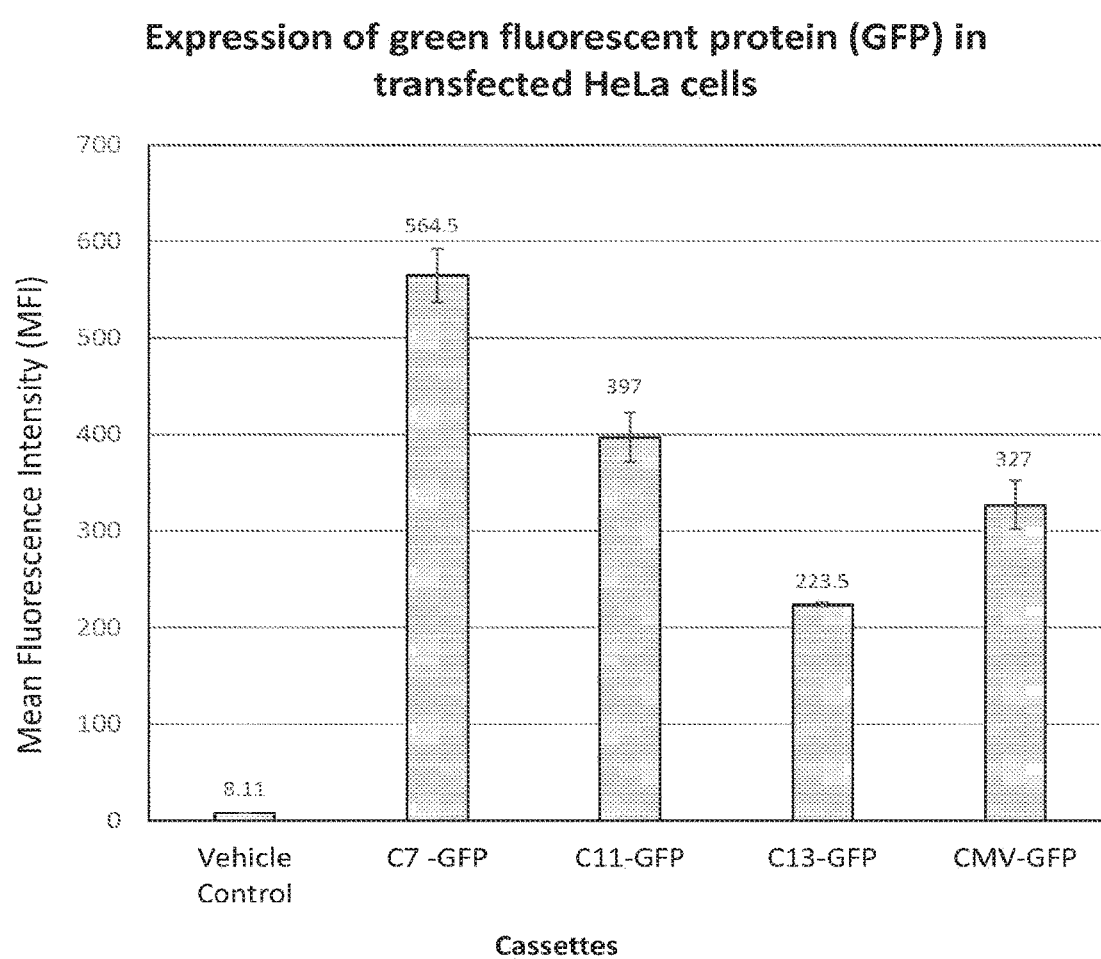
FIG. 8 shows the expression of green fluorescent protein (GFP) from polynucleotide cassettes C7, C11, and C13 in transfected HeLa cells as compared to the expression of GFP from the CMV reference control cassette and as compared to a vehicle (buffer only) control.

The sFLT1-encoding vectors were transfected into three different cell lines: a retinal pigment epithelial cell line (ARPE19 cells), HEK293 cells, and HeLa cells. Transfections were performed using FuGENE®6 Transfection Reagent. Following the transfection step, cells were incubated for 48 hours, and the amount of sFLT1 protein present in the cell culture supernatant was measured using the sFLT1 ELISA Kit from R & D Systems. Plasmids encoding GFP under the control of cassette 7, 11, or 13, were transfected into HeLa cells and compared to a plasmid expressing GFP under the control of the CMV promoter (CMV-sFLT1, described above). After approximately 48 hours, the cells were trypsinized and the percentage of GFP-positive cells in each culture was assessed by flow cytometry (BD FACSCalibur™). Results are shown in FIGS. 5-8. In general, highest expression of sFLT1 was observed in cells transfected with cassettes 11 and 12, as compared to any of the other cassettes tested (FIGS. 5-7). More specifically, the expression of sFLT1 from cassette 11 in ARPE19 cells ($\bar{x}$=118,721 pg/mL) was about 2.2× (or about 2-fold) higher than the expression of sFLT1 from the CMV-sFLT1 control cassette ($\bar{x}$=54268.53 pg/mL) in ARPE19 cells (FIG. 5). The expression of sFLT1 from cassette 11 in HEK293 cells ($\bar{x}$=148985.40 pg/mL) was about 9× higher than the expression of sFLT1 from the CMV-sFLT1 control cassette in HEK293 cells ($\bar{x}$=16525.9 pg/mL) (FIG. 6). And the expression of sFLT1 from cassette 11 in transfected HeLa cells ($\bar{x}$=204957.57 pg/mL) was about 9× higher than the expression of sFLT1 from the CMV-sFLT1 control cassette in HeLa cell cultures ($\bar{x}$=22363.03 pg/mL) (FIG. 7). Surprisingly, however, although the level of sFLT1 expressed from cassette 11 was consistently higher than the level of sFLT1 expressed from any of the other cassettes tested, and was significantly higher than the level of sFLT1 expressed from the CMV-sFLT1 control cassette in every cell line tested (FIGS. 5-7), cassette 11 provided a similar level of protein per cell compared to the CMV-control cassette when the coding sequence was changed to one that encoded GFP. As shown in FIG. 8, the fold difference in amount of protein expressed in mammalian cells by cassette 11 and CMV-sFLT1, previously observed when each cassette encoded sFLT1, was significantly reduced when the coding sequence was changed from one encoding sFLT1, a secreted protein, to one encoding GFP, a non-secreted, cytoplasmic protein. Based on these unexpected results, cassette 11, as compared to other cassettes, is believed to be especially well suited for expressing polypeptides that are secreted from the cell.

Example 7

Expression of SFLT-1 in Transduced Mammalian Cells

Figure 9:
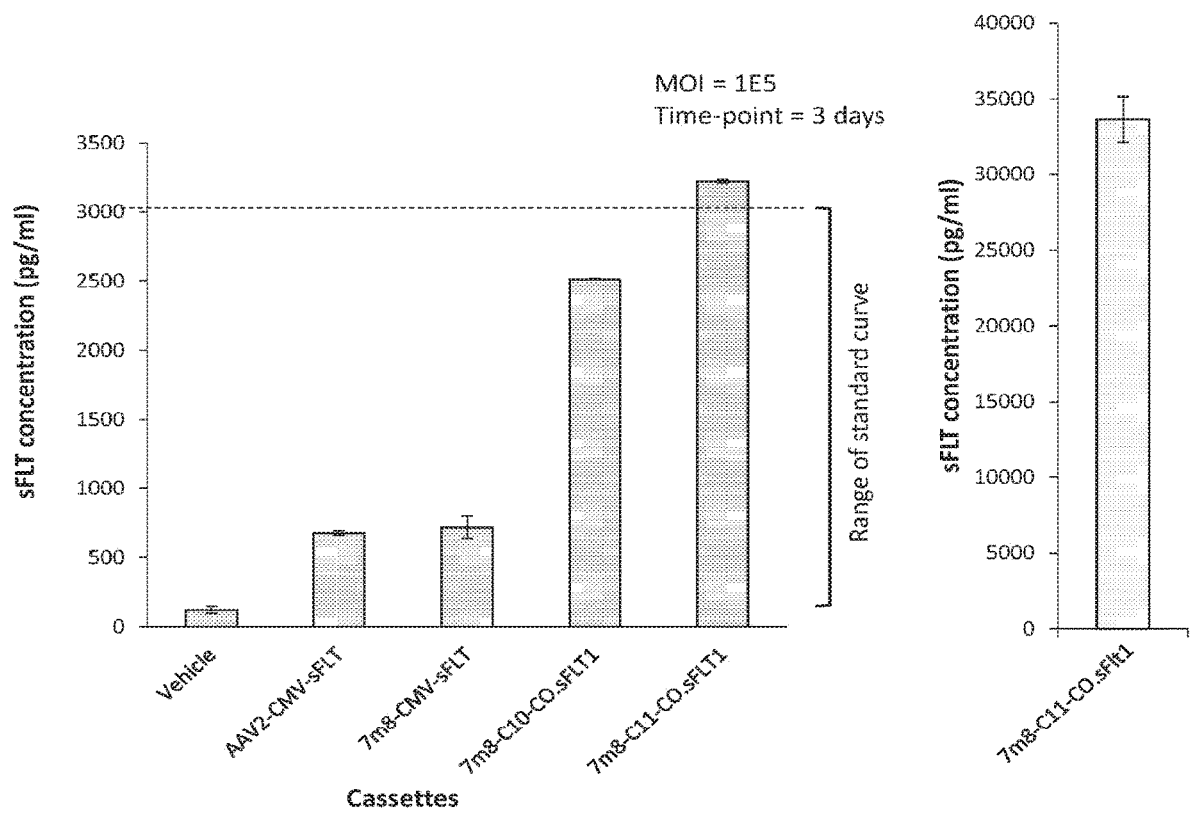
FIG. 9 depicts the comparison of sFLT-1 expression from various polynucleotide cassettes in transduced HEK293 cells. Data represent the amount of sFLT-1 in cell culture supernatants three days after transduction with the 7m8 vector. In each case, the vector packaged the indicated cassette. Expression (as measured in cell culture supernatants) of sFLT-1 from cassettes C10 and C11 was compared to the expression of sFLT-1 from the CMV reference cassette. Background signal was determined with a vehicle (buffer only) control. As a further control, cells were transduced with recombinant AAV2 vector containing the CMV-sFLT1 reference control cassette. In the first experiment, the amount of sFLT1 secreted from cassette 11 was higher than the range of the immunoassay, so it had to be diluted further and analyzed.

In a further study, the C10 and C11 cassettes, containing a codon-optimized coding sequence encoding human FLT-1, and the control CMV-sFLT-1 cassette were packaged in the 7m8 capsid to form recombinant 7m8.AAV2 virions encoding sFLT-1 under the control of the various cassette constructs. The CMV-sFLT1 control construct was also packaged in the wild-type AAV2 capsid (AAV2-CMV-sFLT1). HEK293 cells were transduced with each adeno-associated viral construct at an MOI of 1×105. Three days post-transduction, supernatant from each culture was collected and the concentration of sFLT-1 in each supernatant sample was assayed using an sFLT-1 ELISA kit. As shown in FIG. 9, highest expression was observed in the HEK293 cells transduced with cassette 11 (C11). The expression of sFLT-1 from cassette 11 in the transduced HEK293 cells was approximately 50× higher than the expression of sFLT-1 from the control CMV-sFLT1 cassette (33661 pg/mL compared to 718 pg/mL). The data shown on the right side of FIG. 9 shows that supernatant from C11 transduced cells had to be further diluted to have the sample in the range of the assay's standard curve.

Example 8

Expression of SFLT-1 in Transduced Pig Retinal Explants

Figure 10A:
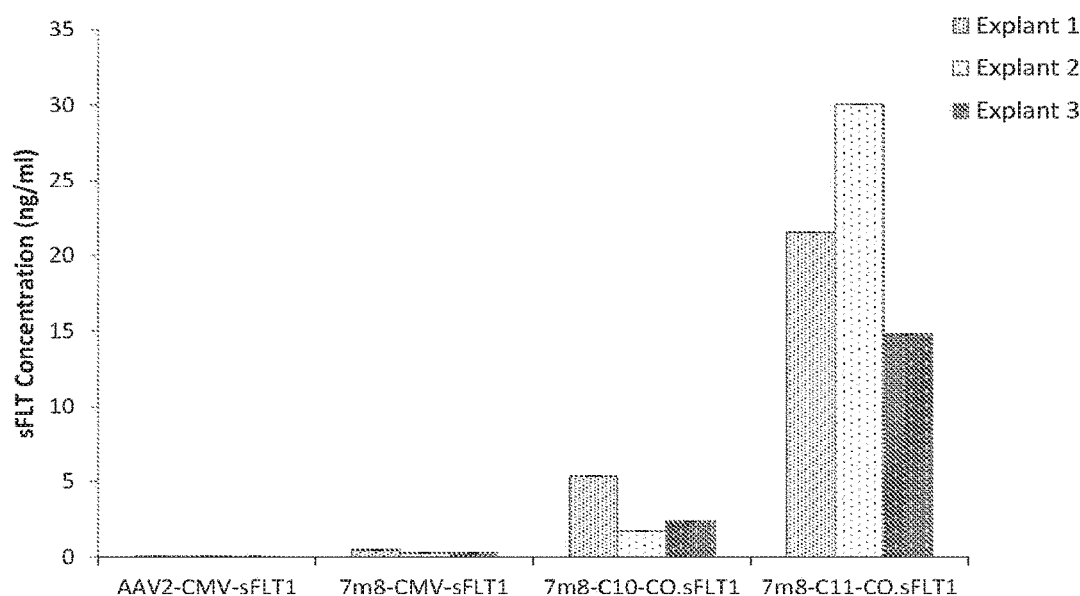
FIGS. 10A and 10B show the expression of sFLT1 from selected polynucleotide cassettes in transduced pig retinal explants. sFLT1 expression is measured in supernatant (FIG. 10A) as well as in the tissue lysate (FIG. 10B).
Figure 10B:
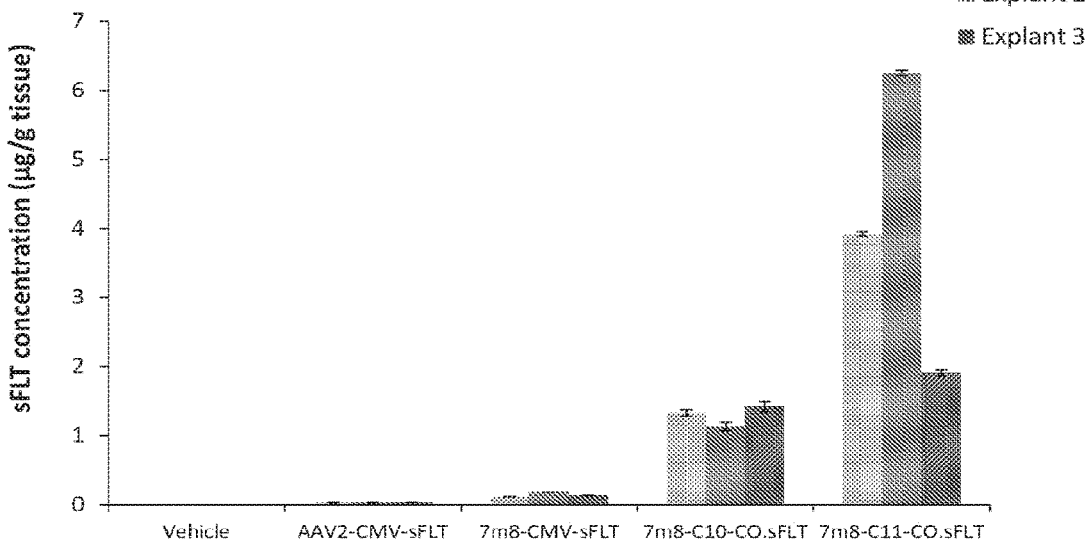

To compare the expression of sFLT-1 retinal tissue, pig retinal explants were transduced with each of the recombinant AAV vectors shown in FIG. 9. The experiment was run in triplicate and each explant was transduced at an MOI of 4×10⁴. Following transduction, media was changed every 3 days. After two weeks, 3-day-old media was collected from each explant culture and the amount of sFLT-1 in the medium from each culture was assessed using an sFLT-1 ELISA kit. In addition, retinal explants were lysed and tissue lysates were assayed by ELISA for sFLT-1 expression within the cells. Results are shown in FIG. 10. As shown in FIG. 10, the amount of sFLT-1 in the supernatant from the explants transduced with an AAV2.7m8 encoding sFLT-1 under the control of cassette 11 (7m8-C11-CO.sFLT) is, on average, approximately 60× higher than the amount of sFLT-1 in the supernatant of explants transduced with an AAV2.7m8 encoding sFLT-1 under the control of the control of the CMV cassette (7m8-CMV-sFLT1). The relative differences in the amount of sFLT-1 in the supernatants from the various explant cultures correlated with the relative differences in the amount of sFLT-1 protein found inside the cells (FIG. 10; Tissue Lysate), indicating that cassette 11 promotes higher expression of sFLT-1 in mammalian cells, and thereby facilitates the secretion of higher levels of the protein outside the transduced cells, in the extracellular medium, as compared to the levels of sFLT-1 observed in and around (i.e., in the extracellular environment of) cells transduced with the 7m8-CMV-sFLT1 control cassette and other sFLT-1-encoding cassettes tested, as shown in FIGS. 9 and 10.

Example 9

Expression of Aflibercept in Transduced Gerbil Eyes

In a further study, the expression of aflibercept driven by the cassettes C7, C11, C12, C13, C14, were compared in vivo in gerbils. AAV vectors were assembled as described in Example 4. In addition, AAV7m8 capsids were assembled containing the MNTC expression cassette expressing codon-optomized aflibercept. Groups of 8 animals received bilateral intravitreal (IVT) injections of either vehicle, AAV.7m8-C7-Co-Aflibercept, AAV.7m8-C11-Co-Aflibercept, AAV.7m8-C12-Co-Aflibercept, AAV.7m8-C13-Co-Aflibercept, or AAV.7m8-C14-Co-Aflibercept, at $2 \times 10^{10}$ vg/eye. At 8 weeks and 16 weeks post-injection four animals were sacrificed, dissected into (i) the retina, (ii) the vitreous, (iii) the retina/choroid, and (iv) the iris/ciliary body, and Aflibercept expression was analyzed in each eye (eight eyes total per group per time point).

Free Aflibercept expression was measured in tissue samples using a modified sandwich-type ELISA. Specifically, microtiter plates were coated with recombinant human VEGF protein. Protein samples were incubated in each well, which was subsequently washed. After washing, a horseradish peroxidase (HRP) conjugated anti-human IgG monoclonal antibody was added to each well. The antibody binds to the Fc domain of the Aflibercept protein, which itself was captured by the VEGF bound to the surface of the well. Following incubation, wells were washed and bound enzymatic activity was determined by the addition of Luminol followed by measurement of light emission at 466 nm.

Expression was detected from each construct in each of the tissue samples examined at both 8 and 16 meek time points, and was highest in the vitreous for each construct at both time points.

TABLE 1

| POLYNUCLEOTIDE SEQUENCE OF CASSETTE 10 | | | |
|---|---|---|---|
| Element | Source | Sequence (5' to 3') | SEQ ID NO: |
| First Enhancer | CMV | ACTTACGGTAAATGGCCCGCCTGGC<br>TGACCGCCCAACGACCCCCGCCCAT<br>TGACGTCAATAATGACGTATGTTCC<br>CATAGTAACGCCAATAGGGACTTTC<br>CATTGACGTCAATGGGTGGAGTATT<br>TACGGTAAACTGCCCACTTGGCAGT<br>ACATCAAGTGTATCATATGCCAAGT<br>CCGCCCCCTATTGACGTCAATGACG<br>GTAAATGGCCCGCCTGGCATTATGC<br>CCAGTACATGACCTTACGGGACTTT<br>CCTACTTGGCAGTACATCTACGTATT<br>AGTCATCGCTATTACCA | 1 |
| Promoter | EF1α | GCACATCGCCCACAGTCCCCGAGA<br>AGTTGGGGGGAGGGGTCGGCAATT<br>GAACCGGTGCCTAGAGAAGGTGGC<br>GCGGGGTAAACTGGGAAAGTGATG<br>TCGTGTACTGGCTCCGCCTTTTTCCC<br>GAGGGTGGGGGAGAACCGTATATAA<br>GTGCAGTAGTCGCCGTGAACGTTC | 3 |
| Intron | EF1α | GTAAGTGCCGTGTGTGGTTCCCGCG<br>GGCCTGGCCTCTTTACGGGTTATGG<br>CCCTTGCGTGCCTTGAATTACTTCC<br>ACCTGGCTCCAGTACGTGATTCTTG<br>ATCCCGAGCTGGAGCCAGGGGCGG<br>GCCTTGCGCTTTAGGAGCCCCTTCG<br>CCTCGTGCTTGAGTTGAGGCCTGGC<br>CTGGGCGCTGGGGCCGCCGCGTGC<br>GAATCTGGTGGCACCTTCGCGCCTG<br>TCTCGCTGCTTTCGATAAGTCTCTAG<br>CCATTTAAAATTTTTGATGACGTGCT<br>GCGACGCTTTTTTTCTGGCAAGATA<br>GTCTTGTAAATGCGGGCCAGGATCT<br>GCACACTGGTATTTCGGTTTTTGGG<br>CCCGCGGCCGGCGACGGGGCCCGT<br>GCGTCCCAGCGCACATGTTCGGCGA<br>GGCGGGGCCTGCGAGCGCGGCCAC<br>CGAGAATCGACGGGGGTAGTCTC<br>AAGCTGGCCGGCCTGCTCTGGTGCC<br>TGGCCTCGCGCCGCCGTGTATCGCC<br>CCGCCCTGGGCGGCAAGGCTGGCC<br>CGGTCGGCACCAGTTGCGTGAGCG<br>GAAAGATGGCCGCTTCCCGGCCCTG<br>CTCCAGGGGGCTCAAAATGGAGGA<br>CGCGGCGCTCGGGAGAGCGGGCGG<br>GTGAGTCACCCACACAAAGGAAAA<br>GGGCCTTTCCGTCCTCAGCCGTCGC<br>TTCATGTGACTCCACGGAGTACCGG<br>GCGCCGTCCAGGCACCTCGATTAGT<br>TCTGGAGCTTTTGGAGTACGTCGTC<br>TTTAGGTTGGGGGGAGGGGTTTTAT | 5 |

TABLE 1-continued

POLYNUCLEOTIDE SEQUENCE OF CASSETTE 10

| Element | Source | Sequence (5' to 3') | SEQ ID NO: |
|---|---|---|---|
| | | GCGATGGAGTTTCCCCACACTGAGT<br>GGGTGGAGACTGAAGTTAGGCCAG<br>CTTGGCACTTGATGTAATTCTCCTTG<br>GAATTTGGCCTTTTTGAGTTTGGAT<br>CTTGGTTCATTCTCAAGCCTCAGAC<br>AGTGGTTCAAAGTTTTTTTCTTCCAT<br>TTCAG | |
| 5'UTR | UTR2 | ACACCCAAGCTGTCTAGAGCCGCC<br>ACC | 6 |
| Coding<br>Sequence | Gene of<br>Interest | Transgene | |
| Second<br>Enhancer | 511-810<br>EES | GGTTCCCTTTTATTTTTTACATATAAA<br>TATATTTCCCTGTTTTTCTAAAAAAG<br>AAAAAGATCATCATTTTCCCATTGTA<br>AAATGCCATATTTTTTTCATAGGTCA<br>CTTACATATATCAATGGGTCTGTTTC<br>TGAGCTCTACTCTATTTTATCAGCCT<br>CACTGTCTATCCCCACACATCTCATG<br>CTTTGCTCTAAATCTTGATATTTAGT<br>GGAACATTCTTTCCCATTTTGTTCTA<br>CAAGAATATTTTTGTTATTGTCTTTG<br>GGCTTTCTATATACATTTTGAAATGA<br>GGTTGACAAGTTA | 7 |
| RNA Export | WPRE | AATCAACCTCTGGATTACAAAATTT<br>GTGAAAGATTGACTGGTATTCTTAA<br>CTATGTTGCTCCTTTTACGCTATGTG<br>GATACGCTGCTTTAATGCCTTTGTAT<br>CATGCTATTGCTTCCCGTATGGCTTT<br>CATTTTCTCCTCCTTGTATAAATCCT<br>GGTTGCTGTCTCTTTATGAGGAGTT<br>GTGGCCCGTTGTCAGGCAACGTGG<br>CGTGGTGTGCACTGTGTTTGCTGAC<br>GCAACCCCACTGGTTGGGGCATTG<br>CCACCACCTGTCAGCTCCTTTCCGG<br>GACTTTCGCTTTCCCCCTCCCTATTG<br>CCACGGCGGAACTCATCGCCGCCTG<br>CCTTGCCCGCTGCTGGACAGGGGCT<br>CGGCTGTTGGGCACTGACAATTCCG<br>TGGTGTTGTCGGGGAAATCATCGTC<br>CTTTCCTTGGCTGCTCGCCTGTGTT<br>GCCACCTGGATTCTGCGCGGGACGT<br>CCTTCTGCTACGTCCCTTCGGCCCT<br>CAATCCAGCGGACCTTCCTTCCCGC<br>GGCCTGCTGCCGGCTCTGCGGCCTC<br>TTCCGCCTCTTCGCCTTCGCCCTCA<br>GACGAGTCGGATCTCCCTTTGGGCC<br>GCCTCCCCGC | 8 |
| PolyA | BGH | TTGCCAGCCATCTGTTGTTTGCCCC<br>TCCCCCGTGCCTTCCTTGACCCTGG<br>AAGGTGCCACTCCCACTGTCCTTTC<br>CTAATAAAATGAGGAAATTGCATCG<br>CATTGTCTGAGTAGGTGTCATTCTAT<br>TCTGGGGGGTGGGGTGGGGCAGGA<br>CAGCAAGGGGGAGGATTGGGAATA<br>CAATAGCAGGCATGCTGGGGATGCG<br>GTGGGCTCTATGGGTACCCAGGTGC<br>TGAAGAATTGACCCGGTTCCTCCTG<br>GG | 9 |

TABLE 2

POLYNUCLEOTIDE SEQUENCE OF CASSETTE 11

| Element | Source | Sequence (5' to 3') | SEQ ID NO: |
|---|---|---|---|
| 5'ITR | AAV | GCGCGCTCGCTCGCTCACTGAGGCC<br>GCCCGGGCAAAGCCCGGGCGTCGG<br>GCGACCTTTGGTCGCCCGGCCTCAG | 10 |

TABLE 2-continued

POLYNUCLEOTIDE SEQUENCE OF CASSETTE 11

| Element | Source | Sequence (5' to 3') | SEQ ID NO: |
|---|---|---|---|
| | | TGAGCGAGCGAGCGCGCAGAGAGG GAGTGGCCAACTCCATCACTAGGGG TTCC | |
| First Enhancer | CMV | ACTTACGGTAAATGGCCCGCCTGGC TGACCGCCCAACGACCCCCGCCCAT TGACGTCAATAATGACGTATGTTCC CATAGTAACGCCAATAGGGACTTTC CATTGACGTCAATGGGTGGAGTATT TACGGTAAACTGCCCACTTGGCAGT ACATCAAGTGTATCATATGCCAAGT CCGCCCCCTATTGACGTCAATGACG GTAAATGGCCCGCCTGGCATTATGC CCAGTACATGACCTTACGGGACTTT CCTACTTGGCAGTACATCTACGTATT AGTCATCGCTATTACCA | 1 |
| Promoter | CMV | TGCTGATGCGGTTTTGGCAGTACAC CAATGGGCGTGGATAGCGGTTTGAC TCACGGGGATTTCCAAGTCTCCACC CCATTGACGTCAATGGGAGTTTGTT TTGGCACCAAAATCAACGGGACTTT CCAAAATGTCGTAATAACCCCGCCC CGTTGACGCAAATGGGCGGTAGGC GTGTACGGTGGGAGGTCTATATAAG CAGAGCTCGTTTAGTGAACCG | 4 |
| 5'UTR | TPL | CTCACTCTCTTCCGCATCGCTGTCT GCGAGGGCCAGCTGTTGGGCTCGC GGTTGAGGACAAACTCTTCGCGGT CTTTCCAGTACTCTTGGATCGGAAA CCCGTCGGCCTCCGAACGGTACTCC GCCACCGAGGGACCTGAGCGAGTC CGCATCGACCGGATCGGAAAACCTC TCGAGAAAGGCGTCTAACCAGTCA CAGTCGCAAGGTAGGCTGAGCACC GTGGCGGGCGGCAGCGGGTGGCGG TCGGGGTTGTTTCTGGCGGAGGTGC TGCTGATGATGTAATTAAAGTAGGC GGTCTTGAGACGGCGGATGGTCGA | 11 |
| 5'UTR | eMLP | CCAGCTGTTGGGGTGAGTACTCCCT CTCAAAAGCGGGCATTACTTCTGCG CTAAGATTGTCAGTTTCCAAAAACG AGGAGGATTTGATATTCACCTGGCC CG | 12 |
| Coding Sequence | Gene of Interest | Transgene | |
| Second Enhancer | Full EES | CTGTTCTCATCACATCATATCAAGGT TATATACCATCAATATTGCCACAGAT GTTACTTAGCCTTTTAATATTTCTCT AATTTAGTGTATATGCAATGATAGTT CTCTGATTTCTGAGATTGAGTTTCTC ATGTGTAATGATTATTTAGAGTTTCT CTTTCATCTGTTCAAATTTTTGTCTA GTTTTATTTTTTACTGATTTGTAAGA CTTCTTTTTATAATCTGCATATTACAA TTCTCTTTACTGGGGTGTTGCAAATA TTTTCTGTCATTCTATGGCCTGACTT TTCTTAATGGTTTTTTAATTTTAAAA ATAAGTCTTAATATTCATGCAATCTA ATTAACAATCTTTTCTTTGTGGTTAG GACTTTGAGTCATAAGAAATTTTTC TCTACACTGAAGTCATGATGGCATG CTTCTATATTATTTTCTAAAAGATTTA AAGTTTTGCCTTCTCCATTTAGACTT ATAATTCACTGGAATTTTTTGTGTG TATGGTATGACATATGGGTTCCCTTT TATTTTTTACATATAAATATATTTCCC TGTTTTTCTAAAAAGAAAAAGATC ATCATTTTCCCATTGTAAAATGCCAT ATTTTTTTCATAGGTCACTTACATATA TCAATGGGTCTGTTTCTGAGCTCTA CTCTATTTTATCAGCCTCACTGTCTA | 13 |

TABLE 2-continued

POLYNUCLEOTIDE SEQUENCE OF CASSETTE 11

| Element | Source | Sequence (5' to 3') | SEQ ID NO: |
|---|---|---|---|
| | | TCCCCACACATCTCATGCTTTGCTCT AAATCTTGATATTTAGTGGAACATTC TTTCCCATTTTGTTCTACAAGAATAT TTTTGTTATTGTCTTTGGGCTTTCTAT ATACATTTTGAAATGAGGTTGACAA GTTA | |
| Poly A Sequence | HGH | CTGCCCGGGTGGCATCCCTGTGACC CCTCCCCAGTGCCTCTCCTGGCCCT GGAAGTTGCCACTCCAGTGCCCAC CAGCCTTGTCCTAATAAAATTAAGTT GCATCATTTTGTCTGACTAGGTGTCC TTCTATAATATTATGGGGTGGAGGGG GGTGGTATGGAGCAAGGGGCCCAA GTTGGGAAGAAACCTGTAGGGCCT GC | 14 |
| 3'ITR | AAV | GTTAATCATTAACTACAAGGAACCC CTAGTGATGGAGTTGGCCACTCCCT CTCTGCGCGCTCGCTCGCTCACTGA GGCCGGGCGACCAAAGGTCGCCCG ACGCCCGGGCTTTGCCCGGGCGGC CTCAGTGAGCGAGCGAGCGCGC | 15 |

TABLE 3

POLYNUCLEOTIDE SEQUENCE OF CASSETTE 12

| Element | Source | Sequence (5' to 3') | SEQ ID NO: |
|---|---|---|---|
| First Enhancer | CMV | ACTTACGGTAAATGGCCCGCCTGGC TGACCGCCCAACGACCCCCGCCCAT TGACGTCAATAATGACGTATGTTCC CATAGTAACGCCAATAGGGACTTTC CATTGACGTCAATGGGTGGAGTATT TACGGTAAACTGCCCACTTGGCAGT ACATCAAGTGTATCATATGCCAAGT CCGCCCCCTATTGACGTCAATGACG GTAAATGGCCCGCCTGGCATTATGC CCAGTACATGACCTTACGGGACTTT CCTACTTGGCAGTACATCTACGTATT AGTCATCGCTATTACCA | 1 |
| Promoter | CMV | TGCTGATGCGGTTTTGGCAGTACAC CAATGGGCGTGGATAGCGGTTTGAC TCACGGGGATTTCCAAGTCTCCACC CCATTGACGTCAATGGGAGTTTGTT TTGGCACCAAAATCAACGGGACTTT CCAAAATGTCGTAATAACCCCGCCC CGTTGACGCAAATGGGCGGTAGGC GTGTACGGTGGGAGGTCTATATAAG CAGAGCTCGTTTAGTGAACCG | 4 |
| 5'UTR | TPL | CTCACTCTCTTCCGCATCGCTGTCT GCGAGGGCCAGCTGTTGGGCTCGC GGTTGAGGACAAACTCTTCGCGGT CTTTCCAGTACTCTTGGATCGGAAA CCCGTCGGCCTCCGAACGGTACTCC GCCACCGAGGGACCTGAGCGAGTC CGCATCGACCGGATCGGAAAACCTC TCGAGAAAGGCGTCTAACCAGTCA CAGTCGCAAGGTAGGCTGAGCACC GTGGCGGGCGGCAGCGGGTGGCGG TCGGGGTTGTTTCTGGCGGAGGTGC TGCTGATGATGTAATTAAAGTAGGC GGTCTTGAGACGGCGGATGGTCGA | 11 |
| 5'UTR | eMLP | CCAGCTGTTGGGGTGAGTACTCCCT CTCAAAAGCGGGCATTACTTCTGCG CTAAGATTGTCAGTTTCCAAAAACG AGGAGGATTTGATATTCACCTGGCC CG | 12 |

TABLE 3-continued

POLYNUCLEOTIDE SEQUENCE OF CASSETTE 12

| Element | Source | Sequence (5' to 3') | SEQ ID NO: |
|---|---|---|---|
| Coding Sequence | Gene of Interest | Transgene | |
| Second Enhancer | 410-564 EES | GGCATGCTTCTATATTATTTTCTAAA AGATTTAAAGTTTTGCCTTCTCCATT TAGACTTATAATTCACTGGAATTTTT TTGTGTGTATGGTATGACATATGGGT TCCCTTTTATTTTTTACATATAAATAT ATTTCCCTGTTTTTCTAAAAAAGA | 16 |
| RNA Export | HPRE | ATAACAGGCCTATTGATTGGAAAGT TTGTCAACGAATTGTGGGTCTTTTG GGGTTTGCTGCCCCTTTTACGCAAT GTGGATATCCTGCTTTAATGCCTTTA TATGCATGTATACAAGCAAAACAGG CTTTTACTTTCTCGCCAACTTACAA GGCCTTTCTCAGTAAACAGTATATG ACCCTTTACCCCGTTGCTCGGCAAC GGCCTGGTCTGTGCCAAGTGTTTGC TGACGCAACCCCCACTGGTTGGGG CTTGGCCATAGGCCATCAGCGCATG CGTGGAACCTTTGTGTCTCCTCTGC CGATCCATACTGCGGAACTCCTAGC CGCTTGTTTTGCTCGCAGCAGGTCT GGAGCAAACCTCATCGGGACCGAC AATTCTGTCGTACTCTCCCGCAAGT ATACATCGTTTCCATGGCTGCTAGGC TGTGCTGCCAACTGGATCCTGCGCG GGACGTCCTTTGTTTACGTCCCGTC GGCGCTGAATCCCGCGGACGACCC CTCCCGGGGCCGCTTGGGGCTCTAC CGCCCGCTTCTCCGTCTGCCGTACC GTCCGACCACGGGGCGCACCTCTCT TTACGCGGACTCCCCGTCTGTGCCT TCTCATCTGCCGGACCGTGTGCACT TCGCTTCACCTCTGCACGTCGCATG GAGGCCACCGTGAACGCCCACCGG AACCTGCCCAAGGTCTTGCATAAGA GGACTCTTGGACTTTCAGCAATGTC ATC | 17 |
| PolyA | BGH | TTGCCAGCCATCTGTTGTTTGCCCC TCCCCCGTGCCTTCCTTGACCCTGG AAGGTGCCACTCCCACTGTCCTTTC CTAATAAAATGAGGAAATTGCATCG CATTGTCTGAGTAGGTGTCATTCTAT TCTGGGGGGTGGGGTGGGGCAGGA CAGCAAGGGGGAGGATTGGGAATA CAATAGCAGGCATGCTGGGGATGCG GTGGGCTCTATGGGTACCCAGGTGC TGAAGAATTGACCCGGTTCCTCCTG GG | 9 |

TABLE 4

POLYNUCLEOTIDE SEQUENCE OF CASSETTE 14

| Element | Source | Sequence (5' to 3') | SEQ ID NO: |
|---|---|---|---|
| First Enhancer | CMV | ACTTACGGTAAATGGCCCGCCTGGC TGACCGCCCAACGACCCCCGCCCAT TGACGTCAATAATGACGTATGTTCC CATAGTAACGCCAATAGGGACTTTC CATTGACGTCAATGGGTGGAGTATT TACGGTAAACTGCCCACTTGGCAGT ACATCAAGTGTATCATATGCCAAGT CCGCCCCCTATTGACGTCAATGACG GTAAATGGCCCGCCTGGCATTATGC CCAGTACATGACCTTACGGGACTTT CCTACTTGGCAGTACATCTACGTATT AGTCATCGCTATTACCA | 1 |

TABLE 4-continued

POLYNUCLEOTIDE SEQUENCE OF CASSETTE 14

| Element | Source | Sequence (5' to 3') | SEQ ID NO: |
|---|---|---|---|
| Promoter | CMV | TGCTGATGCGGTTTTGGCAGTACAC<br>CAATGGGCGTGGATAGCGGTTTGAC<br>TCACGGGGATTTCCAAGTCTCCACC<br>CCATTGACGTCAATGGGAGTTTGTT<br>TTGGCACCAAAATCAACGGGACTTT<br>CCAAAATGTCGTAATAACCCCGCCC<br>CGTTGACGCAAATGGGCGGTAGGC<br>GTGTACGGTGGGAGGTCTATATAAG<br>CAGAGCTCGTTTAGTGAACCG | 4 |
| Intron | CMVc | GTAAGTCTGTTGACATGTATGTGAT<br>GTATACTAACCTGCATGGGACGTGG<br>ATTTACTTGTGTATGTCAGATAGAGT<br>AAAGATTAACTCTTGCATGTGAGCG<br>GGGCATCGAGATAGCGATAAATGAG<br>TCAGGAGGACGGATACTTATATGTG<br>TTGTTATCCTCCTCTACAG | 18 |
| 5'UTR | UTR1 | AGCTTGCTTGTTCTTTTTGCAGAAG<br>CTCAGAATAAACGCTCAACTTTGGC | 19 |
| Coding Sequence | Gene of Interest | Transgene | |
| Second Enhancer | Full EES | CTGTTCTCATCACATCATATCAAGGT<br>TATATACCATCAATATTGCCACAGAT<br>GTTACTTAGCCTTTTAATATTTCTCT<br>AATTTAGTGTATATGCAATGATAGTT<br>CTCTGATTTCTGAGATTGAGTTTCTC<br>ATGTGTAATGATTATTTAGAGTTTCT<br>CTTTCATCTGTTCAAATTTTTGTCTA<br>GTTTTATTTTTTACTGATTTGTAAGA<br>CTTCTTTTTATAATCTGCATATTACAA<br>TTCTCTTTACTGGGGTGTTGCAAATA<br>TTTTCTGTCATTCTATGGCCTGACTT<br>TTCTTAATGGTTTTTTAATTTTAAAA<br>ATAAGTCTTAATATTCATGCAATCTA<br>ATTAACAATCTTTTCTTTGTGGTTAG<br>GACTTTGAGTCATAAGAAATTTTTC<br>TCTACACTGAAGTCATGATGGCATG<br>CTTCTATATTATTTTCTAAAAGATTTA<br>AAGTTTTGCCTTCTCCATTTAGACTT<br>ATAATTCACTGGAATTTTTTTGTGTG<br>TATGGTATGACATATGGGTTCCCTTT<br>TATTTTTTACATATAAATATATTTCCC<br>TGTTTTTCTAAAAAAGAAAAAGATC<br>ATCATTTTCCCATTGTAAAATGCCAT<br>ATTTTTTTCATAGGTCACTTACATATA<br>TCAATGGGTCTGTTTCTGAGCTCTA<br>CTCTATTTTATCAGCCTCACTGTCTA<br>TCCCCACACATCTCATGCTTTGCTCT<br>AAATCTTGATATTTAGTGGAACATTC<br>TTTCCCATTTTGTTCTACAAGAATAT<br>TTTTGTTATTGTCTTTGGGCTTTCTAT<br>ATACATTTTGAAATGAGGTTGACAA<br>GTTA | 13 |
| RNA Export | WPRE | AATCAACCTCTGGATTACAAAATTT<br>GTGAAAGATTGACTGGTATTCTTAA<br>CTATGTTGCTCCTTTTACGCTATGTG<br>GATACGCTGCTTTAATGCCTTTGTAT<br>CATGCTATTGCTTCCCGTATGGCTTT<br>CATTTTCTCCTCCTTGTATAAATCCT<br>GGTTGCTGTCTCTTTATGAGGAGTT<br>GTGGCCCGTTGTCAGGCAACGTGG<br>CGTGGTGTGCACTGTGTTTGCTGAC<br>GCAACCCCCACTGGTTGGGGCATTG<br>CCACCACCTGTCAGCTCCTTTCCGG<br>GACTTTCGCTTTCCCCCTCCCTATTG<br>CCACGGCGGAACTCATCGCCGCTG<br>CCTTGCCCGCTGCTGGACAGGGGCT<br>CGGCTGTTGGGCACTGACAATTCCG<br>TGGTGTTGTCGGGGAAATCATCGTC<br>CTTTCCTTGGCTGCTCGCCTGTGTT<br>GCCACCTGGATTCTGCGCGGGACGT | 8 |

TABLE 4-continued

POLYNUCLEOTIDE SEQUENCE OF CASSETTE 14

| Element | Source | Sequence (5' to 3') | SEQ ID NO: |
|---|---|---|---|
| | | CCTTCTGCTACGTCCCTTCGGCCCT<br>CAATCCAGCGGACCTTCCTTCCCGC<br>GGCCTGCTGCCGGCTCTGCGGCCTC<br>TTCCGCCTCTTCGCCTTCGCCCTCA<br>GACGAGTCGGATCTCCCTTTGGGCC<br>GCCTCCCCGC | |
| PolyA | Rabbit β-globin polyA | TGGCTAATAAAGGAAATTTATTTTCA<br>TTGCAATAGTGTGTTGGAATTTTTTG<br>TGTCTCTCACTCGGAAGGACATATG<br>GGAGGGCAAATCATTTAAAACATCA<br>GAATGAGTATTTGGTTTAGAGTTTG<br>GCAACATATGCCCATATGCTGGCTG<br>CCATGAACAAAGGTTGGCTATAAAG<br>AGGTCATCAGTATATGAAACAGCCC<br>CCTGCTGTCCATTCCTTATTCCATAG<br>AAAAGCCTTGACTTGAGGTTAGATT<br>TTTTTTATATTTTGTTTTGTGTTATTT<br>TTTTCTTTAACATCCCTAAAATTTTC<br>CTTACATGTTTTACTAGCCAGATTTT<br>TCCTCCTCTCCTGACTACTCCCAGT<br>CATAGCTGTCCCTCTTCTCTTATGGA<br>GATC | 20 |

TABLE 5

POLYNUCLEOTIDE SEQUENCE OF THE CMV REFERENCE CONTROL CASSETTE (CMV-sFLT1)

| Element | Source | Sequence (5' to 3') | SEQ ID NO: |
|---|---|---|---|
| Enhancer | CMV | TCAATATTGGCCATTAGCCATATTATTCATT<br>GGTTATATAGCATAAATCAATATTGGCTATT<br>GGCCATTGCATACGTTGTATCTATATCATAA<br>TATGTACATTTATATTGGCTCATGTCCAATA<br>TGACCGCCATGTTGGCATTGATTATTGACT<br>AGTTATTAATAGTAATCAATTACGGGGTCA<br>TTAGTTCATAGCCCATATATGGAGTTCCGC<br>GTTACATAACTTACGGTAAATGGCCCGCCT<br>GGCTGACCGCCCAACGACCCCCGCCCATT<br>GACGTCAATAATGACGTATGTTCCCATAGT<br>AACGCCAATAGGGACTTTCCATTGACGTC<br>AATGGGTGGAGTATTTACGGTAAACTGCCC<br>ACTTGGCAGTACATCAAGTGTATCATATGC<br>CAAGTCCGCCCCCTATTGACGTCAATGAC<br>GGTAAATGGCCCGCCTGGCATTATGCCCAG<br>TACATGACCTTACGGGACTTTCCTACTTGG<br>CAGTACATCTACGTATTAGTCATCGCTATTA<br>CCATGGTGATGCGGTTTTGGCAGTACACC<br>AATGGGCGTGGATAGCGGTTTGACTCACG<br>GGGATTTCCAAGTCTCCACCCCATTGACGT<br>CAATGGGAGTTTGTTTTGGCACCAAAATC<br>AACGGGACTTTCCAAAATGTCGTAATAAC<br>C | 2 |
| Promoter | CMV | CCGCCCCGTTGACGCAAATGGGCGGTAGG<br>CGTGTACGGTGGGAGGTCTATATAAGCAG<br>AGCTCGTTTAGTGAACCGTCAGATC | 21 |
| Intron | Chimeric Intron | GTAAGTATCAAGGTTACAAGACAGGTTTA<br>AGGAGACCAATAGAAACTGGGCTTGTCGA<br>GACAGAGAAGACTCTTGCGTTTCTGATAG<br>GCACCTATTGGTCTTACTGACATCCACTTT<br>GCCTTTCTCTCCACAG | 22 |
| 5'UTR | | GGGGCTCGGGTGCAGCGGCCAGCGGGCG<br>CCTGGCGGCGAGGATTACCCGGGGAAGTG<br>GTTGTCTCCTGGCTGGAGCCGCGAGACGG<br>GCGCTCAGGGCGCGGGGCCGGCGGCGGC<br>GAACGAGAGGACGGACTCTGGCGGCCGG<br>GTCTTTGGCCGCGGGGAGCGCGGGCACCG<br>GGCGAGCAGGCCGCGTCGCGCTCACC | 23 |

TABLE 5-continued

POLYNUCLEOTIDE SEQUENCE OF THE CMV REFERENCE CONTROL CASSETTE (CMV-sFLT1)

| Element | Source | Sequence (5' to 3') | SEQ ID NO: |
|---|---|---|---|
| Coding Sequence | sFLT-1 | ATGGTCAGCTACTGGGACACCGGGGTCCT | 24 |
| | | GCTGTGCGCGCTGCTCAGCTGTCTGCTTCT | |
| | | CACAGGATCTAGTTCAGGTTCAAAATTAA | |
| | | AAGATCCTGAACTGAGTTTAAAAGGCACC | |
| | | CAGCACATCATGCAAGCAGGCCAGACACT | |
| | | GCATCTCCAATGCAGGGGGGAAGCAGCCC | |
| | | ATAAATGGTCTTTGCCTGAAATGGTGAGTA | |
| | | AGGAAAGCGAAAGGCTGAGCATAACTAAA | |
| | | TCTGCCTGTGGAAGAAATGGCAAACAATT | |
| | | CTGCAGTACTTTAACCTTGAACACAGCTC | |
| | | AAGCAAACCACACTGGCTTCTACAGCTGC | |
| | | AAATATCTAGCTGTACCTACTTCAAAGAAG | |
| | | AAGGAAACAGAATCTGCAATCTATATATTT | |
| | | ATTAGTGATACAGGTAGACCTTTCGTAGAG | |
| | | ATGTACAGTGAAATCCCCGAAATTATACAC | |
| | | ATGACTGAAGGAAGGGAGCTCGTCATTCC | |
| | | CTGCCGGGTTACGTCACCTAACATCACTGT | |
| | | TACTTTAAAAAAGTTTCCACTTGACACTTT | |
| | | GATCCCTGATGGAAAACGCATAATCTGGG | |
| | | ACAGTAGAAAGGGCTTCATCATATCAAATG | |
| | | CAACGTACAAAGAAATAGGGCTTCTGACC | |
| | | TGTGAAGCAACAGTCAATGGGCATTTGTAT | |
| | | AAGACAAACTATCTCACACATCGACAAAC | |
| | | CAATACAATCATAGATGTCCAAATAAGCAC | |
| | | ACCACGCCCAGTCAAATTACTTAGAGGCC | |
| | | ATACTCTTGTCCTCAATTGTACTGCTACCA | |
| | | CTCCCTTGAACACGAGAGTTCAAATGACC | |
| | | TGGAGTTACCCTGATGAAAAAAATAAGAG | |
| | | AGCTTCCGTAAGGCGACGAATTGACCAAA | |
| | | GCAATTCCCATGCCAACATATTCTACAGTG | |
| | | TTCTTACTATTGACAAAATGCAGAACAAA | |
| | | GACAAAGGACTTTATACTTGTCGTGTAAG | |
| | | GAGTGGACCATCATTCAAATCTGTTAACAC | |
| | | CTCAGTGCATATATATGATAAAGCATTCATC | |
| | | ACTGTGAAACATCGAAAACAGCAGGTGCT | |
| | | TGAAACCGTAGCTGGCAAGCGGTCTTACC | |
| | | GGCTCTCTATGAAAGTGAAGGCATTTCCCT | |
| | | CGCCGGAAGTTGTATGGTTAAAAGATGGG | |
| | | TTACCTGCGACTGAGAAATCTGCTCGCTAT | |
| | | TTGACTCGTGGCTACTCGTTAATTATCAAG | |
| | | GACGTAACTGAAGAGGATGCAGGGAATTA | |
| | | TACAATCTTGCTGAGCATAAAACAGTCAA | |
| | | ATGTGTTTAAAAACCTCACTGCCACTCTAA | |
| | | TTGTCAATGTGAAACCCCAGATTTACGAA | |
| | | AAGGCCGTGTCATCGTTTCCAGACCCGGC | |
| | | TCTCTACCCACTGGGCAGCAGACAAATCC | |
| | | TGACTTGTACCGCATATGGTATCCCTCAAC | |
| | | CTACAATCAAGTGGTTCTGGCACCCCTGTA | |
| | | ACCATAATCATTCCGAAGCAAGGTGTGAC | |
| | | TTTTGTTCCAATAATGAAGAGTCCTTTATC | |
| | | CTGGATGCTGACAGCAACATGGGAAACAG | |
| | | AATTGAGAGCATCACTCAGCGCATGGCAA | |
| | | TAATAGAAGGAAAGAATAAGATGGCTAGC | |
| | | ACCTTGGTTGTGGCTGACTCTAGAATTTCT | |
| | | GGAATCTACATTTGCATAGCTTCCAATAAA | |
| | | GTTGGGACTGTGGGAAGAAACATAAGCTT | |
| | | TTATATCACAGATGTGCCAAATGGGTTTCA | |
| | | TGTTAACTTGGAAAAAATGCCGACGGAAG | |
| | | GAGAGGACCTGAAACTGTCTTGCACAGTT | |
| | | AACAAGTTCTTATACAGAGACGTTACTTGG | |
| | | ATTTTACTGCGGACAGTTAATAACAGAACA | |
| | | ATGCACTACAGTATTAGCAAGCAAAAAAT | |
| | | GGCCATCACTAAGGAGCACTCCATCACTC | |
| | | TTAATCTTACCATCATGAATGTTTCCCTGCA | |
| | | AGATTCAGGCACCTATGCCTGCAGAGCCA | |
| | | GGAATGTATACACAGGGGAAGAAATCCTC | |
| | | CAGAAGAAAGAAATTACAATCAGAGGTGA | |
| | | GCACTGCAACAAAAAGGCTGTTTTCTCTC | |

TABLE 5-continued

POLYNUCLEOTIDE SEQUENCE OF THE CMV REFERENCE
CONTROL CASSETTE (CMV-sFLT1)

| Element | Source | Sequence (5' to 3') | SEQ ID NO: |
|---|---|---|---|
| | | GGATCTCCAAATTTAAAAGCACAAGGAAT GATTGTACCACACAAAGTAATGTAAAACAT TAA | |
| 3'UTR | | AGGACTCATTAAAAAGTAAC | 25 |
| PolyA | SV40 | CAGACATGATAAGATACATTGATGAGTTTG GACAAACCACAACTAGAATGCAGTGAAA AAAATGCTTTATTTGTGAAATTTGTGATGC TATTGCTTTATTTGTAACCATTATAAGCTGC AATAAACAAGTTAACAACAACAATTGCAT TCATTTTATGTTTCAGGTTCAGGGGGAGAT GTGGGAGGTTTTTTAAAGCAAGTAAAACC TCTACAAATGTGGTA | 26 |

Inverted terminal repeat (ITR) sequences from AAV may be placed in flanking positions around any of the cassettes for subsequent transfer of the cassette to an AAV genome, as exemplified for cassette 11. A Kozak sequence (e.g., GCCACC) may occur 5' of the start codon of the coding sequence. The CMV reference control cassette may comprise any transgene of interest. Table 5 shows one illustrative embodiment, wherein the transgene encodes sFLT-1.

What is claimed is:

1. A non-naturally occurring polynucleotide cassette comprising in 5' to 3' order:
   (a) a first enhancer region comprising a CMV sequence consisting of SEQ ID NO:1 or a sequence having at least 99% identity to SEQ ID NO:1;
   (b) a promoter region comprising a CMV sequence consisting of SEQ ID NO:4 or a sequence having at least 99% identity to SEQ ID NO:4;
   (c) a 5'UTR region comprising, in 5' to 3' order, a tripartite leader (TPL) sequence consisting of SEQ ID NO:11 or a sequence having at least 99% identity to SEQ ID NO:11, an enhancer element from the adenovirus major late promoter (eMLP) sequence consisting of SEQ ID NO:12 or a sequence having at least 99% identity to SEQ ID NO:12, a mammalian intron acceptor, and a Kozak sequence;
   (d) a coding sequence encoding a secretory polypeptide, wherein the coding sequence is codon optimized for translation in primates and operably linked to the promoter region;
   (e) an enhancer region comprising a full expression enhancer sequence (EES) sequence consisting of SEQ ID NO:13 or a sequence having at least 99% identity to SEQ ID NO:13; and
   (f) a human growth hormone (HGH) polyadenylation site consisting of SEQ ID NO:14 or a sequence having at least 99% identity to SEQ ID NO:14;
   and wherein:
   the first enhancer region (a), the promoter region (b), and the 5' UTR region (c) define a 5' arm;
   the second enhancer region (e), and the HGH polyadenylation site (f) define a 3' arm.

2. The polynucleotide cassette according to claim 1, wherein the cassette does not comprise an RNA export signal.

3. The polynucleotide cassette of claim 1, further comprising each of SEQ ID NOs: 76-80.

4. The polynucleotide cassette according to claim 1, wherein the 5' arm comprises a sequence with at least 99% identity to SEQ ID NO: 47.

5. The polynucleotide cassette according to claim 1, wherein the 5' arm consists of SEQ ID NO: 47.

6. The polynucleotide cassette according to claim 1, wherein the 3' arm comprises a sequence with at least 99% identity to SEQ ID NO: 48.

7. The polynucleotide cassette according to claim 1, wherein the 3' arm consists of SEQ ID NO: 48.

8. The polynucleotide cassette according to claim 4, wherein the 3' arm comprises a sequence with at least 99% identity to SEQ ID NO: 48.

9. The polynucleotide cassette according to claim 5, wherein the 3' arm consists of SEQ ID NO: 48.

10. The polynucleotide cassette of claim 1, wherein the secretory polypeptide is selected from the group consisting of soluble fms-like tyrosine kinase-1, a VEGF-binding fragment of sFLT-1, and aflibercept.

11. The polynucleotide cassette of claim 1, wherein the secretory polypeptide is aflibercept.

12. A recombinant adeno-associated virus comprising:
   a) a capsid protein, wherein the capsid protein is an AAV variant 7m8 capsid protein or is derived from the AAV variant 7m8 capsid protein, and
   b) an adeno-associated virus vector genome comprising the polynucleotide cassette according to claim 1.

13. The recombinant adeno-associated virus of claim 12, wherein the secretory polypeptide is aflibercept.

14. A pharmaceutical composition comprising the recombinant adeno-associated virus of claim 12 and a pharmaceutically acceptable excipient.

15. The pharmaceutical composition of claim 14, wherein the secretory polypeptide is aflibercept.

16. The polynucleotide cassette according to claim 1, wherein the 5' arm comprises a sequence with at least 99% identity to SEQ ID NO: 47, and wherein the 3' arm comprises a sequence with at least 99% identity to SEQ ID NO: 48.

17. The polynucleotide cassette according to claim 1, wherein the 5' arm comprises SEQ ID NO: 47, and wherein the 3' arm comprises SEQ ID NO: 48.

* * * * *

SEQUENCE LISTING

<160> NUMBER OF SEQ ID NOS: 97

<210> SEQ ID NO 1
<211> LENGTH: 293
<212> TYPE: DNA
<213> ORGANISM: Human cytomegalovirus

<400> SEQUENCE: 1

```
acttacggta aatggcccgc ctggctgacc gcccaacgac ccccgcccat tgacgtcaat      60
aatgacgtat gttcccatag taacgccaat agggactttc cattgacgtc aatgggtgga     120
gtatttacgg taaactgccc acttggcagt acatcaagtg tatcatatgc caagtccgcc     180
ccctattgac gtcaatgacg gtaaatggcc cgcctggcat tatgcccagt acatgacctt     240
acgggacttt cctacttggc agtacatcta cgtattagtc atcgctatta cca            293
```

<210> SEQ ID NO 2
<211> LENGTH: 659
<212> TYPE: DNA
<213> ORGANISM: Human cytomegalovirus

<400> SEQUENCE: 2

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccccgccc attgacgtca ataatgacgt atgttcccat     300
agtaacgcca tagggacttt ccattgacg tcaatgggtg gagtatttac ggtaaactgc      360
ccacttggca gtacatcaag tgtatcatat gccaagtccg cccctattg acgtcaatga     420 cggtaaatgg cccgcctggc attatgccca gtacatgacc ttacgggact tcctacttg     480 gcagtacatc tacgtattag tcatcgctat taccatggtg atgcggtttt ggcagtacac     540
caatgggcgt ggatagcggt ttgactcacg gggatttcca gtctccacc ccattgacgt     600 caatgggagt ttgttttggc accaaaatca acgggacttt ccaaaatgtc gtaataacc     659
```

<210> SEQ ID NO 3
<211> LENGTH: 171
<212> TYPE: DNA
<213> ORGANISM: Homo sapiens

<400> SEQUENCE: 3

```
gcacatcgcc cacagtcccc gagaagttgg ggggaggggt cggcaattga accggtgcct        60
agagaaggtg gcgcggggta aactgggaaa gtgatgtcgt gtactggctc cgcctttttc       120
ccgagggtgg gggagaaccg tatataagtg cagtagtcgc cgtgaacgtt c                171
```

<210> SEQ ID NO 4
<211> LENGTH: 220
<212> TYPE: DNA
<213> ORGANISM: Human cytomegalovirus

<400> SEQUENCE: 4

```
tgctgatgcg gttttggcag tacaccaatg ggcgtggata gcggtttgac tcacgggat        60 ttccaagtct ccaccccatt gacgtcaatg ggagtttgtt ttggcaccaa aatcaacggg      120
actttccaaa atgtcgtaat aaccccgccc cgttgacgca aatgggcggt aggcgtgtac      180
ggtgggaggt ctatataagc agagctcgtt tagtgaaccg                            220
```

<210> SEQ ID NO 5
<211> LENGTH: 923
<212> TYPE: DNA
<213> ORGANISM: Homo sapiens

<400> SEQUENCE: 5

```
gtaagtgccg tgtgtggttc ccgcgggcct ggcctcttta cgggttatgg cccttgcgtg        60
ccttgaatta cttccacctg gctccagtac gtgattcttg atcccgagct ggagccaggg      120
gcgggccttg cgctttagga gccccttcgc ctcgtgcttg agttgaggcc tggcctgggc      180
gctggggccg ccgcgtgcga atctggtggc accttcgcgc ctgtctcgct gctttcgata      240
agtctctagc catttaaaat ttttgatgac gtgctgcgac gctttttttc tggcaagata      300
gtcttgtaaa tgcgggccag gatctgcaca ctggtatttc ggttttttggg cccgcggccg      360 gcgacgggc ccgtgcgtcc cagcgcacat gttcggcgag gcgggcctg cgagcgcggc        420 caccgagaat cggacggggg tagtctcaag ctggccggcc tgctctggtg cctggcctcg      480
cgccgccgtg tatcgccccg ccctgggcgg caaggctggc ccggtcggca ccagttgcgt      540
gagcggaaag atggccgctt cccggccctg ctccagggg ctcaaaatgg aggacgcggc        600
gctcgggaga gcgggcgggt gagtcaccca cacaaaggaa aagggccttt ccgtcctcag      660
ccgtcgcttc atgtgactcc acggagtacc gggcgccgtc caggcacctc gattagttct      720
ggagcttttg gagtacgtcg tcttttaggtt ggggggaggg gttttatgcg atggagtttc      780
cccacactga gtgggtggag actgaagtta ggccagcttg gcacttgatg taattctcct      840
tggaatttgg ccttttttgag tttggatctt ggttcattct caagcctcag acagtggttc      900 aaagttttt tcttccattt cag                                                923
```

<210> SEQ ID NO 6
<211> LENGTH: 27
<212> TYPE: DNA
<213> ORGANISM: Homo sapiens

<400> SEQUENCE: 6

```
acacccaagc tgtctagagc cgccacc                                        27
```

<210> SEQ ID NO 7
<211> LENGTH: 300
<212> TYPE: DNA
<213> ORGANISM: Homo sapiens

<400> SEQUENCE: 7

```
ggttcccttt tatttttac atataaatat atttccctgt ttttctaaaa aagaaaaaga    60
tcatcattt cccattgtaa atgccatat tttttcata ggtcacttac atatatcaat     120
gggtctgttt ctgagctcta ctctatttta tcagcctcac tgtctatccc cacacatctc  180
atgctttgct ctaaatcttg atatttagtg aacattctt tcccattttg ttctacaaga   240
atattttgt tattgtctttt gggctttcta tatacatttt gaaatgaggt tgacaagtta  300
```

<210> SEQ ID NO 8
<211> LENGTH: 589
<212> TYPE: DNA
<213> ORGANISM: Woodchuck hepatitis virus

<400> SEQUENCE: 8

```
aatcaacctc tggattacaa atttgtgaa agattgactg gtattcttaa ctatgttgct    60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact   240
ggttggggca ttgccaccac ctgtcagctc ctttccggga cttcgctttt ccccctcccct 300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttcctt ccgcggcctg ctgccggctc tgcggcctct tccgcctctt   540
cgccttcgcc ctcagacgag tcggatctcc ctttgggccg cctccccgc                589
```

<210> SEQ ID NO 9
<211> LENGTH: 251
<212> TYPE: DNA
<213> ORGANISM: Bos taurus

<400> SEQUENCE: 9

```
ttgccagcca tctgttgttt gcccctcccc cgtgccttcc ttgaccctgg aaggtgccac    60
tcccactgtc ctttcctaat aaaatgagga aattgcatcg cattgtctga gtaggtgtca  120
ttctattctg gggggtgggg tggggcagga cagcaagggg gaggattggg aatacaatag  180
caggcatgct ggggatgcgg tgggctctat gggtacccag gtgctgaaga attgacccgg  240
ttcctcctgg g                                                       251
```

<210> SEQ ID NO 10
<211> LENGTH: 127
<212> TYPE: DNA
<213> ORGANISM: Adeno-associated virus 2

<400> SEQUENCE: 10

```
gcgcgctcgc tcgctcactg aggccgcccg ggcaaagccc gggcgtcggg cgacctttgg    60
tcgcccggcc tcagtgagcg agcgagcgcg cagagaggga gtggccaact ccatcactag  120
gggttcc                                                            127
```

```
<210> SEQ ID NO 11
<211> LENGTH: 318
<212> TYPE: DNA
<213> ORGANISM: Human adenovirus 2

<400> SEQUENCE: 11
ctcactctct tccgcatcgc tgtctgcgag ggccagctgt tgggctcgcg gttgaggaca      60
aactcttcgc ggtctttcca gtactcttgg atcggaaacc cgtcggcctc cgaacggtac     120
tccgccaccg agggacctga gcgagtccgc atcgaccgga tcggaaaacc tctcgagaaa     180
ggcgtctaac cagtcacagt cgcaaggtag gctgagcacc gtggcgggcg gcagcgggtg     240
gcggtcgggg ttgtttctgg cggaggtgct gctgatgatg taattaaagt aggcggtctt     300
gagacggcgg atggtcga                                                   318

<210> SEQ ID NO 12
<211> LENGTH: 102
<212> TYPE: DNA
<213> ORGANISM: Human adenovirus 2

<400> SEQUENCE: 12
ccagctgttg gggtgagtac tccctctcaa aagcgggcat tacttctgcg ctaagattgt      60
cagtttccaa aaacgaggag gatttgatat tcacctggcc cg                        102

<210> SEQ ID NO 13
<211> LENGTH: 810
<212> TYPE: DNA
<213> ORGANISM: Homo sapiens

<400> SEQUENCE: 13
ctgttctcat cacatcatat caaggttata taccatcaat attgccacag atgttactta      60
gccttttaat atttctctaa tttagtgtat atgcaatgat agttctctga tttctgagat     120
tgagtttctc atgtgtaatg attatttaga gtttctcttt catctgttca aattttttgtc    180 tagttttatt ttttactgat tgtaagact tcttttttata atctgcatat tacaattctc     240
tttactgggg tgttgcaaat attttctgtc attctatggc ctgacttttc ttaatggttt     300
tttaatttta aaaataagtc ttaatattca tgcaatctaa ttaacaatct tttcttgtg      360 gttaggactt tgagtcataa gaatttttc tctacactga agtcatgatg gcatgcttct     420
atattatttt ctaaaagatt taaagttttg ccttctccat ttagacttat aattcactgg     480
aatttttttg tgtgtatggt atgacatatg ggttcccttt tattttttac atataaatat    540
atttccctgt ttttctaaaa aagaaaaaga tcatcatttt cccattgtaa aatgccatat    600
ttttttcata ggtcacttac atatatcaat gggtctgttt ctgagctcta ctctatttta    660
tcagcctcac tgtctatccc cacacatctc atgctttgct ctaaatcttg atatttagtg    720
gaacattctt tccatttttg ttctacaaga atattttgt tattgtcttt gggctttcta     780
tatacatttt gaaatgaggt tgacaagtta                                      810

<210> SEQ ID NO 14
<211> LENGTH: 202
<212> TYPE: DNA
<213> ORGANISM: Homo sapiens

<400> SEQUENCE: 14
ctgcccgggt ggcatccctg tgacccctcc ccagtgcctc tcctggccct ggaagttgcc      60
```

```
actccagtgc ccaccagcct tgtcctaata aaattaagtt gcatcatttt gtctgactag    120
gtgtccttct ataatattat ggggtggagg ggggtggtat ggagcaaggg gcccaagttg    180
ggaagaaacc tgtagggcct gc                                              202

<210> SEQ ID NO 15
<211> LENGTH: 145
<212> TYPE: DNA
<213> ORGANISM: Adeno-associated virus 2

<400> SEQUENCE: 15
gttaatcatt aactacaagg aaccccagt gatggagttg ccactccct ctctgcgcgc       60 tcgctcgctc actgaggccg ggcgaccaaa ggtcgcccga cgcccgggct ttgcccgggc    120
ggcctcagtg agcgagcgag cgcgc                                          145

<210> SEQ ID NO 16
<211> LENGTH: 155
<212> TYPE: DNA
<213> ORGANISM: Homo sapiens

<400> SEQUENCE: 16
ggcatgcttc tatattattt tctaaaagat ttaaagtttt gccttctcca tttagactta     60
taattcactg gaattttttt gtgtgtatgg tatgacatat gggttccctt ttattttta    120 catataaata tatttccctg ttttttctaaa aaaga                              155

<210> SEQ ID NO 17
<211> LENGTH: 726
<212> TYPE: DNA
<213> ORGANISM: Human hepatitis B virus

<400> SEQUENCE: 17
ataacaggcc tattgattgg aaagtttgtc aacgaattgt gggtcttttg gggtttgctg     60
ccccttttac gcaatgtgga tatcctgctt taatgccttt atatgcatgt atacaagcaa    120
acaggctttt actttctcg ccaacttaca aggcctttct cagtaaacag tatatgaccc     180
tttaccccgt tgctcggcaa cggcctggtc tgtgccaagt gtttgctgac gcaaccccca    240
ctggttgggg cttggccata ggccatcagc gcatgcgtgg aaccttttgtg tctcctctgc    300 cgatccatac tgcggaactc ctagccgctt gttttgctcg cagcaggtct ggagcaaacc    360
tcatcgggac cgacaattct gtcgtactct cccgcaagta tacatcgttt ccatggctgc    420
taggctgtgc tgccaactgg atcctgcgcg gacgtccctt tgtttacgtc ccgtcggcgc    480
tgaatcccgc ggacgacccc tcccggggcc gcttggggct ctaccgcccg cttctccgtc    540
tgccgtaccg tccgaccacg gggcgcacct ctctttacgc ggactccccg tctgtgcctt    600
ctcatctgcc ggaccgtgtg cacttcgctt cacctctgca cgtcgcatgg aggccaccgt    660
gaacgcccac cggaacctgc ccaaggtctt gcataagagg actcttggac tttcagcaat    720
gtcatc                                                               726

<210> SEQ ID NO 18
<211> LENGTH: 170
<212> TYPE: DNA
<213> ORGANISM: Human cytomegalovirus

<400> SEQUENCE: 18
gtaagtctgt tgacatgtat gtgatgtata ctaacctgca tgggacgtgg atttacttgt     60
gtatgtcaga tagagtaaag attaactctt gcatgtgagc ggggcatcga gatagcgata    120
```

```
aatgagtcag gaggacggat acttatatgt gttgttatcc tcctctacag      170
```

<210> SEQ ID NO 19
<211> LENGTH: 50
<212> TYPE: DNA
<213> ORGANISM: Homo sapiens

<400> SEQUENCE: 19

```
agcttgcttg ttctttttgc agaagctcag aataaacgct caactttggc       50
```

<210> SEQ ID NO 20
<211> LENGTH: 387
<212> TYPE: DNA
<213> ORGANISM: Oryctolagus cuniculus

<400> SEQUENCE: 20

```
tggctaataa aggaaattta ttttcattgc aatagtgtgt tggaattttt tgtgtctctc      60
actcggaagg acatatggga gggcaaatca tttaaaacat cagaatgagt atttggttta    120
gagtttggca acatatgccc atatgctggc tgccatgaac aaaggttggc tataaagagg    180
tcatcagtat atgaaacagc ccctgctgt ccattcctta ttccatagaa aagccttgac    240
ttgaggttag attttttta tattttgttt tgtgttattt ttttctttaa catccctaaa    300
attttcctta catgttttac tagccagatt tttcctcctc tcctgactac tcccagtcat    360
agctgtccct cttctcttat ggagatc                                        387
```

<210> SEQ ID NO 21
<211> LENGTH: 83
<212> TYPE: DNA
<213> ORGANISM: Human cytomegalovirus

<400> SEQUENCE: 21

```
ccgccccgtt gacgcaaatg gcggtaggc gtgtacggtg gaggtctat ataagcagag       60
ctcgtttagt gaaccgtcag atc                                            83
```

<210> SEQ ID NO 22
<211> LENGTH: 133
<212> TYPE: DNA
<213> ORGANISM: Artificial Sequence
<220> FEATURE:
<223> OTHER INFORMATION: Synthetic construct

<400> SEQUENCE: 22

```
gtaagtatca aggttacaag acaggtttaa ggagaccaat agaaactggg cttgtcgaga       60
cagagaagac tcttgcgttt ctgataggca cctattggtc ttactgacat ccactttgcc    120
tttctctcca cag                                                       133
```

<210> SEQ ID NO 23
<211> LENGTH: 197
<212> TYPE: DNA
<213> ORGANISM: Human cytomegalovirus

<400> SEQUENCE: 23

```
ggggctcggg tgcagcggcc agcgggcgcc tggcggcgag gattacccgg ggaagtggtt      60
gtctcctggc tggagccgcg agacgggcgc tcagggcgcg gggccggcgg cggcgaacga    120
gaggacggac tctggcggcc gggtctttgg ccgcggggag cgcgggcacc gggcgagcag    180
gccgcgtcgc gctcacc                                                   197
```

<210> SEQ ID NO 24
<211> LENGTH: 2064
<212> TYPE: DNA
<213> ORGANISM: Homo sapiens

<400> SEQUENCE: 24

| | | | | | | |
|---|---|---|---|---|---|---|
| atggtcagct | actgggacac | cggggtcctg | ctgtgcgcgc | tgctcagctg | tctgcttctc | 60 |
| acaggatcta | gttcaggttc | aaaattaaaa | gatcctgaac | tgagtttaaa | aggcacccag | 120 |
| cacatcatgc | aagcaggcca | gacactgcat | ctccaatgca | gggggaagc | agcccataaa | 180 |
| tggtctttgc | ctgaaatggt | gagtaaggaa | agcgaaaggc | tgagcataac | taaatctgcc | 240 |
| tgtggaagaa | atggcaaaca | attctgcagt | actttaacct | tgaacacagc | tcaagcaaac | 300 |
| cacactggct | tctacagctg | caaatatcta | gctgtaccta | cttcaaagaa | gaaggaaaca | 360 |
| gaatctgcaa | tctatatatt | tattagtgat | acaggtagac | ctttcgtaga | gatgtacagt | 420 |
| gaaatccccg | aaattataca | catgactgaa | ggaagggagc | tcgtcattcc | ctgccgggtt | 480 |
| acgtcaccta | acatcactgt | tactttaaaa | aagtttccac | ttgacacttt | gatccctgat | 540 |
| ggaaaacgca | taatctggga | cagtagaaag | ggcttcatca | tatcaaatgc | aacgtacaaa | 600 |
| gaaatagggc | ttctgacctg | tgaagcaaca | gtcaatgggc | atttgtataa | gacaaactat | 660 |
| ctcacacatc | gacaaaccaa | tacaatcata | gatgtccaaa | taagcacacc | acgcccagtc | 720 |
| aaattactta | gaggccatac | tcttgtcctc | aattgtactg | ctaccactcc | cttgaacacg | 780 |
| agagttcaaa | tgacctggag | ttaccctgat | gaaaaaaata | agagagcttc | cgtaaggcga | 840 |
| cgaattgacc | aaagcaattc | ccatgccaac | atattctaca | gtgttcttac | tattgacaaa | 900 |
| atgcagaaca | agacaaagg | actttatact | tgtcgtgtaa | ggagtggacc | atcattcaaa | 960 |
| tctgttaaca | cctcagtgca | tatatatgat | aaagcattca | tcactgtgaa | acatcgaaaa | 1020 |
| cagcaggtgc | ttgaaaccgt | agctggcaag | cggtcttacc | ggctctctat | gaaagtgaag | 1080 |
| gcatttcct | cgccggaagt | tgtatggtta | aagatgggt | tacctgcgac | tgagaaatct | 1140 |
| gctcgctatt | tgactcgtgg | ctactcgtta | attatcaagg | acgtaactga | agaggatgca | 1200 |
| gggaattata | caatcttgct | gagcataaaa | cagtcaaatg | tgtttaaaaa | cctcactgcc | 1260 |
| actctaattg | tcaatgtgaa | accccagatt | tacgaaaagg | ccgtgtcatc | gtttccagac | 1320 |
| ccggctctct | acccactggg | cagcagacaa | atcctgactt | gtaccgcata | tggtatccct | 1380 |
| caacctacaa | tcaagtggtt | ctggcacccc | tgtaaccata | atcattccga | agcaaggtgt | 1440 |
| gacttttgtt | ccaataatga | agagtccttt | atcctggatg | ctgacagcaa | catgggaaac | 1500 |
| agaattgaga | gcatcactca | gcgcatggca | ataatagaag | gaagaataa | gatggctagc | 1560 |
| accttggttg | tggctgactc | tagaatttct | ggaatctaca | tttgcatagc | ttccaataaa | 1620 |
| gttgggactg | tgggaagaaa | cataagcttt | tatatcacag | atgtgccaaa | tgggtttcat | 1680 |
| gttaacttgg | aaaaaatgcc | gacggaagga | gaggacctga | aactgtcttg | cacagttaac | 1740 |
| aagttcttat | acagagacgt | tacttggatt | ttactgcgga | cagttaataa | cagaacaatg | 1800 |
| cactacagta | ttagcaagca | aaaaatggcc | atcactaagg | agcactccat | cactcttaat | 1860 |
| cttaccatca | tgaatgtttc | cctgcaagat | tcaggcacct | atgcctgcag | agccaggaat | 1920 |
| gtatacacag | gggaagaaat | cctccagaag | aaagaaatta | caatcagagg | tgagcactgc | 1980 |
| aacaaaaagg | ctgtttttctc | tcggatctcc | aaatttaaaa | gcacaaggaa | tgattgtacc | 2040 |
| acacaaagta | atgtaaaaca | ttaa | | | | 2064 |

```
<210> SEQ ID NO 25
<211> LENGTH: 20
<212> TYPE: DNA
<213> ORGANISM: Human cytomegalovirus

<400> SEQUENCE: 25
aggactcatt aaaaagtaac                                                20

<210> SEQ ID NO 26
<211> LENGTH: 222
<212> TYPE: DNA
<213> ORGANISM: Simian virus 40

<400> SEQUENCE: 26
cagacatgat aagatacatt gatgagtttg acaaaccac aactagaatg cagtgaaaaa     60
aatgctttat ttgtgaaatt tgtgatgcta ttgctttatt tgtaaccatt ataagctgca   120
ataaacaagt taacaacaac aattgcattc attttatgtt tcaggttcag ggggagatgt   180
gggaggtttt ttaaagcaag taaaacctct acaaatgtgg ta                     222

<210> SEQ ID NO 27
<211> LENGTH: 1075
<212> TYPE: DNA
<213> ORGANISM: Artificial Sequence
<220> FEATURE:
<223> OTHER INFORMATION: Made in Lab - Polynucleotide cassette 1 full 5'

<400> SEQUENCE: 27
ctctggagac gcaacctttg gagctaagcc agcaatggta gagggaagat tctgcacgtc    60
ccttccaggc ggcctccccg tcaccacccc ccccaacccg ccccgaccgg agctgagagt   120
aattcataca aaaggactcg cccctgcctt ggggaatccc agggaccgtc gttaaactcc   180
cactaacgta gaacccagag atcgctgcgt tcccgccccc tcacccgccc gctctcgtca   240
tcactgaggt ggagaatagc atgcgtgagg ctccggtgcc cgtcagtggg cagagcgcac   300
atcgcccaca gtccccgaga agttgggggg aggggtcggc aattgaacgg gtgcctagag   360
aaggtggcgc ggggtaaact gggaaagtga tgtcgtgtac tggctccgcc ttttcccga    420 gggtggggga gaaccgtata taagtgcagt agtcgccgtg aacgttcttt ttcgcaacgg   480
gtttgccgcc agaacacagc gtctcagggg agatctcgtt tagtgaaccg tcagatcctc   540
actctcttcc gcatcgctgt ctgcgagggc cagctgttgg gctcgcggtt gaggacaaac   600
tcttcgcggt ctttccagta ctcttggatc ggaaacccgt cggcctccga acggtactcc   660
gccaccgagg gacctgagcg agtccgcatc gaccggatcg gaaaacctct cgagaaaggc   720
gtctaaccag tcacagtcgc aaggtaggct gagcaccgtg gcgggcggca gcgggtggcg   780
gtcggggttg tttctggcgg aggtgctgct gatgatgtaa ttaaagtagg cggtcttgag   840
acggcggatg gtcgaggtga ggtgtggcag gcttgagatc cagctgttgg ggtgagtact   900
ccctctcaaa agcgggcatt acttctgcgc taagattgtc agtttccaaa acgaggagg    960 atttgatatt cacctggccc gatctggcca tacacttgag tgacaatgac atccactttg  1020
cctttctctc cacaggtgtc cactcccagg tccaagttta aacgccgcca ccatg       1075

<210> SEQ ID NO 28
<211> LENGTH: 1768
<212> TYPE: DNA
<213> ORGANISM: Artificial Sequence
<220> FEATURE:
<223> OTHER INFORMATION: Made in Lab - Polynucleotide cassette 1 full 3'
```

<400> SEQUENCE: 28

```
ctgttctcat cacatcatat caaggttata taccatcaat attgccacag atgttactta        60
gccttttaat atttctctaa tttagtgtat atgcaatgat agttctctga tttctgagat       120
tgagtttctc atgtgtaatg attatttaga gtttctcttt catctgttca aattttttgtc     180
tagttttatt ttttactgat tgtaagact tcttttttata atctgcatat tacaattctc      240
tttactgggg tgttgcaaat attttctgtc attctatggc ctgacttttc ttaatggttt       300
tttaatttta aaataagtc ttaatattca tgcaatctaa ttaacaatct tttctttgtg        360
gttaggactt tgagtcataa gaatttttc tctacactga agtcatgatg gcatgcttct         420
atattatttt ctaaaagatt taaagttttg ccttctccat ttagacttat aattcactgg       480
aattttttg tgtgtatggt atgacatatg ggttccctttt tattttttac atataaatat       540
atttccctgt ttttctaaaa aagaaaaga tcatcatttt cccattgtaa aatgccatat         600
ttttttcata ggtcacttac atatatcaat gggtctgttt ctgagctcta ctctatttta      660
tcagcctcac tgtctatccc cacacatctc atgctttgct ctaaatcttg atatttagtg      720
gaacattctt tcccattttg ttctacaaga atattttttgt tattgtcttt gggctttcta     780
tatacatttt gaaatgaggt tgacaagtta cctaggaaaa ctgtcttcat aacaggccta      840
ttgattggaa agtttgtcaa cgaattgtgg gtcttttggg gtttgctgcc ccttttacgc      900
aatgtgata tcctgcttta atgcctttat atgcatgtat acaagcaaaa caggcttta        960
ctttctcgcc aacttacaag gcctttctca gtaaacagta tatgacccctt taccccgttg    1020
ctcggcaacg gcctggtctg tgccaagtgt ttgctgacgc aaccccccact ggttggggct     1080
tggccatagg ccatcagcgc atgcgtggaa cctttgtgtc tcctctgccg atccatactg    1140
cggaactcct agccgcttgt tttgctcgca gcaggtctgg agcaaacctc atcgggaccg      1200
acaattctgt cgtactctcc cgcaagtata catcgttttcc atggctgcta ggctgtgctg    1260
ccaactggat cctgcgcggg acgtcctttg tttacgtccc gtcggcgctg aatcccgcgg     1320
acgacccctc ccggggccgc ttggggctct accgcccgct tctccgtctg ccgtaccgtc      1380
cgaccacggg gcgcacctct ctttacgcgg actcccccgtc tgtgccttct catctgccgg    1440
accgtgtgca cttcgcttca cctctgcacg tcgcatggag gccaccgtga acgcccaccg      1500
gaacctgccc aaggtcttgc ataagaggac tcttggactt tcagcaatgt catcctgccc     1560
gggtggcatc cctgtgaccc ctccccagtg cctctcctgg ccctggaagt tgccactcca    1620
gtgcccacca gccttgtcct aataaaatta agttgcatca ttttgtctga ctaggtgtcc    1680
ttctataata ttatggggtg gagggggtg gtatggagca aggggcccaa gttgggaaga      1740
aacctgtagg gcctgcgaag acagtcag                                        1768
```

<210> SEQ ID NO 29
<211> LENGTH: 1193
<212> TYPE: DNA
<213> ORGANISM: Artificial Sequence
<220> FEATURE:
<223> OTHER INFORMATION: Made in Lab - Polynucleotide cassette 2 full 5'

<400> SEQUENCE: 29

```
ctctggagac ggcacatcgc ccacagtccc cgagaagttg ggaggggtcg gcaattgaac       60
cggtgcctag agaaggtggc gcggggtaaa ctgggaaagt gatgtcgtgt actggctccg      120
ccttttttccc gagggtgggg gagaaccgta taagtgca gtagtcgccg tgaacgttct        180
ttttcgcaac gggtttgccg ccagaacaca ggtaagtgcc gtgtgtggtt cccgcgggcc     240
```

```
tggcctcttt acgggttatg gcccttgcgt gccttgaatt acttccacct ggctccagta        300
cgtgattctt gatcccgagc tggagccagg ggcgggcctt gcgctttagg agcccccttcg       360 cctcgtgctt gagttgaggc ctggcctggg cgctggggcc gccgcgtgcg aatctggtgg        420
caccttcgcg cctgtctcgc tgctttcgat aagtctctag ccatttaaaa ttttttgatga      480 cgtgctgcga cgctttttttt ctggcaagat agtcttgtaa atgcgggcca ggatctgcac      540
actggtattt cggttttttgg gcccgcggcc ggcgacgggg cccgtgcgtc ccagcgcaca      600
tgttcggcga ggcggggcct gcgagcgcgg ccaccgagaa tcgacgggg gtagtctcaa        660 gctggccggc ctgctctggt gcctggcctc gcgccgccgt gtatcgcccc gccctgggcg      720
gcaaggctgg cccggtcggc accagttgcg tgagcggaaa gatggccgct tcccggccct      780
gctccagggg gctcaaaatg gaggacgcgg cgctcgggag agcgggcggg tgagtcaccc      840
acacaaagga aagggccctt tccgtcctca gccgtcgctt catgtgactc cacggagtac      900
cgggcgccgt ccaggcacct cgattagttc tggagctttt ggagtacgtc gtctttaggt      960
tggggggagg ggtttttatgc gatggagttt ccccacactg agtgggtgga gactgaagtt    1020
aggccagctt ggcacttgat gtaattctcc ttggaatttg gccttttttga gtttggatct    1080 tggttcattc tcaagcctca gacagtggtt caaagttttt ttcttccatt tcaggtgtcg    1140
tgaacacgtc tcagggggaga tctacaccca agctgtctag agccgccacc atg               1193

<210> SEQ ID NO 30
<211> LENGTH: 984
<212> TYPE: DNA
<213> ORGANISM: Artificial Sequence
<220> FEATURE:
<223> OTHER INFORMATION: Made in Lab - Polynucleotide cassette 2 full 3'

<400> SEQUENCE: 30
tgaggcatgc ttctatatta ttttctaaaa gatttaaagt tttgccttct ccatttagac         60
ttataattca ctggaatttt tttgtgtgta tggtatgaca tatgggttcc cttttatttt      120
ttacatataa atatatttcc ctgttttttct aaaaaagacc taggaaaact gtcttcataa     180
tcaacctctg gattacaaaa tttgtgaaag attgactggt attcttaact atgttgctcc      240
ttttacgcta tgtggatacg ctgctttaat gcctttgtat catgctattg cttcccgtat      300
ggctttcatt ttctcctcct tgtataaatc ctggttgctg tctctttatg aggagttgtg      360
gcccgttgtc aggcaacgtg gcgtggtgtg cactgtgttt gctgacgcaa ccccccactgg    420 ttgggggcatt gccaccacct gtcagctcct ttccgggact ttcgctttcc cctcccctat    480
tgccacggcg gaactcatcg ccgcctgcct tgcccgctgc tggacagggg ctcggctgtt    540
gggcactgac aattccgtgg tgttgtcggg gaaatcatcg tcctttcctt ggctgctcgc    600
ctgtgttgcc acctggattc tgcgcgggac gtccttctgc tacgtccctt cggccctcaa      660
tccagcggac cttccttccc gcggcctgct gccggcctg cggcctcttc cgcctcttcg     720
ccttcgccct cagacgagtc ggatctccct ttgggccgcc tccccgcatc ctgcccgggt    780
ggcatccctg tgacccctcc ccagtgcctc tcctggccct ggaagttgcc actccagtgc    840
ccaccagcct tgtcctaata aaattaagtt gcatcatttt gtctgactag gtgtccttct      900
ataatattat ggggtggagg ggggtggtat ggagcaaggg gcccaagttg gaagaaaacc    960
tgtagggcct gcgaagacag tcag                                             984

<210> SEQ ID NO 31
```

<211> LENGTH: 1481
<212> TYPE: DNA
<213> ORGANISM: Artificial Sequence
<220> FEATURE:
<223> OTHER INFORMATION: Made in Lab - Polynucleotide cassette 3 full 5'

<400> SEQUENCE: 31

| | | | | | |
|---|---|---|---|---|---|
| ctctggagac | gcaacctttg | gagctaagcc | agcaatggta | gagggaagat | tctgcacgtc | 60 |
| ccttccaggc | ggcctcccecg | tcaccaccec | cccaacccg | ccccgaccgg | agctgagagt | 120 |
| aattcataca | aaaggactcg | cccctgcctt | ggggaatccc | agggaccgtc | gttaaactcc | 180 |
| cactaacgta | gaacccagag | atcgctgcgt | tcccgccccc | tcacccgccc | gctctcgtca | 240 |
| tcactgaggt | ggagaatagc | atgcgtgagg | ctccggtgcc | cgtcagtggg | cagagcgcac | 300 |
| atcgcccaca | gtccccgaga | agttgggggg | agggtcggc | aattgaacgg | gtgcctagag | 360 |
| aaggtggcgc | ggggtaaact | gggaaagtga | tgtcgtgtac | tggctccgcc | tttttcccga | 420 |
| gggtggggga | gaaccgtata | taagtgcagt | agtcgccgtg | aacgttcttt | ttcgcaacgg | 480 |
| gtttgccgcc | agaacacagg | taagtgccgt | gtgtggttcc | cgcgggcctg | gcctctttac | 540 |
| gggttatggc | ccttgcgtgc | cttgaattac | ttccacctgg | ctccagtacg | tgattcttga | 600 |
| tcccgagctg | gagccagggg | cgggccttgc | gctttaggag | ccccttcgcc | tcgtgcttga | 660 |
| gttgaggcct | ggcctgggcg | ctggggccgc | cgcgtgcgaa | tctggtggca | ccttcgcgcc | 720 |
| tgtctcgctg | ctttcgataa | gtctctagcc | atttaaaatt | tttgatgacg | tgctgcgacg | 780 |
| cttttttttct | ggcaagatag | tcttgtaaat | gcgggccagg | atctgcacac | tggtatttcg | 840 |
| gttttttggc | ccgcggccgg | cgacggggcc | cgtgcgtccc | agcgcacatg | ttcggcgagg | 900 |
| cggggcctgc | gagcgcggcc | accgagaatc | ggacgggggt | agtctcaagc | tggccggcct | 960 |
| gctctggtgt | ctggcctcgc | gccgcgtgt | atcgcccgc | cctgggcggc | aaggctggcc | 1020 |
| cggtcggcac | cagttgcgtg | agcggaaaga | tggccgcttc | ccggccctgc | tccaggggc | 1080 |
| tcaaaatgga | ggacgcggcg | ctcggagag | cgggcgggtg | agtcacccac | acaaaggaaa | 1140 |
| agggcctttc | cgtcctcagc | cgtcgcttca | tgtgactcca | cggagtaccg | ggcgccgtcc | 1200 |
| aggcacctcg | attagttctg | gagcttttgg | agtacgtcgt | ctttaggttg | ggggagggg | 1260 |
| ttttatgcga | tggagtttcc | ccacactgag | tgggtggaga | ctgaagttag | gccagcttgg | 1320 |
| cacttgatgt | aattctccct | ggaatttggc | ctttttgagt | ttggatcttg | gttcattctc | 1380 |
| aagcctcaga | cagtggttca | agtttttttt | cttccatttc | aggtgtcgtg | aacacgtctc | 1440 |
| agggagatc | tacacccaag | ctgtctagag | ccgccaccat | g | | 1481 |

<210> SEQ ID NO 32
<211> LENGTH: 581
<212> TYPE: DNA
<213> ORGANISM: Artificial Sequence
<220> FEATURE:
<223> OTHER INFORMATION: Made in Lab - Polynucleotide cassette 3 full 3'

<400> SEQUENCE: 32

| | | | | | |
|---|---|---|---|---|---|
| ggttcccttt | tattttttac | atataaatat | atttccctgt | ttttctaaaa | agaaaaaga | 60 |
| tcatcatttt | cccattgtaa | aatgccatat | tttttcata | ggtcacttac | atatatcaat | 120 |
| gggtctgttt | ctgagctcta | ctctatttta | tcagcctcac | tgtctatccc | cacacatctc | 180 |
| atgctttgct | ctaaatcttg | atatttagtg | gaacattctt | tcccattttg | ttctacaaga | 240 |
| atatttttgt | tattgtctttt | gggctttcta | tatacatttt | gaaatgaggt | tgacaagtta | 300 |
| cctaggaaaa | ctgtcttctt | gccagccatc | tgttgtttgc | ccctcccccg | tgccttcctt | 360 |

```
gaccctggaa ggtgccactc ccactgtcct ttcctaataa aatgaggaaa ttgcatcgca    420
ttgtctgagt aggtgtcatt ctattctggg gggtggggtg gggcaggaca gcaaggggga    480
ggattgggaa tacaatagca ggcatgctgg ggatgcggtg ggctctatgg gtacccaggt    540
gctgaagaat tgacccggtt cctcctgggg aagacagtca g                       581
```

<210> SEQ ID NO 33
<211> LENGTH: 1511
<212> TYPE: DNA
<213> ORGANISM: Artificial Sequence
<220> FEATURE:
<223> OTHER INFORMATION: Made in Lab - Polynucleotide cassette 4 full 5'

<400> SEQUENCE: 33

```
ctctggagac gcaacctttg gagctaagcc agcaatggta gagggaagat tctgcacgtc     60
ccttccaggc ggcctccccg tcaccacccc ccccaacccg ccccgaccgg agctgagagt    120
aattcataca aaaggactcg cccctgcctt ggggaatccc agggaccgtc gttaaactcc    180
cactaacgta gaacccagag atcgctgcgt tcccgcccccc tcacccgccc gctctcgtca    240
tcactgaggt ggagaatagc atgcgtgagg ctccggtgcc cgtcagtggg cagagcgcac    300
atcgcccaca gtccccgaga agttgggggg aggggtcggc aattgaacgg gtgcctagag    360
aaggtggcgc ggggtaaact gggaaagtga tgtcgtgtac tggctccgcc ttttttcccga    420 gggtggggga gaaccgtata taagtgcagt agtcgccgtg aacgttcttt ttcgcaacgg    480
gtttgccgcc agaacacagg taagtgccgt gtgtggttcc cgcgggcctg gcctcttttac   540 gggttatggc ccttgcgtgc cttgaattac ttccacctgg ctccagtacg tgattcttga    600 tcccagctg gagccagggg cgggccttgc gctttaggag cccctttcgcc tcgtgcttga    660 gttgaggcct ggcctggggcg ctgggccgcc cgcgtgcgaa tctggtggca ccttcgcgcc    720
tgtctcgctg ctttcgataa gtctctagcc atttaaaatt tttgatgacg tgctgcgacg    780 cttttttttct ggcaagatag tcttgtaaat gcgggccagg atctgcacac tggtatttcg    840 gttttttgggc ccgcggccgg cgacgggggcc cgtgcgtccc agcgcacatg ttcggcgagg    900
cggggcctgc gagcgcggcc accgagaatc ggacgggggt agtctcaagc tggccggcct    960
gctctggtgc ctggcctcgc gccgccgtgt atcgccccgc cctgggcggc aaggctggcc   1020
cggtcggcac cagttgcgtg agcggaaaga tggccgcttc ccggccctgc tccaggggggc   1080 tcaaaatgga ggacgcggcg ctcgggagag cgggcgggtg agtcacccac acaaaggaaa   1140
agggcctttc cgtcctcagc cgtcgcttca tgtgactcca cggagtaccg ggcgccgtcc    1200
aggcacctcg attagttctg gagcttttgg agtacgtcgt ctttaggttg gggggagggg   1260
ttttatgcga tggagtttcc ccacactgag tgggtggaga ctgaagttag gccagccttgg   1320 cacttgatgt aattctcctt ggaatttggc ctttttgagt ttggatcttg gttcattctc    1380
aagcctcaga cagtggttca aagttttttt cttccatttc aggtgtcgtg aacacgtctc    1440
aggggagatc tagcttgctt gttcttttttg cagaagctca gaataaacgc tcaactttgg   1500
ccgccaccat g                                                       1511
```

<210> SEQ ID NO 34
<211> LENGTH: 717
<212> TYPE: DNA
<213> ORGANISM: Artificial Sequence
<220> FEATURE:
<223> OTHER INFORMATION: Made in Lab - Polynucleotide cassette 4 full 3'

<400> SEQUENCE: 34

```
ggttcccttt tatttttac atataaatat atttccctgt ttttctaaaa aagaaaaaga      60
tcatcatttt cccattgtaa aatgccatat tttttcata ggtcacttac atatatcaat    120
gggtctgttt ctgagctcta ctctatttta tcagcctcac tgtctatccc cacacatctc   180
atgctttgct ctaaatcttg atatttagtg aacattctt tcccattttg ttctacaaga    240
atatttttgt tattgtcttt gggcttctta tacattttt gaaatgaggt tgacaagtta    300
cctaggaaaa ctgtcttctg gctaataaag gaaatttatt ttcattgcaa tagtgtgttg   360
gaattttttg tgtctctcac tcggaaggac atatgggagg gcaaatcatt taaaacatca   420
gaatgagtat ttggtttaga gtttggcaac atatgcccat atgctggctg ccatgaacaa   480
aggttggcta taaagaggtc atcagtatat gaaacagccc cctgctgtcc attccttatt   540
ccatagaaaa gccttgactt gaggttagat tttttttata ttttgttttg tgttattttt   600
ttctttaaca tccctaaaat tttccttaca tgttttacta gccagatttt tcctcctctc   660
ctgactactc ccagtcatag ctgtccctct tctcttatgg agatcgaaga cagtcag     717
```

<210> SEQ ID NO 35
<211> LENGTH: 928
<212> TYPE: DNA
<213> ORGANISM: Artificial Sequence
<220> FEATURE:
<223> OTHER INFORMATION: Made in Lab - Polynucleotide cassette 5 full 5'

<400> SEQUENCE: 35

```
ctctggagac gacttacggt aaatggcccg cctggctgac cgcccaacga cccccgccca      60
ttgacgtcaa taatgacgta tgttcccata gtaacgccaa tagggacttt ccattgacgt    120
caatgggtgg agtatttacg gtaaactgcc cacttggcag tacatcaagt gtatcatatg    180
ccaagtccgc cccctattga cgtcaatgac ggtaaatggc ccgcctggca ttatgcccag    240
tacatgacct tacgggactt tcctacttgg cagtacatct acgtattagt catcgctatt    300
accaatgacg tcgaggagaa gttccccaac tttcccgcct ctcagccttt gaagaaaga    360
aaggggaggg gcaggccgc gtgcagccgc gagcggtgct gggctccggc tccaattccc    420
catctcagtc gttcccaaag tcctcctgtt tcatccaagc gtgtaagggt ccccgtcctt   480
gactccctag tgtcctgctg ccacagtcc agtcctggga accagcaccg atcacctccc    540
atcgggccaa tctcagtccc ttcccccta cgtcggggcc cacacgctcg gtgcgtgccc    600
agttgaacca gcgggctgcg gaaaaaaaaa agcggggaga aagtagggcc cggctactag   660
cggttttacg ggcgcacgta gctcaggcct caagaccttg gctgggact ggctgagcct    720
ggcgggaggc gggtccgag tcaccgcctg ccgccgcgcc cccggtttct ataaattgag   780
cccgcagcct cccgcttcgc tctctgctcc tcctgttcga cagtcagccg catcttcttt    840
tgcgtcgcca gcgtctcagg ggagatctag cttgcttgtt ctttttgcag aagctcagaa   900
taaacgctca actttggccg ccaccatg                                      928
```

<210> SEQ ID NO 36
<211> LENGTH: 1268
<212> TYPE: DNA
<213> ORGANISM: Artificial Sequence
<220> FEATURE:
<223> OTHER INFORMATION: Made in Lab - Polynucleotide cassette 5 full 3'

<400> SEQUENCE: 36

```
ggttcccttt tatttttac atataaatat atttccctgt ttttctaaaa aagaaaaaga      60
```

```
tcatcatttt cccattgtaa aatgccatat ttttttcata ggtcacttac atatatcaat        120
gggtctgttt ctgagctcta ctctatttta tcagcctcac tgtctatccc cacacatctc        180
atgctttgct ctaaatcttg atatttagtg aacattctt tcccattttg ttctacaaga         240 atattttgt tattgtcttt gggctttcta tatacatttt gaaatgaggt tgacaagtta         300
cctaggaaaa ctgtcttcat aacaggccta ttgattggaa agtttgtcaa cgaattgtgg        360
gtcttttggg gtttgctgcc ccttttacgc aatgtggata tcctgcttta atgcctttat        420
atgcatgtat acaagcaaaa caggcttttta ctttctcgcc aacttacaag gcctttctca       480
gtaaacagta tatgacccctt taccccgttg ctcggcaacg gcctggtctg tgccaagtgt       540
ttgctgacgc aaccccccact ggttggggct tggccatagg ccatcagcgc atgcgtggaa       600
cctttgtgtc tcctctgccg atccatactg cggaactcct agccgcttgt tttgctcgca       660
gcaggtctgg agcaaacctc atcgggaccg acaattctgt cgtactctcc cgcaagtata       720
catcgtttcc atggctgcta ggctgtgctg ccaactggat cctgcgcggg acgtcctttg       780
tttacgtccc gtcggcgctg aatcccgcgg acgacccctc ccggggccgc ttggggctct       840
accgcccgct tctccgtctg ccgtaccgtc cgaccacggg gcgcacctct ctttacgcgg       900
actccccgtc tgtgccttct catctgccgg accgtgtgca cttcgcttca cctctgcacg       960
tcgcatggag gccaccgtga acgcccaccg gaacctgccc aaggtcttgc ataagaggac       1020
tcttggactt tcagcaatgt catcctgccc gggtggcatc cctgtgaccc ctccccagtg      1080
cctctcctgg ccctggaagt tgccactcca gtgcccacca gccttgtcct aataaaatta      1140
agttgcatca ttttgtctga ctaggtgtcc ttctataata ttatggggtg gagggggtg        1200 gtatggagca agggggcccaa gttgggaaga aacctgtagg gcctgcgaag acagtcagac      1260
tgtcatta                                                                1268

<210> SEQ ID NO 37
<211> LENGTH: 1427
<212> TYPE: DNA
<213> ORGANISM: Artificial Sequence
<220> FEATURE:
<223> OTHER INFORMATION: Made in Lab - Polynucleotide cassette 6 full 5'

<400> SEQUENCE: 37
ctctggagac gacttacggt aaatggcccg cctggctgac cgcccaacga ccccccgccca        60 ttgacgtcaa taatgacgta tgttcccata gtaacgccaa tagggacttt ccattgacgt        120
caatgggtgg agtatttacg gtaaactgcc cacttggcag tacatcaagt gtatcatatg        180
ccaagtccgc cccctattga cgtcaatgac ggtaaatggc ccgcctggca ttatgcccag        240
tacatgacct tacgggactt tcctacttgg cagtacatct acgtattagt catcgctatt        300
accaatgacg tcgaggagaa gttccccaac tttcccgcct ctcagccttt gaaagaaaga       360
aaggggaggg gcaggccgc gtgcagccgc gagcggtgct gggctccggc tccaattccc        420
catctcagtc gttcccaaag tcctcctgtt tcatccaagc gtgtaagggt ccccgtcctt        480
gactccctag tgtcctgctg cccacagtcc agtcctggga accagcaccg atcacctccc       540
atcgggccaa tctcagtccc ttcccccta cgtcggggcc cacacgctcg gtgcgtgccc        600
agttgaacca ggcggctgcg gaaaaaaaa agcgggagaa agtagggcc cggctactag         660 cggttttacg ggcgcacgta gctcaggcct caagaccttg ggctgggact ggctgagcct       720
ggcgggaggc ggggtccgag tcaccgcctg ccgccgcgcc cccggtttct ataaattgag       780
```

```
cccgcagcct cccgcttcgc tctctgctcc tcctgttcga cagtcagccg catcttcttt    840
tgcgtcgcca gcgtctcagg ggagatctcg tttagtgaac cgtcagatcc tcactctctt    900
ccgcatcgct gtctgcgagg gccagctgtt gggctcgcgg ttgaggacaa actcttcgcg    960
gtctttccag tactcttgga tcggaaaccc gtcggcctcc gaacggtact ccgccaccga   1020
gggacctgag cgagtccgca tcgaccggat cggaaaacct ctcgagaaag gcgtctaacc   1080
agtcacagtc gcaaggtagg ctgagcaccg tggcgggcgg cagcgggtgg cggtcggggt   1140
tgtttctggc ggaggtgctg ctgatgatgt aattaaagta ggcggtcttg agacggcgga   1200
tggtcgaggt gaggtgtggc aggcttgaga tccagctgtt ggggtgagta ctccctctca   1260
aaagcgggca ttacttctgc gctaagattg tcagtttcca aaaacgagga ggatttgata   1320
ttcacctggc ccgatctggc catacacttg agtgacaatg acatccactt tgcctttctc   1380
tccacaggtg tccactccca ggtccaagtt taaacgccgc caccatg                 1427
```

<210> SEQ ID NO 38
<211> LENGTH: 1169
<212> TYPE: DNA
<213> ORGANISM: Artificial Sequence
<220> FEATURE:
<223> OTHER INFORMATION: Made in Lab - Polynucleotide cassette 6 full 3'

<400> SEQUENCE: 38

```
tgaggcatgc ttctatatta ttttctaaaa gatttaaagt tttgccttct ccatttagac     60
ttataattca ctggaatttt tttgtgtgta tggtatgaca tatgggttcc cttttatttt    120
ttacatataa atatatttcc ctgttttttct aaaaaagacc taggaaaact gtcttcataa    180
tcaacctctg gattacaaaa tttgtgaaag attgactggt attcttaact atgttgctcc    240
ttttacgcta tgtggatacg ctgctttaat gcctttgtat catgctattg cttcccgtat    300
ggctttcatt ttctcctcct tgtataaatc ctggttgctg tctctttatg aggagttgtg    360
gcccgttgtc aggcaacgtg gcgtggtgtg cactgtgttt gctgacgcaa ccccactgg    420 ttggggcatt gccaccacct gtcagctcct ttccgggact ttcgctttcc cctccctat    480 tgccacggcg gaactcatcg ccgcctgcct tgcccgctgc tggacagggg ctcggctgtt    540
gggcactgac aattccgtgg tgttgtcggg gaaatcatcg tcctttcctt ggctgctcgc    600
ctgtgttgcc acctggattc tgcgcgggac gtccttctgc tacgtccctt cggccctcaa    660
tccagcggac cttccttccc gcggcctgct gccggctctg cggcctcttc cgcctcttcg    720
ccttcgccct cagacgagtc ggatctccct ttgggccgcc tccccgcatc tggctaataa    780
aggaaattta ttttcattgc aatagtgtgt tggaattttt tgtgtctctc actcggaagg    840
acatatggga gggcaaatca tttaaaacat cagaatgagt atttggttta gagtttggca    900
acatatgccc atatgctggc tgccatgaac aaaggttggc tataaagagg tcatcagtat    960
atgaaacagc cccctgctgt ccattcctta ttccatagaa aagccttgac ttgaggttag   1020 attttttttta tattttgttt tgtgttattt ttttctttaa catccctaaa attttcctta   1080
catgttttac tagccagatt tttcctcctc tcctgactac tcccagtcat agctgtccct   1140
cttctcttat ggagatcgaa gacagtcag                                      1169
```

<210> SEQ ID NO 39
<211> LENGTH: 1755
<212> TYPE: DNA
<213> ORGANISM: Artificial Sequence
<220> FEATURE:
<223> OTHER INFORMATION: Made in Lab - Polynucleotide cassette 7 full 5'

<400> SEQUENCE: 39

```
ctctggagac gcgttacata acttacggta aatggcccgc ctggctgacc gcccaacgac        60
ccccgcccat tgacgtcaat aatgacgtat gttcccatag taacgccaat agggactttc       120
cattgacgtc aatgggtgga gtatttacgg taaactgccc acttggcagt acatcaagtg       180
tatcatatgc caagtacgcc ccctattgac gtcaatgacg gtaaatggcc cgcctggcat       240
tatgcccagt acatgacctt atgggacttt cctacttggc agtacatcta cgtattagtc       300
atcgctatta ccatggtcga ggtgagcccc acgttctgct tcactctccc catctccccc       360
ccctccccac cccaattttt gtatttattt attttttaat tattttgtgc agcgatgggg       420
gcggggggg ggggggcgcg cgccaggcgg ggcggggcgg ggcgaggggc ggggcgggc         480
gaggcggaga ggtgcggcgg cagccaatca gagcggcgcg ctccgaaagt tcccttttat       540
ggcgaggcgg cggcggcggc ggccctataa aaagcgaagc gcgcggcggg cgggagtcgc       600
tgcgcgctgc cttcgccccg tgccccgctc cgccgccgcc tcgcgccgcc cgccccggct       660
ctgactgacc gcgttactcc cacaggtgag cgggcgggac ggcccttctc ctccgggctg       720
taattagcgc ttggtttaat gacgcttgt ttcttttctg tggctgcgtg aaagccttga       780
ggggctccgg gagggccctt tgtgcggggg ggagcggctc ggggggtgcg tgcgtgtgtg       840
tgtgcgtggg gagcgccgcg tgcggctccg cgctgcccgg cggctgtgag cgctgcgggc       900
gcggcgcggg gctttgtgcg ctccgcagtg tgcgcgaggg gagcgcggcc ggggcggtg       960
ccccgcggtg cgggggggc tgcgagggga acaaaggctg cgtgcgggt gtgtgcgtgg      1020
gggggtgagc aggggtgtg ggcgcgtcgg tcggctgca accccccctg caccccccctc      1080
cccgagttgc tgagcacggc ccggcttcgg gtgcggggct ccgtacgggg cgtggcgcgg      1140
ggctcgccgt gccgggcggg gggtggcggc aggtggggt gccgggcggg gcggggccgc      1200
ctcgggccgg ggagggctcg ggggagggc gcggcggccc ccggagcgcc ggcggctgtc      1260
gaggcgcggc gagccgcagc cattgccttt tatggtaatc gtgcgagagg gcgcagggac      1320
ttcctttgtc ccaaatctgt gcggagccga atctgggag gcgccgccgc acccctcta        1380
gcgggcgcgg ggcgaagcgg tgcggcgccg gcaggaagga aatgggcggg gagggccttc      1440
gtgcgtcgcc gcgccgccgt ccccttctcc ctctccagcc tcggggctgt ccgcgggggg      1500
acggctgcct tcgggggga cggggcaggg cggggttcgg cttctggcgt gtgaccggcg      1560
gctctagagc ctctgctaac catgttcatg ccttcttctt tttcctacag ctcctgggca      1620
acgtgctggt tattgtgctg tctcatcatt tggcaaaga attcggcttg atcgaagccg       1680
tctcagggga gatctagctt gcttgttctt tttgcagaag ctcagaataa acgctcaact      1740
ttggccgcca ccatg                                                        1755
```

<210> SEQ ID NO 40
<211> LENGTH: 1165
<212> TYPE: DNA
<213> ORGANISM: Artificial Sequence
<220> FEATURE:
<223> OTHER INFORMATION: Made in Lab - Polynucleotide cassette 7 full 3'

<400> SEQUENCE: 40

```
tgaggcatgc ttctatatta ttttctaaaa gatttaaagt tttgccttct ccatttagac        60
ttataattca ctggaatttt tttgtgtgta tggtatgaca tatgggttcc cttttatttt       120
ttacatataa atatatttcc ctgttttct aaaaagacc taggaaaact gtcttcataa        180
```

| | |
|---|---|
| caggcctatt gattggaaag tttgtcaacg aattgtgggt cttttggggt ttgctgcccc | 240 |
| ttttacgcaa tgtggatatc ctgctttaat gcctttatat gcatgtatac aagcaaaaca | 300 |
| ggcttttact ttctcgccaa cttacaaggc ctttctcagt aaacagtata tgacccttta | 360 |
| ccccgttgct cggcaacggc ctggtctgtg ccaagtgttt gctgacgcaa ccccactgg | 420 |
| ttggggcttg gccataggcc atcagcgcat gcgtggaacc tttgtgtctc ctctgccgat | 480 |
| ccatactgcg gaactcctag ccgcttgttt tgctcgcagc aggtctggag caaacctcat | 540 |
| cgggaccgac aattctgtcg tactctcccg caagtataca tcgtttccat ggctgctagg | 600 |
| ctgtgctgcc aactggatcc tgcgcgggac gtccttttgt tacgtcccgt cggcgctgaa | 660 |
| tcccgcggac gacccctccc ggggccgctt ggggctctac cgcccgcttc tccgtctgcc | 720 |
| gtaccgtccg accacggggc gcacctctct ttacgcggac tccccgtctg tgccttctca | 780 |
| tctgccggac cgtgtgcact tcgcttcacc tctgcacgtc gcatggaggc caccgtgaac | 840 |
| gcccaccgga acctgcccaa ggtcttgcat aagaggactc ttggactttc agcaatgtca | 900 |
| tcttgccagc catctgttgt tgccccctcc ccgtgccttc cttgaccct ggaaggtgcc | 960 |
| actcccactg tcctttccta ataaaatgag gaaattgcat cgcattgtct gagtaggtgt | 1020 |
| cattctattc tggggggtgg ggtggggcag gacagcaagg gggaggattg gaatacaat | 1080 |
| agcaggcatg ctggggatgc ggtgggctct atgggtaccc aggtgctgaa gaattgaccc | 1140 |
| ggttcctcct ggggaagaca gtcag | 1165 |

<210> SEQ ID NO 41
<211> LENGTH: 1159
<212> TYPE: DNA
<213> ORGANISM: Artificial Sequence
<220> FEATURE:
<223> OTHER INFORMATION: Made in Lab - Polynucleotide cassette 8 full 5'

<400> SEQUENCE: 41

| | |
|---|---|
| ctctggagac gacttacggt aaatggcccg cctggctgac cgcccaacga ccccgccca | 60 |
| ttgacgtcaa taatgacgta tgttcccata gtaacgccaa tagggacttt ccattgacgt | 120 |
| caatgggtgg agtatttacg gtaaactgcc cacttggcag tacatcaagt gtatcatatg | 180 |
| ccaagtccgc cccctattga cgtcaatgac ggtaaatggc ccgcctggca ttatgcccag | 240 |
| tacatgacct tacgggactt tcctacttgg cagtacatct acgtattagt catcgctatt | 300 |
| accatggtcg aggtgagccc cacgttctgc ttcactctcc catctcccc ccctcccca | 360 |
| cccccaattt tgtatttatt tatttttaa ttatttgtg cagcgatggg ggcggggggg | 420 |
| gggggcgcg cgccaggcgg ggcggggcgg ggcgagggc gggcggggc gaggcggaga | 480 |
| ggtgcggcgg cagccaatca gagcggcgcg ctccgaaagt ttccttttat ggcgaggcgg | 540 |
| cggcggcggc ggccctataa aaagcgaagc gcgcggcggg cggcgtctca ggggagatct | 600 |
| cgtttagtga accgtcagat cctcactctc ttccgcatcg ctgtctgcga gggccagctg | 660 |
| ttgggctcgc ggttgaggac aaactcttcg cggtctttcc agtactcttg gatcggaaac | 720 |
| ccgtcggcct ccgaacggta ctccgccacc gagggacctg agcgagtccg catcgaccgg | 780 |
| atcggaaaac ctctcgagaa aggcgtctaa ccagtcacag tcgcaaggta ggctgagcac | 840 |
| cgtggcgggc ggcagcgggt ggcggtcggg gttgtttctg gcggaggtgc tgctgatgat | 900 |
| gtaattaaag taggcggtct tgagacggcg gatggtcgag gtgaggtgtg gcaggcttga | 960 |
| gatccagctg ttggggtgag tactcccttct caaaagcggg cattacttct gcgctaagat | 1020 |
| tgtcagtttc caaaaacgag gaggatttga tattcacctg gcccgatctg gccatacact | 1080 |

```
tgagtgacaa tgacatccac tttgcctttc tctccacagg tgtccactcc caggtccaag    1140
tttaaacgcc gccaccatg                                                 1159

<210> SEQ ID NO 42
<211> LENGTH: 572
<212> TYPE: DNA
<213> ORGANISM: Artificial Sequence
<220> FEATURE:
<223> OTHER INFORMATION: Made in Lab - Polynucleotide cassette 8 full 3'

<400> SEQUENCE: 42
ggcatgcttc tatattattt tctaaaagat ttaaagttttt gccttctcca tttagactta      60
taattcactg gaattttttt gtgtgtatgg tatgacatat gggttccctt ttatttttta     120
catataaata tatttccctg tttttctaaa aagacctag gaaaactgtc ttctggctaa      180
taaaggaaat ttattttcat tgcaatagtg tgttggaatt ttttgtgtct ctcactcgga     240
aggacatatg ggagggcaaa tcatttaaaa catcagaatg agtatttggt ttagagtttg     300
gcaacatatg cccatatgct ggctgccatg aacaaaggtt ggctataaag aggtcatcag     360
tatatgaaac agcccctgc tgtccattcc ttattccata gaaagccctt gacttgaggt      420
tagatttttt ttatatttg ttttgtgtta ttttttttctt taacatccct aaaattttcc     480
ttacatgttt tactagccag attttttcctc ctctcctgac tactcccagt catagctgtc    540
cctcttctct tatggagatc gaagacagtc ag                                   572

<210> SEQ ID NO 43
<211> LENGTH: 1519
<212> TYPE: DNA
<213> ORGANISM: Artificial Sequence
<220> FEATURE:
<223> OTHER INFORMATION: Made in Lab - Polynucleotide cassette 9 full 5'

<400> SEQUENCE: 43
ctctggagac gacttacggt aaatggcccg cctggctgac cgcccaacga ccccgccca       60 ttgacgtcaa taatgacgta tgttcccata gtaacgccaa tagggacttt ccattgacgt     120
caatgggtgg agtatttacg gtaaactgcc cacttggcag tacatcaagt gtatcatatg     180
ccaagtccgc ccctattga cgtcaatgac ggtaaatggc ccgcctggca ttatgcccag      240
tacatgacct tacgggactt tcctacttgg cagtacatct acgtattagt catcgctatt     300
accagcacat cgcccacagt ccccgagaag ttggggggag gggtcggcaa ttgaaccggt     360
gcctagagaa ggtggcgcgg ggtaaactgg gaaagtgatg tcgtgtactg gctccgcctt     420
tttcccgagg gtgggggaga accgtatata agtgcagtag tcgccgtgaa cgttctttt     480 cgcaacgggt ttgccgccag aacacaggta agtgccgtgt gtggttcccg cgggcctggc    540
ctctttacgg gttatggccc ttgcgtgcct tgaattactt ccacctggct ccagtacgtg    600
attcttgatc ccgagctgga gccaggggcg ggccttgcgc tttaggagcc ccttcgcctc    660
gtgcttgagt tgaggcctgg cctgggcgct ggggccgccg cgtgcgaatc tggtggcacc    720
ttcgcgcctg tctcgctgct ttcgataagt ctctagccat ttaaaatttt tgatgacgtg    780
ctgcgacgct ttttttctgg caagatagtc ttgtaaatgc gggccaggat ctgcacactg    840
gtatttcggt ttttgggccc gcggccggcg acggggcccg tgcgtcccag cgcacatgtt    900
cggcgaggcg gggcctgcga gcgcggccac cgagaatcgg acggggtag tctcaagctg    960 gccggcctgc tctggtgcct ggcctcgcgc cgccgtgtat cgccccgccc tgggcggcaa   1020
```

```
ggctggcccg gtcggcacca gttgcgtgag cggaaagatg gccgcttccc ggccctgctc    1080 caggggctc aaaatggagg acgcggcgct cgggagagcg ggcgggtgag tcacccacac     1140
aaaggaaaag ggcctttccg tcctcagccg tcgcttcatg tgactccacg gagtaccggg    1200
cgccgtccag gcacctcgat tagttctgga gcttttggag tacgtcgtct ttaggttggg    1260
gggaggggtt ttatgcgatg gagtttcccc acactgagtg ggtggagact gaagttaggc    1320
cagcttggca cttgatgtaa ttctccttgg aatttggcct ttttgagttt ggatcttggt    1380
tcattctcaa gcctcagaca gtggttcaaa gttttttttct tccatttcag gtgtcctgaa   1440
cacgtctcag gggagatcta gcttgcttgt tcttttttgca gaagctcaga ataaacgctc   1500
aactttggcc gccaccatg                                                 1519
```

<210> SEQ ID NO 44
<211> LENGTH: 387
<212> TYPE: DNA
<213> ORGANISM: Artificial Sequence
<220> FEATURE:
<223> OTHER INFORMATION: Made in Lab - Polynucleotide cassette 9 full 3'

<400> SEQUENCE: 44

```
ggcatgcttc tatattattt tctaaaagat ttaaagtttt gccttctcca tttagactta     60
taattcactg gaattttttt gtgtgtatgg tatgacatat gggttccctt ttatttttta    120
catataaata tatttccctg ttttttctaaa aagacctag gaaaactgtc ttcctgcccg    180
ggtggcatcc ctgtgacccc tccccagtgc ctctcctggc cctggaagtt gccactccag    240
tgcccaccag ccttgtccta ataaaattaa gttgcatcat tttgtctgac taggtgtcct    300
tctataatat tatggggtgg aggggggtgg tatggagcaa ggggcccaag ttgggaagaa    360
acctgtaggg cctgcgaaga cagtcag                                        387
```

<210> SEQ ID NO 45
<211> LENGTH: 1489
<212> TYPE: DNA
<213> ORGANISM: Artificial Sequence
<220> FEATURE:
<223> OTHER INFORMATION: Made in Lab - Polynucleotide cassette 10 full
       5'

<400> SEQUENCE: 45

```
ctctggagac gacttacggt aaatggcccg cctggctgac cgcccaacga ccccgccca     60 ttgacgtcaa taatgacgta tgttcccata gtaacgccaa tagggacttt ccattgacgt    120
caatgggtgg agtatttacg gtaaactgcc cacttggcag tacatcaagt gtatcatatg    180
ccaagtccgc ccctattga cgtcaatgac ggtaaatggc ccgcctggca ttatgcccag    240
tacatgacct tacgggactt tcctacttgg cagtacatct acgtattagt catcgctatt    300
accagcacat cgcccacagt ccccgagaag ttgggggag gggtcggcaa ttgaaccggt     360
gcctagagaa ggtggcgcgg ggtaaactgg gaaagtgatg tcgtgtactg gctccgcctt    420
tttcccgagg gtgggggaga accgtatata agtgcagtag tcgccgtgaa cgttctttt    480 cgcaacgggt ttgccgccag aacacaggta agtgccgtgt gtggttcccg cgggcctggc    540
ctctttacgg gttatggccc ttgcgtgcct tgaattactt ccacctggct ccagtacgtg    600
attcttgatc ccgagctgga gccaggggcg ggccttgcgc tttaggagcc cttcgcctc    660 gtgcttgagt tgaggcctgg cctgggcgct ggggccgccg cgtgcgaatc tggtggcacc    720
ttcgcgcctg tctcgctgct ttcgataagt ctctagccat ttaaaatttt tgatgacgtg    780
```

| | |
|---|---|
| ctgcgacgct tttttttctgg caagatagtc ttgtaaatgc gggccaggat ctgcacactg | 840 |
| gtatttcggt ttttgggccc gcggccggcg acggggcccg tgcgtcccag cgcacatgtt | 900 |
| cggcgaggcg gggcctgcga gcgcggccac cgagaatcgg acggggggtag tctcaagctg | 960 |
| gccggcctgc tctggtgcct ggcctcgcgc cgccgtgtat cgccccgccc tgggcggcaa | 1020 |
| ggctggcccg tcggcacca gttgcgtgag cggaaagatg gccgcttccc ggccctgctc | 1080 |
| caggggggctc aaaatggagg acgcggcgct cgggagagcg ggcgggtgag tcacccacac | 1140 |
| aaaggaaaag ggccttttccg tcctcagccg tcgcttcatg tgactccacg gagtaccggg | 1200 |
| cgccgtccag gcacctcgat tagttctgga gcttttggag tacgtcgtct ttaggttggg | 1260 |
| gggaggggtt ttatgcgatg gagtttcccc acactgagtg ggtggagact gaagttaggc | 1320 |
| cagcttggca cttgatgtaa ttctccttgg aatttggcct ttttgagttt ggatcttggt | 1380 |
| tcattctcaa gcctcagaca gtggttcaaa gttttttttct tccatttcag gtgtcctgaa | 1440 |
| cacgtctcag gggagatcta cacccaagct gtctagagcc gccaccatg | 1489 |

<210> SEQ ID NO 46
<211> LENGTH: 1180
<212> TYPE: DNA
<213> ORGANISM: Artificial Sequence
<220> FEATURE:
<223> OTHER INFORMATION: Made in Lab - Polynucleotide cassette 10 full 3'

<400> SEQUENCE: 46

| | |
|---|---|
| ggttcccttt tattttttac atataaatat atttccctgt ttttctaaaa aagaaaaaga | 60 |
| tcatcatttt cccattgtaa aatgccatat ttttttcata ggtcacttac atatatcaat | 120 |
| gggtctgttt ctgagctcta ctctatttta tcagcctcac tgtctatccc cacacatctc | 180 |
| atgctttgct ctaaatcttg atatttagtg gaacattctt tcccattttg ttctacaaga | 240 |
| atattttttgt tattgtcttt gggctttcta tatacatttt gaaatgaggt tgacaagtta | 300 |
| cctaggaaaa ctgtcttcat ataatcaacc tctggattac aaaatttgtg aaagattgac | 360 |
| tggtattctt aactatgttg ctccttttac gctatgtgga tacgctgctt taatgccttt | 420 |
| gtatcatgct attgcttccc gtatggcttt catttttctcc tccttgtata aatcctggtt | 480 |
| gctgtctctt tatgaggagt tgtggcccgt tgtcaggcaa cgtggcgtgg tgtgcactgt | 540 |
| gtttgctgac gcaaccccca ctggttgggg cattgccacc acctgtcagc tcctttccgg | 600 |
| gactttcgct ttccccctcc ctattgccac ggcggaactc atcgccgcct gccttgcccg | 660 |
| ctgctggaca ggggctcggc tgttgggcac tgacaattcc gtggtgttgt cggggaaatc | 720 |
| atcgtccttt ccttggctgc tcgcctgtgt tgccacctgg attctgcgcg gacgtccttt | 780 |
| ctgctacgtc ccttcggccc tcaatccagc ggaccttcct tcccgcggcc tgctgccggc | 840 |
| tctgcggcct cttccgcctc ttcgccttcg ccctcagacg agtcggatct ccctttgggc | 900 |
| cgcctccccg catcatcttg ccagccatct gttgtttgcc cctcccccgt gccttccttg | 960 |
| accctggaag gtgccactcc cactgtcctt tcctaataaa atgaggaaat tgcatcgcat | 1020 |
| tgtctgagta ggtgtcattc tattctgggg ggtggggtgg ggcaggacag caaggggggag | 1080 |
| gattgggaat acaatagcag gcatgctggg gatgcggtgg gctctatggg tacccaggtg | 1140 |
| ctgaagaatt gacccggttc ctcctgggga agacagtcag | 1180 |

<210> SEQ ID NO 47
<211> LENGTH: 1172
<212> TYPE: DNA

<213> ORGANISM: Artificial Sequence
<220> FEATURE:
<223> OTHER INFORMATION: Made in Lab - Polynucleotide cassette 11 full 5'

<400> SEQUENCE: 47

| | |
|---|---:|
| ctctggagac gacttacggt aaatggcccg cctggctgac cgcccaacga ccccccgccca | 60 |
| ttgacgtcaa taatgacgta tgttcccata gtaacgccaa tagggacttt ccattgacgt | 120 |
| caatgggtgg agtatttacg gtaaactgcc cacttggcag tacatcaagt gtatcatatg | 180 |
| ccaagtccgc ccctattga cgtcaatgac ggtaaatggc ccgcctggca ttatgcccag | 240 |
| tacatgacct tacgggactt tcctacttgg cagtacatct acgtattagt catcgctatt | 300 |
| accatgctga tgcggttttg gcagtacacc aatgggcgtg gatagcggtt tgactcacgg | 360 |
| ggatttccaa gtctccaccc cattgacgtc aatgggagtt gtttttggca ccaaaatcaa | 420 |
| cgggactttc caaaatgtcg taataacccc gccccgttga cgcaaatggg cggtaggcgt | 480 |
| gtacggtggg aggtctatat aagcagagct cgtttagtga accgtcagat cgcctggaga | 540 |
| ggccatccac gctgttttga cctccatagt ggacaccggg accgatccag cctccgcgtc | 600 |
| tcaggggaga tctcgtttag tgaaccgtca gatcctcact ctcttccgca tcgctgtctg | 660 |
| cgagggccag ctgttgggct cgcggttgag gacaaactct cgcggtcttt ccagtactc | 720 |
| ttggatcgga aacccgtcgg cctccgaacg gtactccgcc accgagggac ctgagcgagt | 780 |
| ccgcatcgac cggatcggaa aacctctcga gaaaggcgtc taaccagtca cagtcgcaag | 840 |
| gtaggctgag caccgtggcg ggcggcagcg ggtggcggtc ggggttgttt ctggcggagg | 900 |
| tgctgctgat gatgtaatta agtaggcgg tcttgagacg gcggatggtc gaggtgaggt | 960 |
| gtggcaggct tgagatccag ctgttggggt gagtactccc tctcaaaagc gggcattact | 1020 |
| tctgcgctaa gattgtcagt ttccaaaaac gaggaggatt tgatattcac ctggcccgat | 1080 |
| ctggccatac acttgagtga caatgacatc cactttgcct ttctctccac aggtgtccac | 1140 |
| tcccaggtcc aagtttaaac gccgccacca tg | 1172 |

<210> SEQ ID NO 48
<211> LENGTH: 1043
<212> TYPE: DNA
<213> ORGANISM: Artificial Sequence
<220> FEATURE:
<223> OTHER INFORMATION: Made in Lab - Polynucleotide cassette 11 full 3'

<400> SEQUENCE: 48

| | |
|---|---:|
| actgttctca tcacatcata tcaaggttat ataccatcaa tattgccaca gatgttactt | 60 |
| agccttttaa tatttctcta atttagtgta tatgcaatga tagttctctg atttctgaga | 120 |
| ttgagtttct catgtgtaat gattatttag agtttctctt tcatctgttc aaattttttgt | 180 |
| ctagttttat tttttactga tttgtaagac ttctttttat aatctgcata ttacaattct | 240 |
| ctttactggg gtgttgcaaa tattttctgt cattctatgg cctgactttt cttaatggtt | 300 |
| ttttaatttt aaaaataagt cttaatattc atgcaatcta attaacaatc ttttctttgt | 360 |
| ggttaggact tgagtcata agaaattttt ctctacactg aagtcatgat ggcatgcttc | 420 |
| tatattattt tctaaaagat ttaaagtttt gccttctcca tttagactta taattcactg | 480 |
| gaatttttt gtgtgtatgg tatgacatat gggttcccct ttattttta catataaata | 540 |
| tatttccctg tttttctaaa aagaaaaag atcatcattt tcccattgta aaatgccata | 600 |
| ttttttttcat aggtcactta catatatcaa tgggtctgtt tctgagctct actctatttt | 660 |

| | |
|---|---|
| atcagcctca ctgtctatcc ccacacatct catgctttgc tctaaatctt gatatttagt | 720 |
| ggaacattct ttcccatttt gttctacaag aatattttg ttattgtctt tgggctttct | 780 |
| atatacattt tgaaatgagg ttgacaagtt acctaggaaa actgtcttcc tgcccgggtg | 840 |
| gcatccctgt gacccctccc cagtgcctct cctggccctg gaagttgcca ctccagtgcc | 900 |
| caccagcctt gtcctaataa aattaagttg catcattttg tctgactagg tgtccttcta | 960 |
| taatattatg gggtggaggg gggtggtatg gagcaagggg cccaagttgg gaagaaacct | 1020 |
| gtagggcctg cgaagacagt cag | 1043 |

<210> SEQ ID NO 49
<211> LENGTH: 1172
<212> TYPE: DNA
<213> ORGANISM: Artificial Sequence
<220> FEATURE:
<223> OTHER INFORMATION: Made in Lab - Polynucleotide cassette 12 full 5'

<400> SEQUENCE: 49

| | |
|---|---|
| ctctggagac gacttacggt aaatggcccg cctggctgac cgcccaacga ccccgccca | 60 |
| ttgacgtcaa taatgacgta tgttcccata gtaacgccaa tagggacttt ccattgacgt | 120 |
| caatgggtgg agtatttacg gtaaactgcc cacttggcag tacatcaagt gtatcatatg | 180 |
| ccaagtccgc ccctattga cgtcaatgac ggtaaatggc ccgcctggca ttatgcccag | 240 |
| tacatgacct tacgggactt tcctacttgg cagtacatct acgtattagt catcgctatt | 300 |
| accatgctga tgcggttttg gcagtacacc aatgggcgtg gatagcggtt tgactcacgg | 360 |
| ggatttccaa gtctccaccc cattgacgtc aatgggagtt tgttttggca ccaaaatcaa | 420 |
| cgggactttc caaaatgtcg taataacccc gccccgttga cgcaaatggg cggtaggcgt | 480 |
| gtacggtggg aggtctatat aagcagagct cgtttagtga accgtcagat cgcctggaga | 540 |
| ggccatccac gctgttttga cctccatagt ggacaccggg accgatccag cctccgcgtc | 600 |
| tcagggagat ctcgtttag tgaaccgtca gatcctcact ctcttccgca tcgctgtctg | 660 |
| cgagggccag ctgttgggct cgcggttgag gacaaactct tcgcggtctt tccagtactc | 720 |
| ttggatcgga aacccgtcgg cctccgaacg gtactccgcc accgagggac ctgagcgagt | 780 |
| ccgcatcgac cggatcggaa aacctctcga gaaaggcgtc taaccagtca cagtcgcaag | 840 |
| gtaggctgag caccgtggcg ggcggcagcg ggtggcggtc ggggttgttt ctggcggagg | 900 |
| tgctgctgat gatgtaatta agtaggcgg tcttgagacg gcggatggtc gaggtgaggt | 960 |
| gtggcaggct tgagatccag ctgttggggt gagtactccc tctcaaaagc gggcattact | 1020 |
| tctgcgctaa gattgtcagt ttccaaaaac gaggaggatt tgatattcac ctggcccgat | 1080 |
| ctggccatac acttgagtga caatgacatc cactttgcct ttctctccac aggtgtccac | 1140 |
| tcccaggtcc aagtttaaac gccgccacca tg | 1172 |

<210> SEQ ID NO 50
<211> LENGTH: 1165
<212> TYPE: DNA
<213> ORGANISM: Artificial Sequence
<220> FEATURE:
<223> OTHER INFORMATION: Made in Lab - Polynucleotide cassette 12 full 3'

<400> SEQUENCE: 50

| | |
|---|---|
| tgaggcatgc ttctatatta ttttctaaaa gatttaaagt tttgccttct ccatttagac | 60 |

```
ttataattca ctggaattt ttttgtgtgta tggtatgaca tatgggttcc cttttatttt      120
ttacatataa atatatttcc ctgttttct aaaaaagacc taggaaaact gtcttcataa      180
caggcctatt gattggaaag tttgtcaacg aattgtgggt cttttggggt ttgctgcccc      240
ttttacgcaa tgtggatatc ctgctttaat gcctttatat gcatgtatac aagcaaaaca      300 ggctttact ttctcgccaa cttacaaggc cttctcagt aaacagtata tgacccttta       360
ccccgttgct cggcaacggc ctggtctgtg ccaagtgttt gctgacgcaa cccccactgg      420
ttggggcttg gccataggcc atcagcgcat gcgtggaacc tttgtgtctc ctctgccgat      480
ccatactgcg gaactcctag ccgcttgttt tgctcgcagc aggtctggag caaacctcat      540
cgggaccgac aattctgtcg tactctcccg caagtataca tcgtttccat ggctgctagg      600
ctgtgctgcc aactgatcc tgcgcgggac gtcctttgtt tacgtcccgt cggcgctgaa       660
tcccgcggac gacccctccc ggggccgctt ggggctctac cgcccgcttc tccgtctgcc      720
gtaccgtccg accacggggc gcacctctct ttacgcggac tccccgtctg tgccttctca      780
tctgccggac cgtgtgcact tcgcttcacc tctgcacgtc gcatggaggc caccgtgaac      840
gcccaccgga acctgcccaa ggtcttgcat aagaggactc ttggactttc agcaatgtca      900
tcttgccagc catctgttgt tgccccctcc ccgtgccttc cttgaccct ggaaggtgcc      960 actcccactg tcctttccta ataaaatgag gaaattgcat cgcattgtct gagtaggtgt     1020
cattctattc tgggggtgg ggtgggcag acagcaagg gggaggattg gaatacaat       1080 agcaggcatg ctggggatgc ggtgggctct atgggtaccc aggtgctgaa gaattgaccc     1140
ggttcctcct ggggaagaca gtcag                                          1165

<210> SEQ ID NO 51
<211> LENGTH: 820
<212> TYPE: DNA
<213> ORGANISM: Artificial Sequence
<220> FEATURE:
<223> OTHER INFORMATION: Made in Lab - Polynucleotide cassette 13 full
      5'

<400> SEQUENCE: 51
ctctggagac gacttacggt aaatggcccg cctggctgac cgcccaacga ccccgccca        60 ttgacgtcaa taatgacgta tgttcccata gtaacgccaa tagggacttt ccattgacgt      120
caatgggtgg agtatttacg gtaaactgcc cacttggcag tacatcaagt gtatcatatg      180
ccaagtccgc ccctattga cgtcaatgac ggtaaatggc ccgcctggca ttatgcccag      240
tacatgacct tacgggactt tcctacttgg cagtacatct acgtattagt catcgctatt      300
accatggtcg aggtgagccc cacgttctgc ttcactctcc ccatctcccc ccctcccca      360 cccccaattt tgtatttatt tattttttaa ttattttgtg cagcgatggg ggcggggggg      420
ggggggcgcg cgccaggcgg ggcggggcgg ggcgagggc gggcggggc gaggcggaga       480 ggtgcgcgg cagccaatca gagcggcgcg ctccgaaagt ttccttttat ggcgaggcgg       540
cggcggcggc ggccctataa aaagcgaagc gcgcggcggg cggcgtctca ggggagatct      600
ggtgaggtgt ggcaggcttg agatccagct gttggggtga gtactccctc tcaaaagcgg      660
gcattacttc tgcgctaaga ttgtcagttt ccaaaaacga ggaggattg atattcacct       720 ggcccgatct ggccatacac ttgagtgaca atgacatcca ctttgccttt ctctccacag      780
gtgtccactc ccaggtccaa gtttaaacgc cgccaccatg                          820

<210> SEQ ID NO 52
```

<211> LENGTH: 1443
<212> TYPE: DNA
<213> ORGANISM: Artificial Sequence
<220> FEATURE:
<223> OTHER INFORMATION: Made in Lab - Polynucleotide cassette 13 full 3'

<400> SEQUENCE: 52

```
ggttcccttt tattttttac atataaatat atttccctgt ttttctaaaa aagaaaaaga      60
tcatcatttt cccattgtaa aatgccatat ttttttcata ggtcacttac atatatcaat     120
gggtctgttt ctgagctcta ctctatttta tcagcctcac tgtctatccc cacacatctc     180
atgctttgct ctaaatcttg atatttagtg gaacattctt tcccattttg ttctacaaga     240
atattttgt tattgtcttt gggctttcta tatacatttt gaaatgaggt tgacaagtta      300
cctaggaaaa ctgtcttcat aacaggccta ttgattggaa agtttgtcaa cgaattgtgg     360
gtcttttggg gtttgctgcc ccttttacgc aatgtggata tcctgcttta atgcctttat     420
atgcatgtat acaagcaaaa caggcttta ctttctcgcc aacttacaag gcctttctca      480
gtaaacagta tatgacccctt taccccgttg ctcggcaacg gcctggtctg tgccaagtgt    540
ttgctgacgc aaccccact ggttgggct tggccatagg ccatcagcgc atgcgtggaa       600
cctttgtgtc tcctctgccg atccatactg cggaactcct agccgcttgt tttgctcgca    660
gcaggtctgg agcaaacctc atcgggaccg acaattctgt cgtactctcc cgcaagtata    720
catcgtttcc atggctgcta ggctgtgctg ccaactggat cctgcgcggg acgtcctttg    780
tttacgtccc gtcggcgctg aatcccgcgg acgaccctc ccggggccgc ttggggctct     840
accgcccgct tctccgtctg ccgtaccgtc cgaccacggg gcgcacctct ctttacgcgg    900
actcccgtc tgtgccttct catctgccgg accgtgtgca cttcgcttca cctctgcacg     960
tcgcatggag gccaccgtga acgcccaccg gaacctgccc aaggtcttgc ataagaggac   1020
tcttggactt tcagcaatgt catctggcta ataaggaaaa tttattttca ttgcaatagt   1080
gtgttggaat tttttgtgtc tctcactcgg aaggacatat gggagggcaa atcatttaaa   1140
acatcagaat gagtatttgg tttagagttt ggcaacatat gcccatatgc tggctgccat   1200
gaacaaaggt tggctataaa gaggtcatca gtatatgaaa cagcccctg ctgtccattc    1260
cttattccat agaaaagcct tgacttgagg ttagattttt tttatatttt gttttgtgtt   1320
atttttttct ttaacatccc taaaatttc cttacatgtt ttactagcca gattttcct    1380
cctctcctga ctactcccag tcatagctgt ccctcttctc ttatggagat cgaagacagt   1440
cag                                                                 1443
```

<210> SEQ ID NO 53
<211> LENGTH: 920
<212> TYPE: DNA
<213> ORGANISM: Artificial Sequence
<220> FEATURE:
<223> OTHER INFORMATION: Made in Lab - Polynucleotide cassette 14 full 5'

<400> SEQUENCE: 53

```
ctctggagac gacttacggt aaatggcccg cctggctgac cgcccaacga cccccgccca      60
ttgacgtcaa taatgacgta tgttcccata gtaacgccaa tagggacttt ccattgacgt     120
caatgggtgg agtatttacg gtaaactgcc cacttggcag tacatcaagt gtatcatatg     180
ccaagtccgc cccctattga cgtcaatgac ggtaaatggc ccgcctggca ttatgcccag     240
tacatgacct tacgggactt tcctacttgg cagtacatct acgtattagt catcgctatt     300
```

```
accatgctga tgcggttttg gcagtacacc aatgggcgtg gatagcggtt tgactcacgg    360
ggatttccaa gtctccaccc cattgacgtc aatgggagtt tgttttggca ccaaaatcaa    420
cgggactttc caaaatgtcg taataacccc gccccgttga cgcaaatggg cggtaggcgt    480
gtacggtggg aggtctatat aagcagagct cgtttagtga accgtcagat cgcctggaga    540
ggccatccac gctgttttga cctccatagt ggacaccggg accgatccag cctccgcggc    600
cgggaacggt gcattggaac gcggattccc cgtgccaaga gtgaccctgg cagaactcgg    660
taagtctgtt gacatgtatg tgatgtatac taacctgcat gggacgtgga tttacttgtg    720
tatgtcagat agagtaaaga ttaactcttg catgtgagcg gggcatcgag atagcgataa    780
atgagtcagg aggacggata cttatatgtg ttgttatcct cctctacagt caaacagatt    840
aagcgtctca ggggagatct agcttgcttg ttcttttttgc agaagctcag aataaacgct    900
caactttggc cgccaccatg                                                920

<210> SEQ ID NO 54
<211> LENGTH: 1821
<212> TYPE: DNA
<213> ORGANISM: Artificial Sequence
<220> FEATURE:
<223> OTHER INFORMATION: Made in Lab - Polynucleotide cassette 14 full
      3'

<400> SEQUENCE: 54
ctgttctcat cacatcatat caaggttata taccatcaat attgccacag atgttactta     60
gccttttaat atttctctaa tttagtgtat atgcaatgat agttctctga tttctgagat    120
tgagtttctc atgtgtaatg attatttaga gtttctcttt catctgttca aattttttgtc   180 tagttttatt ttttactgat ttgtaagact tctttttata atctgcatat tacaattctc    240
tttactgggg tgttgcaaat attttctgtc attctatggc ctgacttttc ttaatggttt    300 tttaattta aaaataagtc ttaatattca tgcaatctaa ttaacaatct tttctttgtg     360
gttaggactt tgagtcataa gaaattttt tctacactga agtcatgatg gcatgcttct    420
atattatttt ctaaaagatt taagttttg ccttctccat ttagacttat aattcactgg    480
aatttttttg tgtgtatggt atgacatatg ggttcccttt tatttttttac atataaatat    540 atttccctgt ttttctaaaa aagaaaaaga tcatcattttt cccattgtaa aatgccatat    600
ttttttcata ggtcacttac atatatcaat gggtctgttt ctgagctcta ctctatttta    660
tcagcctcac tgtctatccc cacacatctc atgctttgct ctaaatcttg atatttagtg    720
gaacattctt tcccattttg ttctacaaga atattttttgt tattgtctttt gggctttcta    780 tatacatttt gaaatgaggt tgacaagtta cctaggaaaa ctgtcttcat aatcaacctc    840
tggattacaa aatttgtgaa agattgactg gtattcttaa ctatgttgct ccttttacgc    900
tatgtggata cgctgcttta atgcctttgt atcatgctat tgcttcccgt atggctttca    960
ttttctcctc cttgtataaa tcctggttgc tgtctctttta tgaggagttg tggcccgttg   1020
tcaggcaacg tggcgtggtg tgcactgtgt ttgctgacgc aaccccccact ggttggggca   1080 ttgccaccac ctgtcagctc cttttccggga ctttcgcttt ccccctccct attgccacgg   1140
cggaactcat cgccgcctgc cttgcccgct gctggacagg gctcggctg ttgggcactg    1200 acaattccgt ggtgttgtcg gggaaatcat cgtcctttcc ttggctgctc gcctgtgttg   1260
ccacctggat tctgcgcggg acgtccttct gctacgtccc ttcggccctc aatccagcgg   1320
accttccttc ccgcggcctg ctgccggctc tgcggcctct tccgcctctt cgccttcgcc   1380
```

```
ctcagacgag tcggatctcc ctttgggccg cctccccgca tctggctaat aaaggaaatt    1440
tattttcatt gcaatagtgt gttggaattt tttgtgtctc tcactcggaa ggacatatgg    1500
gagggcaaat catttaaaac atcagaatga gtatttggtt tagagtttgg caacatatgc    1560
ccatatgctg gctgccatga acaaaggttg gctataaaga ggtcatcagt atatgaaaca    1620 gcccctgct gtccattcct tattccatag aaaagccttg acttgaggtt agatttttt    1680 tatattttgt tttgtgttat tttttctttt aacatcccta aaattttcct tacatgtttt    1740
actagccaga ttttcctcc tctcctgact actcccagtc atagctgtcc ctcttctctt    1800
atggagatcg aagacagtca g                                              1821
```

<210> SEQ ID NO 55
<211> LENGTH: 643
<212> TYPE: DNA
<213> ORGANISM: Artificial Sequence
<220> FEATURE:
<223> OTHER INFORMATION: Made in Lab - Polynucleotide cassette 15 full
      5'

<400> SEQUENCE: 55

```
ctctggagac gacttacggt aaatggcccg cctggctgac cgcccaacga ccccgccca      60 ttgacgtcaa taatgacgta tgttcccata gtaacgccaa tagggacttt ccattgacgt    120
caatgggtgg agtatttacg gtaaactgcc cacttggcag tacatcaagt gtatcatatg    180
ccaagtccgc cccctattga cgtcaatgac ggtaaatggc ccgcctggca ttatgcccag    240
tacatgacct tacgggactt tcctacttgg cagtacatct acgtattagt catcgctatt    300
accatgctga tgcggttttg gcagtacacc aatgggcgtg gatagcggtt tgactcacgg    360
ggatttccaa gtctccaccc cattgacgtc aatgggagtt tgttttggca ccaaaatcaa    420
cgggactttc caaaatgtcg taataacccc gccccgttga cgcaaatggg cggtaggcgt    480
gtacggtggg aggtctatat aagcagagct cgtttagtga accgtcagat cgcctggaga    540
ggccatccac gctgttttga cctccatagt ggacaccggg accgatccag cctccgcgtc    600
tcagggagag tctacaccca agctgtctag agccgccacc atg                      643
```

<210> SEQ ID NO 56
<211> LENGTH: 1953
<212> TYPE: DNA
<213> ORGANISM: Artificial Sequence
<220> FEATURE:
<223> OTHER INFORMATION: Made in Lab - Polynucleotide cassette 15 full
      3'

<400> SEQUENCE: 56

```
ctgttctcat cacatcatat caaggttata taccatcaat attgccacag atgttactta      60
gccttttaat atttctctaa tttagtgtat atgcaatgat agttctctga tttctgagat    120
tgagtttctc atgtgtaatg attatttaga gtttctcttt catctgttca aattttgtc     180 tagtttatt ttttactgat ttgtaagact tcttttata atctgcatat acaattctc       240 tttactgggg tgttgcaaat attttctgtc attctatggc ctgactttc ttaatggttt     300 tttaattta aaataagtc ttaatattca tgcaatctaa ttaacaatct tttctttgtg      360
gttaggactt tgagtcataa gaaattttc tctacactga agtcatgatg gcatgcttct     420 atattttt ctaaaagatt taagttttg ccttctccat ttagacttat aattcactgg       480 aattttttg tgtgtatggt atgacatatg ggttccctt tatttttac atataaatat       540
```

```
atttccctgt ttttctaaaa aagaaaaaga tcatcatttt cccattgtaa aatgccatat        600 tttttttcata ggtcacttac atatatcaat gggtctgttt ctgagctcta ctctatttta      660
tcagcctcac tgtctatccc cacacatctc atgctttgct ctaaatcttg atatttagtg      720
gaacattctt tcccattttg ttctacaaga atattttttgt tattgtcttt gggcttttcta     780 tatacatttt gaaatgaggt tgacaagtta cctaggaaaa ctgtcttcat aacaggccta       840
ttgattggaa agtttgtcaa cgaattgtgg gtcttttggg gtttgctgcc ccttttacgc       900
aatgtggata tcctgcttta atgcctttat atgcatgtat acaagcaaaa caggctttta      960 cttttctcgcc aacttacaag gccttttctca gtaaacagta tatgacccctt taccccgttg    1020 ctcggcaacg gcctggtctg tgccaagtgt ttgctgacgc aacccccact ggttggggct      1080
tggccatagg ccatcagcgc atgcgtggaa cctttgtgtc tcctctgccg atccatactg      1140
cggaactcct agccgcttgt tttgctcgca gcaggtctgg agcaaacctc atcgggaccg      1200
acaattctgt cgtactctcc cgcaagtata catcgtttcc atggctgcta ggctgtgctg      1260
ccaactggat cctgcgcggg acgtcctttg tttacgtccc gtcggcgctg aatcccgcgg      1320 acgaccctc ccggggccgc ttggggctct accgcccgct ctccgtctg ccgtaccgtc        1380 cgaccacggg gcgcacctct cttacgcgg actcccccgtc tgtgccttct catctgccgg     1440
accgtgtgca cttcgcttca cctctgcacg tcgcatggag ccaccgtga acgcccaccg       1500 gaacctgccc aaggtcttgc ataagaggac tcttggactt tcagcaatgt catctggcta     1560 ataaggaaa tttattttca ttgcaatagt gtgttggaat tttttgtgtc tctcactcgg       1620
aaggacatat gggagggcaa atcatttaaa acatcagaat gagtatttgg tttagagttt      1680
ggcaacatat gcccatatgc tggctgccat gaacaaaggt tggctataaa gaggtcatca      1740
gtatatgaaa cagcccccctg ctgtccattc cttattccat agaaaagcct tgacttgagg    1800
ttagattttt ttatattt gttttgtgtt attttttttct ttaacatccc taaaatttc        1860 cttacatgtt ttactagcca gattttttcct cctctcctga ctactcccag tcatagctgt     1920
ccctcttctc ttatggagat cgaagacagt cag                                   1953
```

<210> SEQ ID NO 57
<211> LENGTH: 673
<212> TYPE: DNA
<213> ORGANISM: Artificial Sequence
<220> FEATURE:
<223> OTHER INFORMATION: Made in Lab - Polynucleotide cassette 16 full 5'

<400> SEQUENCE: 57

```
ctctggagac gacttacggt aaatggcccg cctggctgac cgcccaacga ccccccgccca       60 ttgacgtcaa taatgacgta tgttcccata gtaacgccaa tagggacttt ccattgacgt      120
caatgggtgg agtatttacg gtaaactgcc cacttggcag tacatcaagt gtatcatatg      180
ccaagtccgc ccctattga cgtcaatgac ggtaaatggc ccgcctggca ttatgcccag       240
tacatgacct tacgggactt tcctacttgg cagtacatct acgtattagt catcgctatt      300
accatgctga tgcggttttg gcagtacacc aatgggcgtg atagcggttt tgactcacgg      360
ggatttccaa gtctccaccc cattgacgtc aatgggagtt gtttttggca ccaaaatcaa     420
cgggactttc caaaatgtcg taataaccccc gccccgttga cgcaaatggg cggtaggcgt    480
gtacggtggg aggtctatat aagcagagct cgtttagtga accgtcagat cgcctggaga    540
ggccatccac gctgttttga cctccatagt ggacaccggg accgatccag cctccgcgtc    600
```

```
tcaggggaga tctagcttgc ttgttctttt tgcagaagct cagaataaac gctcaacttt        660
ggccgccacc atg                                                          673

<210> SEQ ID NO 58
<211> LENGTH: 1690
<212> TYPE: DNA
<213> ORGANISM: Artificial Sequence
<220> FEATURE:
<223> OTHER INFORMATION: Made in Lab - Polynucleotide cassette 16 full
      3'

<400> SEQUENCE: 58
ctgttctcat cacatcatat caaggttata taccatcaat attgccacag atgttactta        60
gccttttaat atttctctaa tttagtgtat atgcaatgat agttctctga tttctgagat       120
tgagtttctc atgtgtaatg attatttaga gtttctcttt catctgttca aattttttgtc     180 tagttttatt ttttactgat ttgtaagact tcttttttata atctgcatat tacaattctc     240
tttactgggg tgttgcaaat attttctgtc attctatggc ctgacttttc ttaatggttt      300
tttaatttta aaaataagtc ttaatattca tgcaatctaa ttaacaatct tttctttgtg      360
gttaggactt tgagtcataa gaattttttc tctacactga agtcatgatg gcatgcttct      420
atattatttt ctaaaagatt taaagttttg ccttctccat ttagacttat aattcactgg      480 aattttttg tgtgtatggt atgacatatg ggttcccttt tatttttac atataaatat       540 atttccctgt ttttctaaaa agaaaaaga tcatcatttt cccattgtaa aatgccatat       600 tttttttcata ggtcacttac atatatcaat gggtctgttt ctgagctcta ctctatttta    660
tcagcctcac tgtctatccc cacacatctc atgctttgct ctaaatcttg atatttagtg     720
gaacattctt tcccattttg ttctacaaga atatttttgt tattgtcttt gggctttcta     780
tatacatttt gaaatgaggt tgacaagtta cctaggaaaa ctgtcttcat ataatcaacc     840
tctggattac aaaatttgtg aaagattgac tggtattctt aactatgttg ctccttttac     900
gctatgtgga tacgctgctt taatgccttt gtatcatgct attgcttccc gtatggcttt    960
cattttctcc tccttgtata aatcctggtt gctgtctctt tatgaggagt tgtggcccgt   1020
tgtcaggcaa cgtggcgtgg tgtgcactgt gtttgctgac gcaaccccca ctggttgggg   1080
cattgccacc acctgtcagc tccttttccgg gactttcgct ttccccctcc ctattgccac  1140
ggcggaactc atcgccgcct gccttgcccg ctgctggaca ggggctcggc tgttgggcac   1200
tgacaattcc gtggtgttgt cggggaaatc atcgtccttt ccttggctgc tcgcctgtgt   1260
tgccacctgg attctgcgcg ggacgtcctt ctgctacgtc ccttcggccc tcaatccagc   1320
ggaccttcct tcccgcggcc tgctgccggc tctgcggcct cttccgcctc ttcgccttcg    1380
ccctcagacg agtcggatct ccctttgggc cgcctcccccg catcatcttg ccagccatct   1440
gttgtttgcc cctccccccgt gccttccttg accctggaag gtgccactcc cactgtcctt   1500
tcctaataaa atgaggaaat tgcatcgcat tgtctgagta ggtgtcattc tattctgggg   1560
ggtggggtgg ggcaggacag caaggggggag gattgggaat acaatagcag gcatgctggg  1620
gatgcggtgg gctctatggg tacccaggtg ctgaagaatt gacccggttc ctcctgggga   1680
agacagtcag                                                          1690

<210> SEQ ID NO 59
<211> LENGTH: 1126
<212> TYPE: DNA
<213> ORGANISM: Artificial Sequence
<220> FEATURE:
```

<223> OTHER INFORMATION: Made in Lab - Polynucleotide cassette 17 full
      5'

<400> SEQUENCE: 59

| | | | | | |
|---|---|---|---|---|---|
| ctctggagac | gacttacggt | aaatggcccg | cctggctgac | cgcccaacga | ccccgccca | 60 |
| ttgacgtcaa | taatgacgta | tgttcccata | gtaacgccaa | tagggacttt | ccattgacgt | 120 |
| caatgggtgg | agtatttacg | gtaaactgcc | cacttggcag | tacatcaagt | gtatcatatg | 180 |
| ccaagtccgc | ccctattga | cgtcaatgac | ggtaaatggc | ccgcctggca | ttatgcccag | 240 |
| tacatgacct | tacgggactt | tcctacttgg | cagtacatct | acgtattagt | catcgctatt | 300 |
| accaatgacg | tcgaggagaa | gttccccaac | tttcccgcct | ctcagccttt | gaaagaaaga | 360 |
| aaggggaggg | ggcaggccgc | gtgcagccgc | gagcggtgct | gggctccggc | tccaattccc | 420 |
| catctcagtc | gttcccaaag | tcctcctgtt | tcatccaagc | gtgtaagggt | ccccgtcctt | 480 |
| gactccctag | tgtcctgctg | cccacagtcc | agtcctggga | accagcaccg | atcacctccc | 540 |
| atcgggccaa | tctcagtccc | ttccccccta | cgtcggggcc | cacacgctcg | gtgcgtgccc | 600 |
| agttgaacca | ggcggctgcg | gaaaaaaaaa | agcggggaga | agtagggcc | cggctactag | 660 |
| cggttttacg | ggcgcacgta | gctcaggcct | caagaccttg | gctgggact | ggctgagcct | 720 |
| ggcgggaggc | ggggtccgag | tcaccgcctg | ccgccgcgcc | cccggtttct | ataaattgag | 780 |
| cccgcagcct | cccgcttcgc | tctctgctcc | tcctgttcga | cagtcagccg | catcttcttt | 840 |
| tgcgtcgcca | gcctggcaga | actcggtaag | tctgttgaca | tgtatgtgat | gtatactaac | 900 |
| ctgcatggga | cgtggattta | cttgtgtatg | tcagatagag | taaagattaa | ctcttgcatg | 960 |
| tgagcgggc | atcgagatag | cgataaatga | gtcaggagga | cggatactta | tatgtgttgt | 1020 |
| tatcctcctc | tacagtcaaa | cagattaagc | gtctcagggg | agatctagct | tgcttgttct | 1080 |
| ttttgcagaa | gctcagaata | aacgctcaac | tttggccgcc | accatg | | 1126 |

<210> SEQ ID NO 60
<211> LENGTH: 1126
<212> TYPE: DNA
<213> ORGANISM: Artificial Sequence
<220> FEATURE:
<223> OTHER INFORMATION: Made in Lab - Polynucleotide cassette 17 full
      3'

<400> SEQUENCE: 60

| | | | | | |
|---|---|---|---|---|---|
| ggttcccttt | tattttttac | atataaatat | atttccctgt | ttttctaaaa | aagaaaaaga | 60 |
| tcatcatttt | cccattgtaa | aatgccatat | tttttcata | ggtcacttac | atatatcaat | 120 |
| gggtctgttt | ctgagctcta | ctctatttta | tcagcctcac | tgtctatccc | cacacatctc | 180 |
| atgctttgct | ctaaatcttg | atatttagtg | gaacattctt | tcccattttg | ttctacaaga | 240 |
| atatttttgt | tattgtcttt | gggctttcta | tatacatttt | gaaatgaggt | tgacaagtta | 300 |
| cctaggaaaa | ctgtcttcat | aatcaacctc | tggattacaa | aatttgtgaa | agattgactg | 360 |
| gtattcttaa | ctatgttgct | cctttacgc | tatgtggata | cgctgcttta | atgcctttgt | 420 |
| atcatgctat | tgcttcccgt | atggctttca | ttttctcctc | cttgtataaa | tcctggttgc | 480 |
| tgtctcttta | tgaggagttg | tggcccgttg | tcaggcaacg | tggcgtggtg | tgcactgtgt | 540 |
| ttgctgacgc | aacccccact | ggttggggca | ttgccaccac | ctgtcagctc | ctttccggga | 600 |
| ctttcgcttt | cccctccct | attgccacgg | cggaactcat | cgccgcctgc | cttgcccgct | 660 |
| gctggacagg | ggctcggctg | ttgggcactg | acaattccgt | ggtgttgtcg | gggaaatcat | 720 |
| cgtcctttcc | ttggctgctc | gcctgtgttg | ccacctggat | tctgcgcggg | acgtccttct | 780 |

```
gctacgtccc ttcggccctc aatccagcgg accttccttc ccgcggcctg ctgccggctc    840
tgcggcctct tccgcctctt cgccttcgcc ctcagacgag tcggatctcc ctttgggccg    900
cctccccgca tcctgcccgg gtggcatccc tgtgacccct ccccagtgcc tctcctggcc    960
ctggaagttg ccactccagt gcccaccagc cttgtcctaa taaaattaag ttgcatcatt   1020
ttgtctgact aggtgtcctt ctataatatt atggggtgga ggggggtggt atggagcaag   1080
gggcccaagt tgggaagaaa cctgtagggc ctgcgaagac agtcag                  1126

<210> SEQ ID NO 61
<211> LENGTH: 820
<212> TYPE: DNA
<213> ORGANISM: Artificial Sequence
<220> FEATURE:
<223> OTHER INFORMATION: Made in Lab - Polynucleotide cassette 18 full
      5'

<400> SEQUENCE: 61
ctctggagac gacttacggt aaatggcccg cctggctgac cgcccaacga ccccgccca     60 ttgacgtcaa taatgacgta tgttcccata gtaacgccaa tagggacttt ccattgacgt    120
caatgggtgg agtatttacg gtaaactgcc cacttggcag tacatcaagt gtatcatatg    180
ccaagtccgc ccctattga cgtcaatgac ggtaaatggc ccgcctggca ttatgcccag     240
tacatgacct tacgggactt tcctacttgg cagtacatct acgtattagt catcgctatt    300
accatggtcg aggtgagccc cacgttctgc ttcactctcc ccatctcccc ccctccccca    360
ccccaatttt tgtatttatt tattttttaa ttattttgtg cagcgatggg ggcggggggg    420 gggggcgcg cgccaggcgg ggcggggcgg ggcgagggc ggggcgggg gaggcggaga       480 ggtgcggcgg cagccaatca gagcggcgcg ctccgaaagt tccttttat ggcgaggcgg     540 cggcggcgc ggccctataa aaagcgaagc gcgcggcggg cggcgtctca ggggagatct     600
ggtgaggtgt ggcaggcttg agatccagct gttggggtga gtactccctc tcaaaagcgg    660
gcattacttc tgcgctaaga ttgtcagttt ccaaaaacga ggaggatttg atattcacct    720
ggcccgatct ggccatacac ttgagtgaca atgacatcca ctttgccttt ctctccacag    780
gtgtccactc ccaggtccaa gtttaaacgc cgccaccatg                          820

<210> SEQ ID NO 62
<211> LENGTH: 1091
<212> TYPE: DNA
<213> ORGANISM: Artificial Sequence
<220> FEATURE:
<223> OTHER INFORMATION: Made in Lab - Polynucleotide cassette 18 full
      3'

<400> SEQUENCE: 62
ctgttctcat cacatcatat caaggttata taccatcaat attgccacag atgttactta     60
gccttttaat atttctctaa tttagtgtat atgcaatgat agttctctga tttctgagat    120
tgagtttctc atgtgtaatg attatttaga gtttctcttt catctgttca aattttttgtc   180 tagttttatt ttttactgat tgtaagact tcttttttata atctgcatat tacaattctc    240
tttactgggg tgttgcaaat attttctgtc attctatggc ctgactttc ttaatggttt    300 tttaatttta aaaataagtc ttaatattca tgcaatctaa ttaacaatct tttctttgtg    360
gttaggactt tgagtcataa gaatttttc tctacactga agtcatgatg gcatgcttct    420
atattatttt ctaaaagatt taagttttg ccttctccat ttagacttat aattcactgg    480
```

```
aatttttttg tgtgtatggt atgacatatg ggttcccttt tatttttttac atataaatat    540 atttccctgt ttttctaaaa aagaaaaaga tcatcattt cccattgtaa aatgccatat      600
ttttttcata ggtcacttac atatatcaat gggtctgttt ctgagctcta ctctatttta    660
tcagcctcac tgtctatccc cacacatctc atgctttgct ctaaatcttg atatttagtg    720
gaacattctt tcccattttg ttctacaaga atatttttgt tattgtcttt gggctttcta    780
tatacatttt gaaatgaggt tgacaagtta cctaggaaaa ctgtcttctt gccagccatc    840
tgttgtttgc ccctcccccg tgccttcctt gaccctggaa ggtgccactc ccactgtcct    900
ttcctaataa aatgaggaaa ttgcatcgca ttgtctgagt aggtgtcatt ctattctggg    960
gggtggggtg gggcaggaca gcaagggga ggattgggaa tacaatagca ggcatgctgg    1020
ggatgcggtg ggctctatgg gtacccaggt gctgaagaat tgacccggtt cctcctgggg    1080
aagacagtca g                                                          1091
```

<210> SEQ ID NO 63

<400> SEQUENCE: 63

000

<210> SEQ ID NO 64
<211> LENGTH: 151
<212> TYPE: DNA
<213> ORGANISM: Artificial Sequence
<220> FEATURE:
<223> OTHER INFORMATION: Made in Lab - Cassette 7 Enhancer Promoter
      Junction

<400> SEQUENCE: 64

```
gcccgcctgg cattatgccc agtacatgac cttatgggac tttcctactt ggcagtacat    60
ctacgtatta gtcatcgcta ttaccatggt cgaggtgagc cccacgttct gcttcactct   120
ccccatctcc cccccctccc caccccaat t                                    151
```

<210> SEQ ID NO 65
<211> LENGTH: 151
<212> TYPE: DNA
<213> ORGANISM: Artificial Sequence
<220> FEATURE:
<223> OTHER INFORMATION: Made in Lab - Cassette 7 Promoter Intro
      Junction

<400> SEQUENCE: 65

```
tccgaaagtt tccttttatg gcgaggcggc ggcggcggcg ccctataaa aagcgaagcg    60 cgcggcgggc gggagtcgct gcgcgctgcc ttcgccccgt gccccgctcc gccgccgcct   120
cgcgccgccc gccccggctc tgactgaccg c                                   151
```

<210> SEQ ID NO 66
<211> LENGTH: 86
<212> TYPE: DNA
<213> ORGANISM: Artificial Sequence
<220> FEATURE:
<223> OTHER INFORMATION: Made in Lab - Cassette 7 Intron 5' UTR Junction

<400> SEQUENCE: 66

```
agctcctggg caacgtgctg gttattgtgc tgtctcatca ttttggcaaa gaattcggct    60
tgatcgaagc cgtctcaggg gagatc                                          86
```

<210> SEQ ID NO 67

```
<211> LENGTH: 41
<212> TYPE: DNA
<213> ORGANISM: Artificial Sequence
<220> FEATURE:
<223> OTHER INFORMATION: Made in Lab - Cassette 7 UTR Kozak junction

<400> SEQUENCE: 67
tttttgcaga agctcagaat aaacgctcaa ctttggccgc c                   41

<210> SEQ ID NO 68
<211> LENGTH: 90
<212> TYPE: DNA
<213> ORGANISM: Artificial Sequence
<220> FEATURE:
<223> OTHER INFORMATION: Made in Lab - Cassette 7 Enhancer RNA Export
      Junction

<400> SEQUENCE: 68
ccctgttttt ctaaaaaaga cctaggaaaa ctgtcttcat aacaggccta ttgattggaa    60
agtttgtcaa cgaattgtgg gtcttttggg                                    90

<210> SEQ ID NO 69
<211> LENGTH: 90
<212> TYPE: DNA
<213> ORGANISM: Artificial Sequence
<220> FEATURE:
<223> OTHER INFORMATION: Made in Lab - Cassette 7 RNA Export PolyA
      Junction

<400> SEQUENCE: 69
ccctgttttt ctaaaaaaga cctaggaaaa ctgtcttcat aacaggccta ttgattggaa    60
agtttgtcaa cgaattgtgg gtcttttggg                                    90

<210> SEQ ID NO 70
<211> LENGTH: 100
<212> TYPE: DNA
<213> ORGANISM: Artificial Sequence
<220> FEATURE:
<223> OTHER INFORMATION: Made in Lab - Cassette 10 Enhancer Promoter
      Junction

<400> SEQUENCE: 70
cgggactttc ctacttggca gtacatctac gtattagtca tcgctattac cagcacatcg    60
cccacagtcc ccgagaagtt ggggggaggg gtcggcaatt                         100

<210> SEQ ID NO 71
<211> LENGTH: 120
<212> TYPE: DNA
<213> ORGANISM: Artificial Sequence
<220> FEATURE:
<223> OTHER INFORMATION: Made in Lab - Cassette 10 Promoter Intron
      Junction

<400> SEQUENCE: 71
gggtggggga gaaccgtata taagtgcagt agtcgccgtg aacgttcttt ttcgcaacgg    60
gtttgccgcc agaacacagg taagtgccgt gtgtggttcc cgcgggcctg gcctctttac   120

<210> SEQ ID NO 72
<211> LENGTH: 55
<212> TYPE: DNA
<213> ORGANISM: Artificial Sequence
<220> FEATURE:
<223> OTHER INFORMATION: Made in Lab - Cassette 10 Intron UTR

<400> SEQUENCE: 72
```

```
gacagtggtt caaagttttt ttcttccatt tcaggtgtcc tgaacacgtc tcagg          55
```

<210> SEQ ID NO 73
<211> LENGTH: 15
<212> TYPE: DNA
<213> ORGANISM: Artificial Sequence
<220> FEATURE:
<223> OTHER INFORMATION: Made in Lab - Cassette 10 UTR Kozak junction

<400> SEQUENCE: 73

```
agctgtctag agccg                                                     15
```

<210> SEQ ID NO 74
<211> LENGTH: 146
<212> TYPE: DNA
<213> ORGANISM: Artificial Sequence
<220> FEATURE:
<223> OTHER INFORMATION: Made in Lab - Cassette 10 Enhancer RNA Export
      Junction

<400> SEQUENCE: 74

```
gtctttgggc tttctatata cattttgaaa tgaggttgac aagttaccta ggaaaactgt    60
cttcatataa tcaacctctg gattacaaaa tttgtgaaag attgactggt attcttaact   120
atgttgctcc ttttacgcta tgtgga                                        146
```

<210> SEQ ID NO 75
<211> LENGTH: 98
<212> TYPE: DNA
<213> ORGANISM: Artificial Sequence
<220> FEATURE:
<223> OTHER INFORMATION: Made in Lab - Cassette 10 RNA Export PolyA
      Junction

<400> SEQUENCE: 75

```
cttcgccctc agacgagtcg gatctcccct tgggccgcct ccccgcatca tcttgccagc    60
catctgttgt ttgccccctcc cccgtgcctt ccttgacc                           98
```

<210> SEQ ID NO 76
<211> LENGTH: 68
<212> TYPE: DNA
<213> ORGANISM: Artificial Sequence
<220> FEATURE:
<223> OTHER INFORMATION: Made in Lab - Cassette 11 TPL Enhancer junction

<400> SEQUENCE: 76

```
aggcggtctt gagacggcgg atggtcgagg tgaggtgtgg caggcttgag atccagctgt    60
tggggtga                                                             68
```

<210> SEQ ID NO 77
<211> LENGTH: 129
<212> TYPE: DNA
<213> ORGANISM: Artificial Sequence
<220> FEATURE:
<223> OTHER INFORMATION: Made in Lab - Cassette 11 Promoter TPL
      Junction

<400> SEQUENCE: 77

```
cgctgttttg acctccatag tggacaccgg gaccgatcca gcctccgcgt ctcagggag    60 atctcgttta gtgaaccgtc agatcctcac tctcttccgc atcgctgtct gcgagggcca  120
gctgttggg                                                           129
```

```
<210> SEQ ID NO 78
<211> LENGTH: 36
<212> TYPE: DNA
<213> ORGANISM: Artificial Sequence
<220> FEATURE:
<223> OTHER INFORMATION: Made in Lab - Cassette 11 Promoter Intron
      Junction

<400> SEQUENCE: 78
ttgatattca cctggcccga tctggccata cacttg                                    36

<210> SEQ ID NO 79
<211> LENGTH: 22
<212> TYPE: DNA
<213> ORGANISM: Artificial Sequence
<220> FEATURE:
<223> OTHER INFORMATION: Made in Lab - Cassette 11 UTR Kozak junction

<400> SEQUENCE: 79
cccaggtcca agtttaaacg cc                                                   22

<210> SEQ ID NO 80
<211> LENGTH: 77
<212> TYPE: DNA
<213> ORGANISM: Artificial Sequence
<220> FEATURE:
<223> OTHER INFORMATION: Made in Lab - Cassette 11 Enhancer PolyA
      Junction

<400> SEQUENCE: 80
tctttgggct ttctatatac attttgaaat gaggttgaca agttacctag gaaaactgtc          60
ttcctgcccg ggtggca                                                         77

<210> SEQ ID NO 81
<211> LENGTH: 149
<212> TYPE: DNA
<213> ORGANISM: Artificial Sequence
<220> FEATURE:
<223> OTHER INFORMATION: Made in Lab - Cassette 12 Promoter TPL Junction

<400> SEQUENCE: 81
tcagatcgcc tggagaggcc atccacgctg ttttgacctc catagtggac accgggaccg          60
atccagcctc cgcgtctcag gggagatctc gtttagtgaa ccgtcagatc ctcactctct         120
tccgcatcgc tgtctgcgag ggccagctg                                           149

<210> SEQ ID NO 82
<211> LENGTH: 95
<212> TYPE: DNA
<213> ORGANISM: Artificial Sequence
<220> FEATURE:
<223> OTHER INFORMATION: Made in Lab - Cassette 12 TPL Enhancer Junction

<400> SEQUENCE: 82
gatgtaatta aagtaggcgg tcttgagacg gcggatggtc gaggtgaggt gtggcaggct          60
tgagatccag ctgttggggt gagtactccc tctca                                     95

<210> SEQ ID NO 83
<211> LENGTH: 41
<212> TYPE: DNA
<213> ORGANISM: Artificial Sequence
<220> FEATURE:
<223> OTHER INFORMATION: Made in Lab - Cassette 12 Enhancer Intro
      Junction

<400> SEQUENCE: 83
```

```
gatttgatat tcacctggcc cgatctggcc atacacttga g                    41
```

<210> SEQ ID NO 84
<211> LENGTH: 29
<212> TYPE: DNA
<213> ORGANISM: Artificial Sequence
<220> FEATURE:
<223> OTHER INFORMATION: Made in Lab - Cassette 12 UTR Kozak junction

<400> SEQUENCE: 84

```
tgtccactcc caggtccaag tttaaacgc                                  29
```

<210> SEQ ID NO 85
<211> LENGTH: 76
<212> TYPE: DNA
<213> ORGANISM: Artificial Sequence
<220> FEATURE:
<223> OTHER INFORMATION: Made in Lab - Cassette 12 Enhancer RNA Export
      Junction

<400> SEQUENCE: 85

```
tgtttttcta aaaagacct aggaaaactg tcttcataac aggcctattg attggaaagt    60
ttgtcaacga attgtg                                                  76
```

<210> SEQ ID NO 86
<211> LENGTH: 110
<212> TYPE: DNA
<213> ORGANISM: Artificial Sequence
<220> FEATURE:
<223> OTHER INFORMATION: Made in Lab - Cassette 12 RNA Export PolyA
      Junction

<400> SEQUENCE: 86

```
aaggtcttgc ataagaggac tcttggactt tcagcaatgt catcttgcca gccatctgtt    60
gtttgcccct ccccgtgcc ttccttgacc ctggaaggtg ccactcccac              110
```

<210> SEQ ID NO 87
<211> LENGTH: 110
<212> TYPE: DNA
<213> ORGANISM: Artificial Sequence
<220> FEATURE:
<223> OTHER INFORMATION: Made in Lab - Cassette 13 Promoter Enhancer
      Junction

<400> SEQUENCE: 87

```
gcggccctat aaaaagcgaa gcgcgcggcg ggcggcgtct caggggagat ctggtgaggt    60
gtggcaggct tgagatccag ctgttggggt gagtactccc tctcaaaagc              110
```

<210> SEQ ID NO 88
<211> LENGTH: 44
<212> TYPE: DNA
<213> ORGANISM: Artificial Sequence
<220> FEATURE:
<223> OTHER INFORMATION: Made in Lab - Cassette 13 Enhancer Intron
      Junction

<400> SEQUENCE: 88

```
ggaggatttg atattcacct ggcccgatct ggccatacac ttga                   44
```

<210> SEQ ID NO 89
<211> LENGTH: 49
<212> TYPE: DNA
<213> ORGANISM: Artificial Sequence
<220> FEATURE:

```
<223> OTHER INFORMATION: Made in Lab - Cassette 13 Intron Kozak Junction

<400> SEQUENCE: 89
cctttctctc cacaggtgtc cactcccagg tccaagttta aacgccgcc          49

<210> SEQ ID NO 90
<211> LENGTH: 129
<212> TYPE: DNA
<213> ORGANISM: Artificial Sequence
<220> FEATURE:
<223> OTHER INFORMATION: Made in Lab - Cassette 13 Enhancer RNA Export
      Junction

<400> SEQUENCE: 90
attgtctttg ggctttctat atacattttg aaatgaggtt gacaagttac ctaggaaaac    60
tgtcttcata acaggcctat tgattggaaa gtttgtcaac gaattgtggg tcttttgggg   120
tttgctgcc                                                          129

<210> SEQ ID NO 91
<211> LENGTH: 110
<212> TYPE: DNA
<213> ORGANISM: Artificial Sequence
<220> FEATURE:
<223> OTHER INFORMATION: Made in Lab - Cassette 13 RNA Export PolyA
      Junction

<400> SEQUENCE: 91
cctgcccaag gtcttgcata agaggactct tggactttca gcaatgtcat ctggctaata    60
aaggaaattt attttcattg caatagtgtg ttggaatttt ttgtgtctct              110

<210> SEQ ID NO 92
<211> LENGTH: 94
<212> TYPE: DNA
<213> ORGANISM: Artificial Sequence
<220> FEATURE:
<223> OTHER INFORMATION: Made in Lab - Cassette 14 Promoter Intron
      Junction

<400> SEQUENCE: 92
cggtgcattg gaacgcggat tccccgtgcc aagagtgacc ctggcagaac tcggtaagtc    60
tgttgacatg tatgtgatgt atactaacct gcat                               94

<210> SEQ ID NO 93
<211> LENGTH: 112
<212> TYPE: DNA
<213> ORGANISM: Artificial Sequence
<220> FEATURE:
<223> OTHER INFORMATION: Made in Lab - Cassette 14 Intron Kozak junction

<400> SEQUENCE: 93
acttatatgt gttgttatcc tcctctacag tcaaacagat taagcgtctc aggggagatc    60
tagcttgctt gttctttttg cagaagctca gaataaacgc tcaactttgg cc           112

<210> SEQ ID NO 94
<211> LENGTH: 99
<212> TYPE: DNA
<213> ORGANISM: Artificial Sequence
<220> FEATURE:
<223> OTHER INFORMATION: Made in Lab - Cassette 14 Enhancer RNA Export
      Junction

<400> SEQUENCE: 94
gctttctata tacattttga aatgaggttg acaagttacc taggaaaact gtcttcataa    60
```

```
tcaacctctg gattacaaaa tttgtgaaag attgactgg                            99
```

<210> SEQ ID NO 95
<211> LENGTH: 100
<212> TYPE: DNA
<213> ORGANISM: Artificial Sequence
<220> FEATURE:
<223> OTHER INFORMATION: Made in Lab - Cassette 14 RNA Export PolyA
      Junction

<400> SEQUENCE: 95

```
cttcgccttc gccctcagac gagtcggatc tccctttggg ccgcctcccc gcatctggct    60
aataaaggaa atttattttc attgcaatag tgtgttggaa                         100
```

<210> SEQ ID NO 96
<211> LENGTH: 280
<212> TYPE: DNA
<213> ORGANISM: Gallus gallus

<400> SEQUENCE: 96

```
tggtcgaggt gagccccacg ttctgcttca ctctccccat ctcccccccc tccccacccc    60
caattttgta tttatttatt ttttaattat tttgtgcagc gatggggggcg ggggggggg   120 gggcgcgcgc caggcggggc ggggcggggc gaggggcggg gcggggcgag gcggagaggt   180
gcggcggcag ccaatcagag cggcgcgctc cgaaagtttc cttttatggc gaggcggcgg   240
cggcggcggc cctataaaaa gcgaagcgcg cggcgggcgg                         280
```

<210> SEQ ID NO 97
<211> LENGTH: 973
<212> TYPE: DNA
<213> ORGANISM: Gallus gallus

<400> SEQUENCE: 97

```
ggagtcgctg cgcgctgcct tcgccccgtg ccccgctccg ccgccgcctc gcgccgcccg    60
ccccggctct gactgaccgc gttactccca caggtgagcg ggcgggacgg cccttctcct   120
ccgggctgta attagcgctt ggtttaatga cggcttgttt cttttctgtg gctgcgtgaa   180
agccttgagg ggctccggga gggccctttg tgcgggggggg agcggctcgg ggggtgcgtg   240
cgtgtgtgtg tgcgtgggga gcgccgcgtg cggctccgcg ctgcccggcg gctgtgagcg   300
ctgcgggcgc ggcgcgggc tttgtgcgct ccgcagtgtg cgcgagggga gcgcggccgg   360
gggcggtgcc ccgcggtgcg gggggggctg cgaggggaac aaaggctgcg tgcgggtgt   420 gtgcgtgggg gggtgagcag gggtgtggg cgcgtcggtc gggctgcaac ccccctgca   480 cccccctccc cgagttgctg agcacggccc ggcttcgggt gcgggctcc gtacggggcg   540 tggcgcgggg ctcgccgtgc cgggcggggg gtggcggcag gtgggggtgc cgggcggggc   600
ggggccgcct cggccggggg agggctcggg ggaggggcgc ggcggccccc ggagcgccgg   660
cggctgtcga ggcgcggcga ccgcagccaa ttgccttttta tggtaatcgt gcgagagggc   720
gcagggactt cctttgtccc aaatctgtgc ggagccgaaa tctgggaggc gccgccgcac   780
cccctctagc gggcgcgggg cgaagcgtg cggcgccggc aggaaggaaa tgggcgggga   840
gggccttcgt gcgtcgccgc gccgccgtcc ccttctccct ctccagcctc ggggctgtcc   900
gcggggggac ggctgccttc gggggggacg gggcagggcg gggttcggct tctggcgtgt   960
gaccggcggc tct                                                     973
```